United States Patent
Hurley et al.

(10) Patent No.: US 9,475,837 B2
(45) Date of Patent: Oct. 25, 2016

(54) PROCESS FOR THE SYNTHESIS OF THERAPEUTIC PEPTIDES

(71) Applicant: IPSEN MANUFACTURING IRELAND LIMITED, Dublin (IE)

(72) Inventors: Fionn Hurley, Dublin (IE); Katarzyna Wegner, Dublin (IE); Patrick Foley, Co. Wexford (IE)

(73) Assignee: IPSEN MANUFACTURING IRELAND LIMITED, Dublin (IE)

( * ) Notice: Subject to any disclaimer, the term of this patent is extended or adjusted under 35 U.S.C. 154(b) by 0 days.

(21) Appl. No.: 14/368,154

(22) PCT Filed: Dec. 21, 2012

(86) PCT No.: PCT/IB2012/003056
§ 371 (c)(1),
(2) Date: Jun. 23, 2014

(87) PCT Pub. No.: WO2013/093639
PCT Pub. Date: Jun. 27, 2013

(65) Prior Publication Data
US 2015/0045534 A1  Feb. 12, 2015

Related U.S. Application Data

(60) Provisional application No. 61/580,089, filed on Dec. 23, 2011.

(51) Int. Cl.
| C07K 1/04 | (2006.01) |
|---|---|
| C07K 7/06 | (2006.01) |
| C07K 14/655 | (2006.01) |
| C07K 14/60 | (2006.01) |

(52) U.S. Cl.
CPC ............. *C07K 1/042* (2013.01); *C07K 1/04* (2013.01); *C07K 7/06* (2013.01); *C07K 14/60* (2013.01); *C07K 14/655* (2013.01)

(58) Field of Classification Search
None
See application file for complete search history.

(56) References Cited

U.S. PATENT DOCUMENTS

2008/0242619 A1* 10/2008 Dong .......................... 514/17
2009/0163416 A1* 6/2009 Tulipano ................ A61K 38/25
514/6.9

FOREIGN PATENT DOCUMENTS

| CN | 101538316 B | 9/2012 | |
|---|---|---|---|
| EP | 0473411 A1 | 8/1991 | |
| WO | 02100888 A1 | 12/2002 | |
| WO | 2004014415 A1 | 2/2004 | |
| WO | 2004091490 A2 | 10/2004 | |
| WO | 2007139589 A1 | 12/2007 | |
| WO | 2010141276 A1 | 12/2010 | |
| WO | WO 2010/141276 | * 12/2010 | ............... C07K 7/06 |

OTHER PUBLICATIONS

Kent, S.B.H., "Chemical Synthesis of Peptides and Proteins," Annual Review of Biochemistry, (1988), vol. 57, pp. 957-989.
Merrifield, R.B., "Sold Phase Peptde Synthesis. I. The Synthesis of a Tetrapeptde," Jounal of the Amercan Chemical Society, (1963), vol. 85, pp. 2149-2154.
Reid, Ronald Eric, "Solid Phase Peptide synthesis. Effect of trifluoroacetic acid concentration on the removal of the tert-butyloxycarbonyl protecting group," The Journal of Organic Chemistry, (1976), vol. 41, No. 6, pp. 1027-1031 (XP55064509).
Sieber, Peter, "A new acid-laile anchor group for the solid-phase synthesis of C-terminal peptide amides by the Fmoc method," Tetrahedron Letters, (197), vol. 28, No. 19, pp. 2107-2110.
Stathopoulos P. et al., "C-terminal N-alkylated peptide amides resulting from the linker decomposition of the Rink amide resin: a new cleavage mixture prevents their formation," Journal of Peptide Science: an official publication of the European Peptide Society, (2006), vol. 12, No. 3, pp. 227-232.
International Search Report and Written Opinion for PCT/IB2012/003056 dated Jun. 6, 2013.

* cited by examiner

*Primary Examiner* — Marcela M Cordero Garcia
*Assistant Examiner* — Catherine Mader
(74) *Attorney, Agent, or Firm* — Hunton & Williams LLP

(57) ABSTRACT

The present invention relates to a process for the large-scale synthesis of therapeutic peptides using a Sieber Amide resin, which comprises solid-phase Fmoc-chemistry.

18 Claims, 3 Drawing Sheets

Relative cost (materials based) – Rink Amide vs Sieber Amide

PROCESS FOR THE SYNTHESIS OF THERAPEUTIC PEPTIDES

CROSS-REFERENCE TO RELATED APPLICATIONS

This application is the U.S. National Phase of International Patent Application No. PCT/IB2012/003056, filed Dec. 21, 2012, which claims priority to U.S. Provisional Patent Application No. 61/580,089, filed Dec. 23, 2011, the contents of each are hereby incorporated by reference in their entireties.

The present invention relates to a novel process for the large-scale synthesis of therapeutic peptides containing unnatural or man-made amino acids. The method is scalable to large volumes and allows for the cost effective manufacturing of highly-pure peptides.

Solid-phase peptide synthesis (SPPS) is a highly successful method introduced first by Merrifield in 1963 (Merrifield, R. B., *J. Amer. Chem. Soc.*, 1963, 85:2149-54). Numerous peptides have been synthesized with this technique since then. Methods used in the prior art to chemically synthesize peptides and proteins are reviewed in Kent, S. B. H., *Ann. Rev. Biochem.*, 1988, 57:957-89. Solid-phase synthesis allows for the synthesis of natural peptides which are difficult to express in bacteria, the incorporation of unnatural or synthetic amino acids, peptide backbone modification and the synthesis of D-proteins containing D-amino acids.

Two strategies for the assembly of peptide chains by solid-phase synthesis have been used: 1). stepwise solid-phase synthesis and 2). solid-phase fragment condensation. In stepwise SPPS, the C-terminal amino acid in the form of an N-α-protected, and if necessary, side-chain-protected reactive derivative, is covalently coupled either directly or by means of a suitable linker to a "solid"-support, e.g., a polymeric resin, typically swollen in an organic solvent. The N-α-protective group is removed, and the subsequent protected amino acids are added in a stepwise fashion. When the desired peptide chain length has been obtained, the side chain protective groups are removed and the peptide is cleaved from the resin. The cleaving/de-protecting process may be done in separate steps or at the same time. In solid-phase fragment condensation, the target sequence is assembled by consecutive condensation of fragments on a solid support using protected fragments prepared by stepwise SPPS.

One form of SPPS relies on fluorenylmethyloxycarbonyl (or "Fmoc") to temporarily protect the α-amino group. With this method, the Fmoc group is covalently bound to the amino group to suppress its nucleophilicity. The C-terminal amino acid is covalently linked to the resin though a linker. Next, the Fmoc group is removed with base, such as piperidine. This liberates the amino group which is then available for reaction with an activated amino acid. Reactions are driven to completion by the use of excess (typically two- to four-fold) activated amino acid. After each de-protection and coupling step, one or more washes are performed to remove excess reagents. Cleavage of the peptide from the resin with removal of side chain protecting groups is achievable by acidolysis using an acidic solution, such as trifluoroacetic acid (TFA). It is common practice to add additional chemicals labeled as "scavengers" such as Triisopropylsilane (TIPS), Triethylsilane (TES), phenol, anisole, thioanisole, water, 1,2-ethanedithiol (EDT), 1-dodecanethiol, dithiothreitol (DTT) and indole, with the acid in the cleavage mixture to react with the liberated side chain protecting groups, thereby preventing those liberated groups from re-attaching to the cleaved peptide.

Amino acids have reactive moieties at the N- and C-termini which facilitate amino acid coupling during synthesis. In addition, the reactive side chain functional groups found on most amino acids can interact with free termini or other side chain groups during synthesis and peptide elongation and negatively influence yield and purity. To facilitate proper amino acid synthesis with minimal side chain reactivity, chemical groups, referred to as "protecting groups" are used to bind to the specific amino acid functional groups to "block" or "protect" the functional group from nonspecific reactions. Side chain protecting groups are known as permanent or semi-permanent protecting groups because they can withstand the multiple cycles of chemical treatment during synthesis and are only removed generally during treatment with strong acids after peptide synthesis is completed.

The current aforementioned strategies are not desirable for commercial scale production of the therapeutic peptides because the resins used therein require the peptide be removed using high concentrations of acid for cleavage of the peptide from the polymeric resin. Outside of the safety concerns of using large quantities of extremely corrosive material at large scale, special equipment may be required to permit its use. In addition, use of highly concentrated strong acids to cleave and de-protect peptides can result in serious degradation of the desired peptide resulting in low yield and/or the creation of new impurities as a result of the exposure of the peptide to strong acid for the period of time required to perform a cleavage and work-up on scale. Such impurities may include dehydrated or oxidized species or impurities related to the attachment of all or part of the resin-linker to the peptide—these impurities may be subsequently difficult to remove. As such, there is a need for developing an efficient large-scale method for producing therapeutic peptides.

As mentioned previously, solid-phase peptide synthesis is initiated on a "solid" support or anchor. These "supports" are referred to in the industry as "resins". Resins may be made from polystyrene or other polymeric materials, such as polymers of ethylene oxide, e.g. PEG based resins or a mixture of both, e.g. "hybrid" or PEG-polystyrene resins. Commonly used resins for manufacturing of peptide amides by the Fmoc SPPS route include polystyrene-based resins combined with a linker suitable for releasing a fully de-protected peptide amide upon treatment with high concentrations of acid. Commonly used resins include the Rink Amide resins, for example, Rink Amide resin, Rink Amide MBHA resin, and Rink Amide AM resin. Rink Amide resins release a fully de-protected peptide amide from the resin when treated with a high percentage v/v of acid in the cleavage cocktail—for example, 80-95% v/v trifluoroacetic acid (TFA) is typically used.

In 1987, a new acid-labile resin for the solid-phase synthesis of C-terminal amides was discovered by Sieber (*Tetrahedon Lett.*, 1987, 28(19):2107-10). This resin utilizes 9-xanthenyl group with a —$OCH_2$— group introduced between said xanthenyl group and the polystyrene to increase acid lability. Cleavage of peptide amides from this resin is performed by very mild acidolysis. The paper describes the synthesis of two peptides on this resin—the first with no side chain protecting groups (Z-Val-Gly-Ala-Pro-NH2) where cleavage from the resin on 0.5 g scale is effected by pumping an acidic cleavage mixture (TFA:1,2-dichloroethane 2:98 v/v) through the resin in a glass column; the second peptide (α-MSH), a 13 amino acid peptide that contains side chain-protected groups (tert-Butyl, Trt, Mtr, and Boc), was cleaved from the resin by pumping an acidic cleavage mixture (TFA/1,2-dichloroethane-/1,2-ethanedithiol 2:98:0.1) through a column with the resin. Two further steps with high concentrations of acid and heating (TFA/water 9:1 at 30° C., followed by 95% TFA with scavengers at 50° C.) were required to remove all the side chain protecting groups.

While not stated implicitly in the article above, the main usefulness of Sieber Amide resin (as the xanthenyl resin became known) was to produce fully side chain protected peptides for use in subsequent fragment condensation reactions. This is achievable through the use of low percentages v/v of acid in the cleavage cocktail—typically 1-5% v/v. According to a commercial supplier (Novabiochem®, Merck KGaA), Sieber resin is "[a] hyper acid-labile linker (resin) for the FMOC SPPS of protected peptide amides via mild 1% TFA cleavage."

It has been discovered that using Sieber Amide resin combined with Fmoc chemistry and a cleavage solution using certain concentrations of trifluoroacetic acid (TFA) (for example, above 10% v/v) can be used to synthesize fully de-protected peptide amides practically and on large scale (kg scale). This is a superior method for manufacturing fully de-protected peptide amides when compared to using Rink Amide resins, because:
  (i) it is possible to achieve greater manufacturing yields using this method
  (ii) it is possible to achieve greater purities of peptide using this method which allows for a more facile downstream purification
  (iii) it facilitates the reduced consumption of raw materials and solvents, and therefore is a more cost-effective method of manufacture
  (iv) it is a robust and reproducible method from small to large scale, therefore allowing for a facile scaling of the process.

The present invention provides a novel process for the large-scale synthesis of therapeutic peptides which comprises stepwise solid-phase Fmoc-chemistry.

In one aspect, the present invention provides a process for the synthesis of therapeutic peptides comprising the successive steps of:
  (a) swelling Fmoc-Sieber resin (also referred to as Sieber Amide resin or Fmoc Sieber Amide resin) in a dipolar aprotic solvent;
  (b) de-protecting the Fmoc group using a solution of piperidine in a dipolar aprotic solvent;
  (c) washing the resin after Fmoc de-protection with a dipolar aprotic solvent;
  (d) activating the Fmoc-amino acids for coupling to the de-protected resin by dissolving the Fmoc-amino acid and coupling reagent(s) in a dipolar aprotic solvent then adding a base and stirring;
  (e) charging the activated Fmoc-amino acid solution to the resin in the reactor;
  (f) coupling the activated Fmoc-amino acid using (2-(6-chloro-1H-benzotriazole-1-yl)-1,1,3,3-tetramethylaminium hexafluorophosphate) (HCTU) or 2-(1H-benzotriazole-1-yl)-1,1,3,3-tetramethyluronium tetrafluorocorate (TBTU)/1-hydroxybenzotriazole (HOBt) with a base in a dipolar aprotic solvent as a coupling reagent;
  (g) washing the resin after each Fmoc-amino acid coupling;
  (h) repeating steps (b)-(g) until a peptide is formed;
  (i) cleaving the desired peptide from the resin while simultaneously de-protecting the amino acid side chains using a cleavage cocktail;
  (j) filtering the cleavage mixture from the resin; and
  (k) evaporating the filtrates and precipitating and partially purifying the crude product from the concentrated solution with an organic solvent to yield a partially purified peptide.

According to steps (a), (b), (c) and (f) of the process as defined above, a dipolar aprotic solvent is used. Such dipolar aprotic solvent may be selected from dimethylformamide (DMF), dimethylacetamide (DMA) or N-methylpyrrolidone (NMP), or combinations thereof. In a preferred embodiment DMF is used as the dipolar aprotic solvent.

In another aspect, the present invention provides a process for the synthesis of therapeutic peptides comprising the successive steps of:
  (a) swelling Fmoc-Sieber resin (also referred to as Sieber Amide resin or Fmoc Sieber Amide resin) in dimethylformamide (DMF);
  (b) de-protecting the Fmoc group using a solution of piperidine in DMF;
  (c) washing the resin after Fmoc de-protection with DMF;
  (d) activating the Fmoc-amino acids for coupling to the de-protected resin by dissolving the Fmoc-amino acid and coupling reagent(s) in DMF then adding a base and stirring;
  (e) charging the activated Fmoc-amino acid solution to the resin in the reactor;
  (f) coupling the activated Fmoc-amino acids using (2-(6-chloro-1H-benzotriazole-1-yl)-1,1,3,3-tetramethylaminium hexafluorophosphate) (HCTU) or 2-(1H-benzotriazole-1-yl)-1,1,3,3-tetramethyluronium tetrafluorocorate (TBTU)/1-hydroxybenzotriazole (HOBt) with a base in DMF as a coupling reagent;
  (g) washing the resin after each Fmoc-amino acid coupling;
  (h) repeating steps (b)-(g) until a peptide is formed;
  (i) cleaving the desired peptide from the resin while simultaneously de-protecting the amino acid side chains using a cleavage cocktail;
  (j) filtering the cleavage mixture from the resin; and
  (k) evaporating the filtrates and precipitating and partially purifying the crude product from the concentrated solution with an organic solvent to yield a partially purified peptide.

According to step (d) of the process of the present invention as defined above, a base is used. Said base may be a tertiary amine base or a mixture thereof, and selected from N,N-diisopropylethylamine (DIEA), triethylamine (TEA), N-methylmorpholine (NMM), 2,4,6-trimethylpyrinidine (TMP, also known as collidine), 2,3,5,6-tetramethylpyridine (TEMP), 2,6-di-tert-butyl-4-dimethylaminopyridine (DBD-MAP), or 4-dimethylaminopyridine (DMAP). A preferred embodiment of the immediately foregoing aspect of the present invention is characterized in that the base used in step (d) is a tertiary amine, and that in a more preferred embodiment, said base is N,N-diisopropylethylamine (DIEA).

In another aspect, the present invention provides a process for the synthesis of therapeutic peptides comprising the steps of:
  (a) swelling Fmoc-Sieber resin (also referred to as Sieber Amide resin or Fmoc Sieber Amide resin) in dimethylformamide (DMF);
  (b) de-protecting the Fmoc group using a solution of piperidine in DMF;

(c) washing the resin after Fmoc de-protection with DMF;
(d) activating the Fmoc-amino acids for coupling to the de-protected resin by dissolving the Fmoc-amino acid and coupling reagent(s) in DMF then adding a base and stirring;
(e) charging the activated Fmoc-amino acid solution to the resin in the reactor;
(f) coupling the activated Fmoc-amino acids using (2-(6-chloro-1H-benzotriazole-1-yl)-1,1,3,3-tetramethylaminium hexafluorophosphate) (HCTU) or 2-(1H-benzotriazole-1-yl)-1,1,3,3-tetramethyluronium tetrafluorocorate (TBTU)/1-hydroxybenzotriazole (HOBt) with N,N-diisopropylethylamine (DIEA) in DMF as a coupling reagent;
(g) washing the resin after each Fmoc-amino acid coupling;
(h) repeating steps (b)-(g) until a peptide is formed;
(i) cleaving the desired peptide from the resin while simultaneously de-protecting the amino acid side chains using a cleavage cocktail;
(j) filtering the cleavage mixture from the resin; and
(k) evaporating the filtrates and precipitating and partially purifying the crude product from the concentrated solution with an organic anti-solvent to yield a partially purified peptide.

In another aspect, the present invention provides a process for the synthesis of therapeutic peptides comprising the successive steps of:
(a) swelling Fmoc-Sieber resin (also referred to as Sieber Amide resin or Fmoc Sieber Amide resin) in dimethylformamide (DMF);
(b) de-protecting the Fmoc group using a solution of piperidine in DMF;
(c) washing the resin after Fmoc de-protection with DMF;
(d) activating the Fmoc-amino acids for coupling to the de-protected resin by dissolving the Fmoc-amino acid and coupling reagent(s) in DMF then adding N,N-diisopropylethylamine (DIEA) and stirring;
(e) charging the activated Fmoc-amino acid solution to the resin in the reactor;
(f) coupling the activated Fmoc-amino acids using (2-(6-chloro-1H-benzotriazole-1-yl)-1,1,3,3-tetramethylaminium hexafluorophosphate) (HCTU) or 2-(1H-benzotriazole-1-yl)-1,1,3,3-tetramethyluronium tetrafluorocorate (TBTU)/1-hydroxybenzotriazole (HOBt) with N,N-diisopropylethylamine (DIEA) in DMF as a coupling reagent;
(g) washing the resin after each Fmoc-amino acid coupling;
(h) repeating steps (b)-(g) until a peptide is formed;
(i) cleaving the desired peptide from the resin while simultaneously de-protecting the amino acid side chains using a cleavage cocktail;
(j) filtering the cleavage mixture from the resin; and
(k) evaporating the filtrates and precipitating and partially purifying the crude product from the concentrated solution with an organic solvent to yield a partially purified peptide.

Another preferred embodiment of the present invention is characterized in that said cleavage cocktail used in step (i) of the process as defined above, is comprised of TFA, one or more scavenger and DCM wherein said scavenger is selected from the group consisting of Triisopropylsilane (TIPS), Triethylsilane (TES), phenol, anisole, thioanisole, water, 1,2-ethanedithiol (EDT), 1-dodecanethiol, dithiothreitol (DTT) and indole, provided that the percentage of TFA in said cleavage cocktail does not exceed 25%.

A preferred embodiment of the immediately foregoing aspect of the present invention is characterized in that said scavenger is selected from the group consisting of TIPS, TES, anisole and water.

Another preferred embodiment of the present invention is characterized in that said cleavage cocktail used in step (i) as defined above is comprised of TFA, one or more scavenger and DCM wherein said scavenger may be selected from the group consisting of TIPS, TES, anisole and water provided that the percentage of TFA in said cleavage cocktail does not exceed 25%.

For peptides wherein only Boc and tBu side chain protecting groups are required to be removed, a preferred embodiment of the present invention is characterized in that said cleavage cocktail consists of 15 to 25% v/v TFA with 2.5 to 12% v/v TIPS and 62.5 to 82.5% v/v DCM; and even more preferred to that said cleavage cocktail consists of 20% v/v TFA with 10% v/v TIPS and 70% v/v DCM.

For peptides wherein only Boc and tBu side chain protecting groups are required to be removed, a preferred embodiment of the process of the present invention as defined above is characterized in that:
said cleavage cocktail used in step (i) as defined above consists of 15 to 25% v/v TFA with 2.5 to 12% v/v TIPS and the remainder of the cleavage cocktail made up to 100% with DCM; and even more preferred to that
said cleavage cocktail used in step (i) as defined above consists of approximately 20% v/v TFA with approximately 10% v/v TIPS and 70% v/v DCM.

A further preferred embodiment of the process of present invention as defined above with steps (a) to (k) is that the resulting peptide is cleaved from the Sieber Amide resin concurrently with the de-protection of the side chain protecting groups.

Another preferred embodiment of the present invention is characterized in that the Fmoc group is initially removed from the resin using piperidine in DMF. In a more preferred embodiment, the Fmoc group is initially removed from the resin using piperidine in DMF wherein the concentration of said piperidine in DMF is less than 20% (v/v) and more preferably about 15% (v/v).

According to step (f) of the process of the present invention as defined above, the coupling of the activated Fmoc-amino acids is carried out using (2-(6-chloro-1H-benzotriazole-1-yl)-1,1,3,3-tetramethylaminium hexafluorophosphate) (HCTU) or 2-(1H-benzotriazole-1-yl)-1,1,3,3-tetramethyluronium tetrafluorocorate (TBTU)/1-hydroxybenzotriazole (HOBt) with a base such as N,N-diisopropylethylamine (DMA) in a dipolar aprotic solvent such as DMF, alone or in combination. In a preferred embodiment of any one of the foregoing aspects of the present invention, the amino acid residues are coupled using a "coupling reagent combination" selected from the group consisting of TBTU/HOBt/DIEA, HBTU/HOBt/DIEA, HATU/DIEA, HCTU/DIEA, DIC/HOBt, DIC/HOAt, HATU/HOBt/DIEA and HCTU/HOBt/DIEA, more preferably selected from the group consisting of HCTU/DIEA and TBTU/HOBt/DIEA.

A preferred embodiment of the process of the present invention with the successive steps (a) to (j) as defined above, is characterized in that, in step (a) (the Fmoc-Sieber-Amide resin is initially swelled using 1 to 3 treatments of 7 to 12 vols of DMF for up to 1 hour, even more preferred, 3 treatments of 10 vols of DMF lasting 10 to 30 minutes per treatment.

A preferred embodiment of the process of the present invention with the successive steps (a) to (j) as defined above, is characterized in that, in step (b), the Fmoc group on the Sieber resin is de-protected using 1 to 2 treatments with a solution of piperidine in DMF (10-20% v/v) lasting 5 to 20 minutes, even more preferred 2 treatments of 15% v/v piperidine in DMF lasting 10 minutes.

A preferred embodiment of the process of the present invention with the successive steps (a) to (j) as defined above, is characterized in that, in step (c), the de-protected resin is washed 3 to 5 times with 7 to 12 vols of DMF each wash lasting up to 5 minutes, even more preferred, 3 washes with 10 vols DMF each wash lasting up to 5 minutes.

A preferred embodiment of the process of the present invention with the successive steps (a) to (j) as defined above, is characterized in that, in step (d), 1.2-2.0 mol equivs (relative to the resin-batch scale) of the Fmoc-amino acid is activated for coupling by dissolving the Fmoc-amino acid and coupling reagent(s) in DMF, adding DIEA, stirring for up to 5 minutes; and more preferably 1.5 mol equivs (relative to the resin-batch scale) of the Fmoc-amino acid is activated for coupling by dissolving the Fmoc-amino acid and coupling reagent(s) in DMF, adding DIEA, stirring for 1 to 2 minutes.

A preferred embodiment of the process of the present invention with the successive steps (a) to (j) as defined above, is characterized in that, in step (f), 0.5 to 1.5 mol equivs (relative to Fmoc amino acid) of coupling reagent(s) is used with 1.5 to 2.5 mol equivs (relative to Fmoc amino acid) of DIEA in 4 to 10 vols DMF for 30 to 120 minutes at ambient temperature; and more preferably, 0.5 to 1.5 mol equivs (relative to Fmoc amino acid) of coupling reagent(s) is used with 1.5 to 2.5 mol equivs (relative to Fmoc amino acid) of DIEA in 5 to 7 vols of DMF for 60 minutes at 15 to 30° C.

A preferred embodiment of the process of the present invention with the successive steps (a) to (j) as defined above, is characterized in that, in step (g), the resin is washed after each coupling, 2 to 4 times with 7 to 12 vols of DMF for up to 5 minutes; and in a more preferred embodiment, the resin after each coupling is washed 2 times with 10 vols DMF for up to 5 minutes.

A preferred embodiment of the process of the present invention with the successive steps (a) to (j) as defined above, is characterized in that, in step (i):
the resin is immersed in the cleavage cocktail and agitated for 2 to 3 hours at an ambient temperature, and more preferably the resin is immersed and agitated for 2.5 hours, and
the resin/cleavage cocktail solution are intermittently sparged with nitrogen gas.

A preferred embodiment of the process of the present invention with the successive steps (a) to (j) as defined above is characterized in that, in step (j):
the spent resin is washed with a small volume of either fresh cleavage cocktail or TFA/DCM (20:80 v/v) 1 to 2 times;
the spent resin is optionally washed with a small volume of MeOH.

A preferred embodiment of the process of the present invention with the successive steps (a) to (j) as defined above, is characterized in that, in step (k), after combining the filtrates and evaporating the combination:
the crude peptide is precipitated out using 5 to 15 vols MtBE;
the precipitated peptide is dried to the required level of dryness;

the precipitated peptide is dissolved with dilute acid, or dilute acid with the organic modifier to be used in downstream chromatographic purification
the peptide is purified and a salt exchange step using reverse-phase preparative chromatography is performed.

Another preferred embodiment of the process of the present invention is characterized in that it comprises the following successive steps (a) to (j):
(a) swelling the Fmoc-Sieber-Amide resin using 1 to 3 treatments of 7 to 12 vols of DMF for up to 1 hour, even more preferred, 3 treatments of 10 vols of DMF lasting 10 to 30 minutes per treatment;
(b) de-protecting the Fmoc group on the Sieber resin using 1 to 2 treatments with a solution of piperidine in DMF (10-20% v/v) lasting 5 to 20 minutes, even more preferrably 2 treatments of 15% v/v piperidine in DMF lasting 10 minutes;
(c) washing the de-protected resin is 3 to 5 times with 7 to 12 vols of DMF each wash lasting up to 5 minutes, even more preferably, 3 washes with 10 vols DMF each wash lasting up to 5 minutes.
(d) activating 1.2-2.0 mol equivs (relative to the resin-batch scale) of the Fmoc-amino acid for coupling to the de-protected resin by dissolving the Fmoc-amino acid and coupling reagent(s) in DMF, adding DIEA, stirring for 1 to 2 minutes; and more preferably activating 1.5 mol equivs (relative to the resin-batch scale) of the Fmoc-amino acid for coupling by dissolving the Fmoc-amino acid and coupling reagent(s) in DMF, adding DIEA, stirring for 1 to 2 minutes.
(e) charging the activated Fmoc-amino acid solution to the resin in the reactor;
(f) coupling the Fmoc-amino acid to the deprotected resin by immersing and agitating the deprotected resin with the activated Fmoc-amino acid solution for 30-120 min at ambient temperature; said activated Fmoc-amino acid solution comprised of Fmoc-amino acid as described in (d) above along with 0.5 to 1.5 mol equivs (relative to Fmoc amino acid) of coupling reagent(s) with 1.5 to 2.5 mol equivs (relative to Fmoc amino acid) of DIEA in 4 to 10 vols DMF at ambient temperature; and more preferably, 0.5 to 1.5 mol equivs (relative to Fmoc amino acid) of coupling reagent(s) with 1.5 to 2.5 mol equivs (relative to Fmoc amino acid) of DIEA in 5 to 7 vols of DMF for 60 minutes at 15 to 30° C.
(g) washing the resin after each coupling, 2 to 4 times with 7 to 12 vols of DMF for up to 5 minutes; and more preferably 2 times with 10 vols DMF for up to 5 minutes;
(h) repeating steps (b)-(g) until a peptide is formed;
(i) cleaving the desired peptide from the resin while simultaneously de-protecting the amino acid side chains using a cleavage cocktail, by:
immersing the resin in cleavage cocktail and agitating for 2 to 3 hours at an ambient temperature, and more preferably by immersing and agitating for 2.5 hours, and
sparging the resin/cleavage cocktail mixture intermittently with nitrogen gas.
(j) filtering the cleavage mixture from the resin, then washing the spent resin with a small volume of either fresh cleavage cocktail or TFA/DCM (20:80 v/v) 1 to 2 times; and
optionally washing the spent resin with a small volume of MeOH.

(k) combining the filtrate and washes and evaporating the combination, then
  precipitating the crude peptide from the combined evaporated filtrate and washes using 5 to 15 vols MtBE;
  drying the precipitated peptide to the required level of dryness;
  dissolving the precipitated peptide with dilute acid, or dilute acid with the organic modifier to be used in downstream chromatographic purification;
  purifying the peptides and performing a salt exchange step using reverse-phase preparative chromatography.

A preferred embodiment of any one of the immediately foregoing aspects of the present invention is characterized in that steps (a) to (j) (new substeps are indicated by -#) are further defined as follows:

(a) swelling the Fmoc-Sieber-Amide resin initially using 1 to 3 treatments of 7 to 12 vols of DMF for up to 1 hour, even more preferred, 3 treatments of 10 vols of DMF lasting 10 to 30 minutes per treatment;

(b) de-protecting the Fmoc group on the Sieber resin using 1 to 2 treatments with a solution of piperidine in DMF (10-20% v/v) lasting 5 to 20 minutes, even more preferred 2 treatments of 15% v/v piperidine in DMF lasting 10 minutes;

(c) washing the de-protected resin 3 to 5 times with 7 to 12 vols of DMF each wash lasting up to 5 minutes, even more preferred, 3 washes with 10 vols DMF each wash lasting up to 5 minutes;

(d) activating the Fmoc-amino acids (1.2-2.0 mol equivs, or more preferred, 1.5 mol equivs relative to the resin-batch scale) for coupling by dissolving the Fmoc-amino acid and coupling reagent(s) in DMF, adding DIEA, stirring for up to 5 minutes, even more preferred, stirring for 1 to 2 minutes;

(e) charging the coupling solution to the resin in the reactor;

(f) using 0.5 to 1.5 mol equivs of coupling reagent(s) relative to Fmoc amino acid with 1.5 to 2.5 mol equivs of DIEA relative to the Fmoc-amino acids in 4 to 10 vols DMF for 30 to 120 minutes at ambient temperature, even more preferred, using 5 to 7 vols of DMF for 60 minutes at 15 to 30° C.;

(g). washing the resin, after each coupling, 2 to 4 times with 7 to 12 vols of DMF for up to 5 minutes, even more preferred, 2 washes with 10 vols of DMF for up to 5 minutes;

(h). repeating steps (b)-(g) until a peptide is formed;

(i). immersing the resin in the cleavage cocktail and agitating for 2 to 3 hours at an ambient temperature, more preferred immersing and agitating the resin for 2.5 hours;

(i-1). sparging the resin/cleavage cocktail solution with nitrogen gas intermittently;

(j). filtering the cleavage mixture from the resin;

(j-1). washing the spent resin with a small volume of either fresh cleavage cocktail or TFA/DCM (20:80 v/v) 1 to 2 times;

(j-2). washing the spent resin with a small volume of MeOH;

(k). combining the filtrates and evaporating the combination (k-1) precipitating a crude peptide out using 5 to 15 vols MtBE;

(k-2). drying the precipitated peptide to the required level of dryness (k-3) dissolving the precipitated peptide with dilute acid, or dilute acid with the organic modifier to be used in downstream chromatographic purification (k-4). purifying the peptide and performing a salt exchange step using reverse-phase preparative chromatography.

It is acknowledged that some protecting groups (e.g. 2,2,4,6,7-pentamethyldihydrobenzofuran-5-sulfonyl (Pbf) side chain protection of Arg) will require a higher percentage of acid, typically 50-80%, for removal of the side chain protecting group within a practical timeframe, however, all other aspects of the present invention remain the same. Other side chain protecting groups contemplated, include but are not limited- to, methoxytrimethylbenzene sulfonyl (Mtr), 2,2,5,7,8-pentamethyl-chroman-6-sulfonyl chloride (Pmc), 4,4-dimethyloxybenhydryl (Mbh) and 2,4,6-trimehoxybenzyl (Tmob).

The present invention also provides for those situations when it is desirable to retain certain side chain protecting groups during and after cleavage. For instance, it is important to retain the acetamidomethyl (Acm) side chain protecting group on Cys so that the completed peptide can be purified in its linear form and thereafter cyclized when the protecting groups are removed and a disulfide bridge is formed between two Cys residues.

Figure 1:
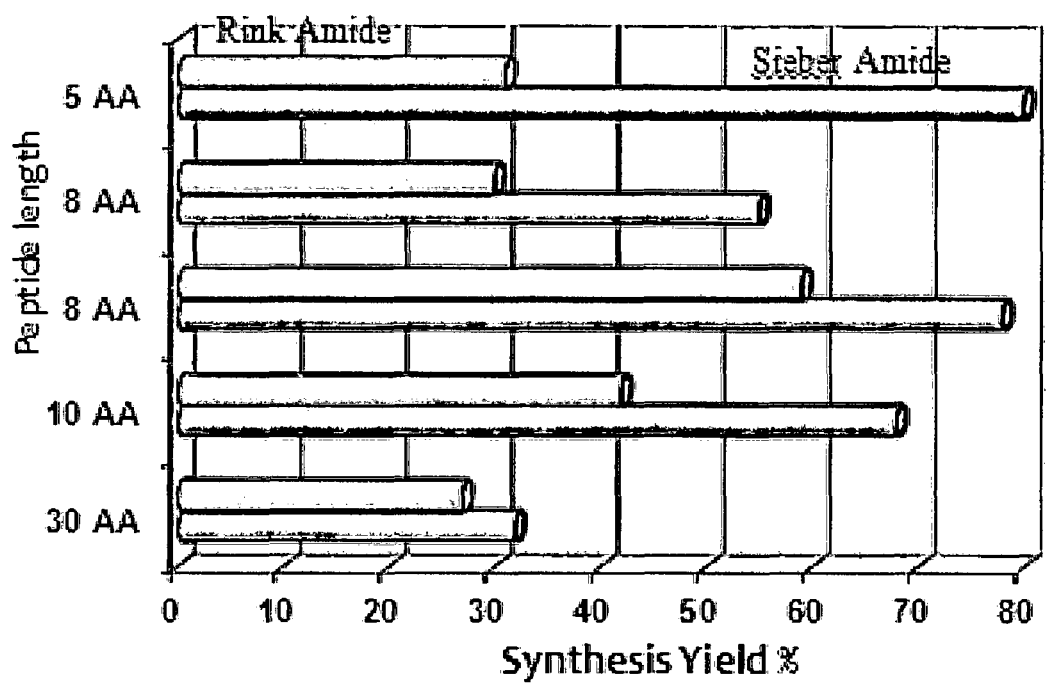
FIG. 1: graph depicting the head to head comparison of peptides synthesized using a Rink Amide resin to those synthesized using a Sieber Amide resin under similar synthetic procedures. Peptides of varying lengths from 5 amino acids to 30 amino acids were made, according to the procedures described herein, and the synthetic yield was measured. For each peptide length (reported down the y-axis of the graph), the percent yield (as indicated by the x-axis) using Rink Amide resin is represented by the top bar and the percent yield using Sieber Amide resin is represented by the bottom bar. For each peptide synthesized, i.e. a 5 amino acid sequence, two 8 amino acid sequences, an 8 amino acid sequence modified with one or more dopamine moieties and a 30 amino acid sequence, use of Sieber Amide resin resulted in higher % yields.

Most stepwise solid-phase synthesis requires use of a polystyrene resin for synthesis of peptide amides. Rink amide resins are used in solid phase peptide synthesis to prepare peptide amides utilizing Fmoc-protected amino acids. Coupling of the first amino acid can be achieved using typical methods of amide bond formation. The peptide sequence is assembled under basic or neutral conditions on Rink amide resin then the completed peptide is cleaved from the resin under acid conditions. Typically the peptide is cleaved from Rink Amide resin using greater than 80% TFA v/v. (Stathopoulos, P.; Papas, S.; and Tsikaris, V., *J. Pept. Sci.*, 2006, 12:227-37). Stronger acids or higher concentrations of TFA sometimes cleaves some of the Rink linker from the polystyrene support and introduces colored impurities into the cleaved product. As such for some peptides, the synthesis yield using Rink Amide resin is traditionally low. Examples of Rink resins are:

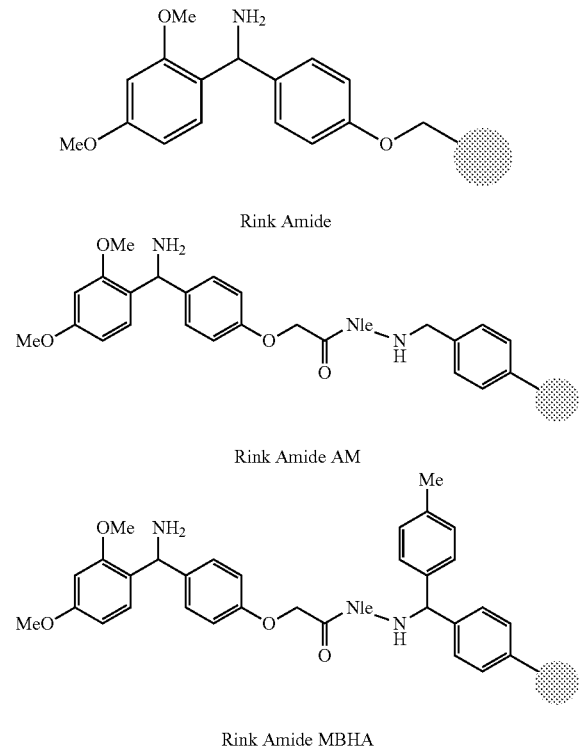

Rink Amide

Rink Amide AM

Rink Amide MBHA

The lability of the linker of "super acid-sensitive" or "hyper acid-sensitive" resin to low concentrations of acid allows for fully-protected peptides to be released from the resin. Typically, 1-5% v/v TFA is required for peptide cleavage. With the exception of the decreased potency of the acid required for cleavage, these resins are similar to the Rink Amide resins, namely they are a polystyrene matrix of similar bead size with similar loading capacity. As such, these resins are useful for convergent synthesis employing the same Fmoc chemistry with respect to loading of the first and coupling of subsequent residues.

Sieber Amide resin, an example of the "super acid-sensitive" resins (Sieber, P., *Tetrahedron Lett.*, 1987, 28(19): 2107-10), is primarily used for the synthesis of peptide amides retaining side chain protecting groups including, but not limited to, tert-butyloxycarbonyl (Boc) and tert-butyl ether (tBu) when used with low concentrations of trifluoroacetic acid (TFA) (1-5% v/v) in the cleavage cocktail.

Since Sieber Amide resin is traditionally used for Fmoc solid-phase synthesis, it is necessary that the amino acids be Fmoc-protected. Accordingly, the protecting groups that remain after completion of the peptide synthesis need to be cleaved. The cleavage of the remaining protecting groups requires high acidolytic conditions, such as up to 95% TFA containing up to 5% ethanediol and up to 5% 4-(methylmercapto)phenol (Sieber, P., *Tetrahedron Lett.*, 1987, 28(19): 2107-10).

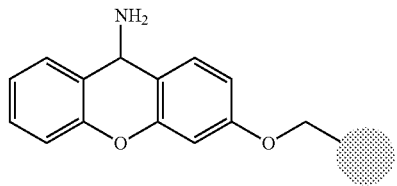

Sieber Amide Resin

The Inventors attempted the synthesis of an acid sensitive 8-residue peptide amide using Sieber Amide resin. They found that linear SPPS could be done using Sieber Amide resin together with Fmoc chemistry. The Inventors discovered that by adjusting the conditions, a high concentration of acid, i.e. TFA, is not required for cleavage of the final product from the Sieber resin. In addition, it was discovered that side chain protecting groups could be removed concurrently with a cleavage of the resulting peptide from the Sieber Amide resin when a "medium" strength TFA/TIPS/DCM cleavage cocktail is used. With some optimization, the Inventors discovered that it was possible to synthesize full-length peptides with protected amino acids, particularly those with Boc, tBu and/or Trt protecting groups, and then release a fully de-protected peptide amide from the resin while minimizing peptide degradation.

Figure 2:
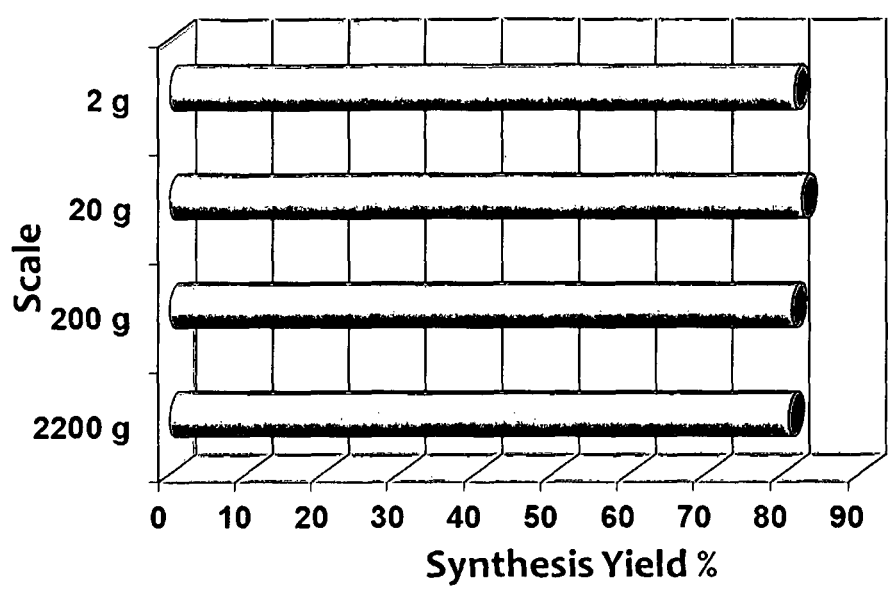
FIG. 2: graph depicting the synthesis yield reproducibility on a 2 g to 2200 g scale when using Sieber Amide resin for the synthesis of a 5 amino acid peptide. As reported, a synthesis yield of about 80% was consistently achieved for every scale.
Figure 3:
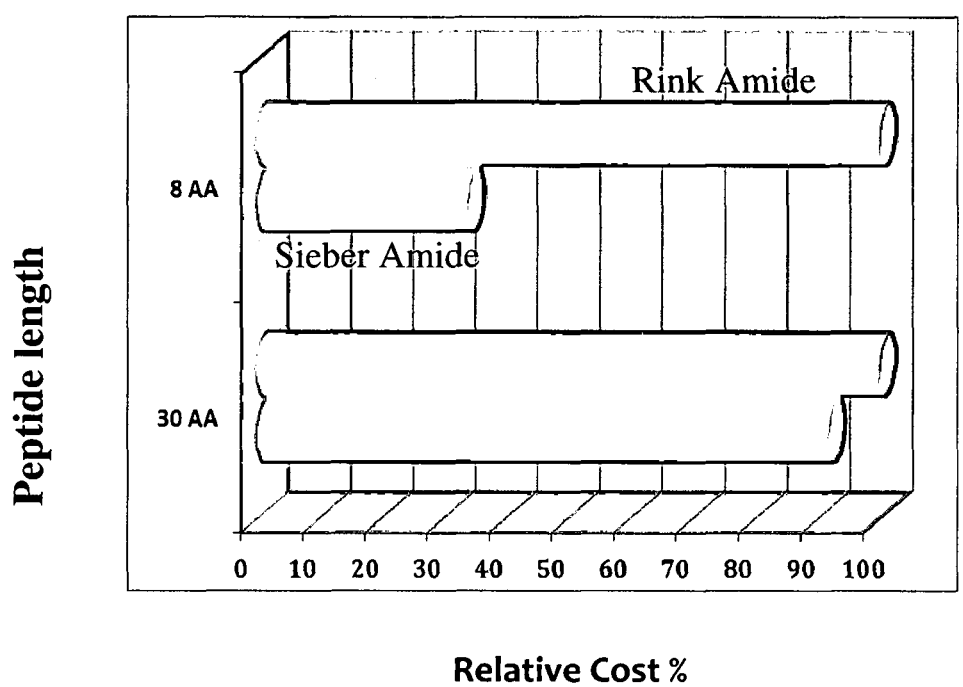
FIG. 3: graph depicting the relative cost based on material employed for the synthesis of an 8 amino acid peptide and a 30 amino acid peptide using a Rink Amide resin versus Sieber Amide resin. The relative cost based on materials used for those peptides synthesized using a Rink Amide resin for a 8 amino acid peptide and 30 amino acid peptide are represented by the top bars whereas the relative cost for the same peptide using a Sieber Amide resin are represented by the bottom bars for each peptide. As reported, the relative cost of using a Sieber Amide resin is less than that of a Rink Amide resin.

The Inventors also attempted to use Sieber Amide resin to synthesize other peptides from 5 to 30 amino acids in length and peptides containing unnatural amino acids as well troublesome naturally-occurring amino acids such as tryptophan, cysteine and arginine. The Inventors discovered that peptides containing unnatural or problematic amino acids could be synthesized using Sieber Amide resin with medium TFA concentration during cleavage. It was also discovered that peptides containing arginine could be synthesized using Sieber Amide resin although higher TFA concentration was necessary during cleavage particularly if sulfonyl side chain protecting groups are present Surprisingly, Sieber Amide resin, when used in a manner contrary to that disclosed in the literature, resulted in higher yields of purer crude product. For example, the Inventors discovered that the synthesis yield increased from 18-30% when Rink Amide resin was used, to 78-83% when Sieber Amide resin was used for the preparation of the ghrelin analogue H-Inp-D-Bal-D-Trp-Phe-Apc-$NH_2$, as reported in WO 2004/014415. For other peptides, such as dopamine-somatostatin chimeras, the Inventors reported that synthesis yield using the Sieber Amide resin was 72.6 to 80.8% compared to commonly used resins such as the Rink Amide family of resins (e.g. Rink Amide MBHA resin, Rink Amide AM resin, Rink Amide resin) yielding 13 to 71% under identical conditions. The inventors discovered that by using Sieber Amide resin increased yield on average by up to 50% compared to using Rink Amide resin. Further, yield was reproducible between batches and on scale-up from 2 g up to 2.2 kg. The comparative yields using Rink Amide versus using Sieber Amide resin under identical conditions to synthesize peptides of varying lengths, i.e. 5 amino acids in length to 30 amino acids in length, are reported in FIG. 1. In each comparison, use of Sieber Amide resin resulted in higher synthesis yields, 70% versus 10%. As a result, relative cost percentage, based on peptide length, was less when Sieber Amide resin is use in place of the traditional Rink Amide resin FIG. 3. The Inventors also demonstrate the reproducibility of synthesis yield using Sieber Amide resin in FIG. 2.

Further, commonly-used Rink Amide resins require high concentrations of TFA, usually 80-95% v/v, for cleavage of the final peptide from the resin. The Inventors discovered that by using Sieber Amide resin, only 10-25% TFA was required. As stated previously, higher concentrations of TFA can result in serious degradation of the peptide over time, as well as the presence of impurities such as those derived from the attachment of all or part of the resin linker to the peptide which subsequently may be difficult to remove. Moreover, work-up after cleavage is faster using the claimed process since less acid is needed during final cleavage In addition, it was found that it was possible to reduce quantities of Fmoc-amino acids, coupling reagents, and solvents using Sieber Amide resin, without affecting yield or purity of the peptide produced Certain amino acids present in compounds of the invention are represented herein as follows:

A3c 1-amino-1-cyclopropanecarboxylic acid
A4c 1-amino-1-cyclobutanecarboxylic acid
A5c 1-amino-1-cyclopentanecarboxylic acid
A6c 1-amino-1-cyclohexanecarboxylic acid
Abu α-aminobutyric acid
Acc 1-amino-1-cyclo($C_3$-$C_9$)alkyl carboxylic acid
Act 4-amino-4-carboxytetrahydropyran, i.e.:

Aepa 4-(2-aminoethyl)-1-carboxy methyl-piperazine, represented by the structure:

Aib α-aminoisobutyric acid
Ala or A alanine
β-Ala beta-alanine
Apc amino piperidinylcarboxylic acid, i.e.:

Arg or R arginine
hArg homoarginine
Asn or N asparagine
Asp or D aspartic acid

Bal 3-benzothienylalanine, i.e.:

Bip 4,4'-biphenylalanine, i.e.:

Bpa 4-benzoylphenylalanine, i.e.:

Caeg N-(2-aminoethyl)-N-(2-cytosinyl-1-oxo-ethyl)-glycine, represented by the structure:

Cha β-cyclohexylalanine;
Cys or C cysteine;
Dab 2,4-diaminobutyric acid, (α,γ-diaminobutyric acid);
Dap 2,3-diaminopropionic acid, (α,β-diaminopropionic acid);

Dip β,β-diphenylalanine, i.e.:

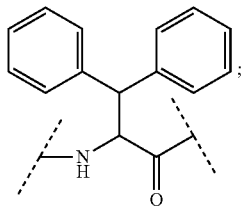

Dhp 3,4-dehydroproline
Dmt 5,5-dimethylthiazolidine-4-carboxylic acid
2-Fua β-(2-furyl)-alanine, i.e.:

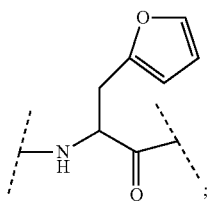

Gln or Q glutamine
Glu or E glutamic acid
Gly or G glycine
His or H histidine
3-Hyp trans-3-hydroxy-L-proline, i.e., (2S,3S)-3-hydroxypyrrolidine-2-carboxylic acid;
4-Hyp 4-hydroxyproline, i.e., (2S,4R)-4-hydroxypyrrolidine-2-carboxylic acid;
Ile or I isoleucine
Inc indoline-2-carboxylic acid
Inp isonipecotic acid, i.e.:

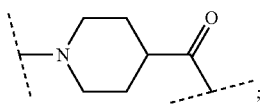

Ktp 4-ketoproline
Leu or L leucine
hLeu homoleucine
Lys or K lysine
Lys(Ac) lysine(acetyl)
Met or M methionine
1-Nal β-(1-naphthyl)alanine:
2-Nal β-(2-naphthyl)alanine;
Nle norleucine
Nva norvaline
Oic octahydroindole-2-carboxylic acid
Orn ornithine
2-Pal β-(2-pyridyl)-alanine, i.e.,

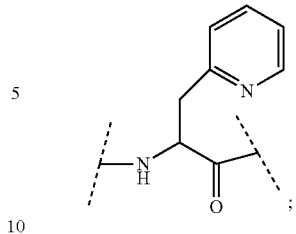

3-Pal β-(3-pyridyl)-alanine, i.e.:

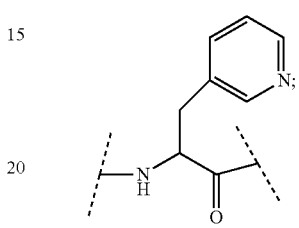

4-Pal β-(4-pyridyl)-alanine, i.e.:

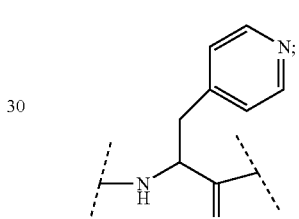

Pff pentafluorophenylalanine, i.e.

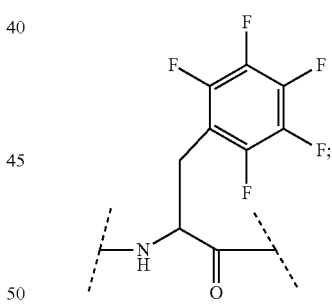

Phe or F phenylalanine
hPhe homophenylalanine
Pim 2'-(4-phenyl)imidazolyl, i.e.:

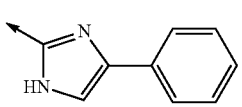

Pip pipecolic acid
Pro or P proline
Ser or S serine
Ser(Bzl) serine(O-benzyl)
Taz β-(4-thiazolyl)alanine, i.e.,

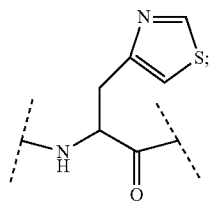

2-Thi β-(2-thienyl)alanine, i.e.:

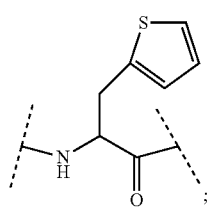

3-Thi β-(3-thienyl)alanine, i.e.:

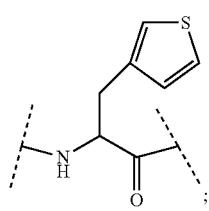

Thr or T threonine
Thr(Bzl) threonine(O-benzyl)
Thz thiazolidine-4-carboxylic acid
Tic 1,2,3,4-tetrahydroisoquinoline-3-carboxylic acid
Tle tert-leucine
Trp or W tryptophan
(N-Me)D-Trp N$^\alpha$-methyl-D-tryptophan
Tyr or Y tyrosine
3-I-Tyr 3-iodo-tyrosine
Val or V valine
Dop1" is meant a compound having the structure of:

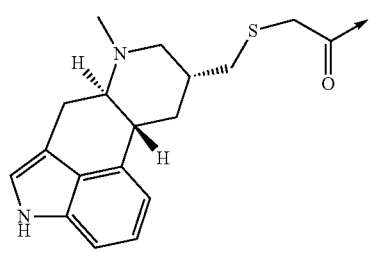

"Dop2" is meant a compound having the structure of:

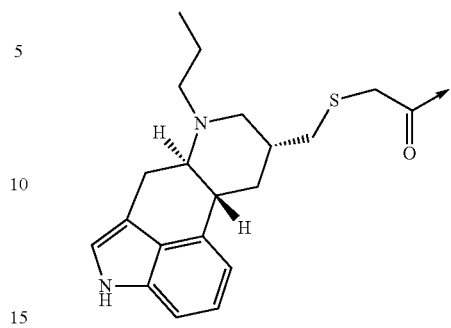

"Dop3" is meant a compound having the structure of:

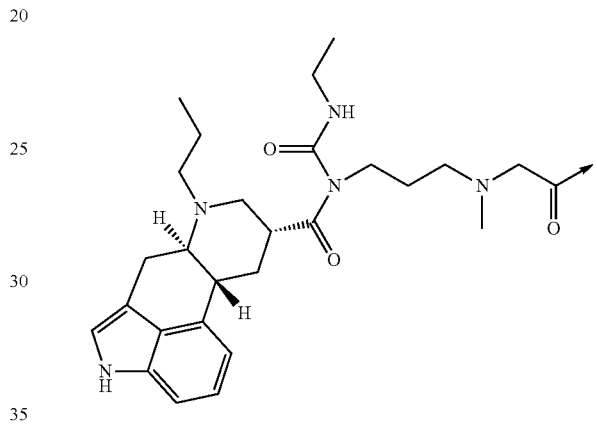

"Dop4" is meant a compound having the structure of:

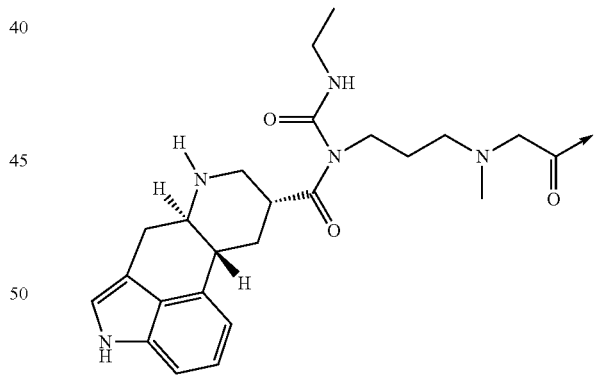

"Dop5" is meant a compound having the structure of:

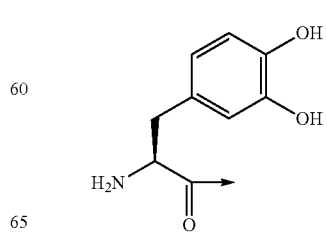

"Dop6" is meant a compound having the structure of:

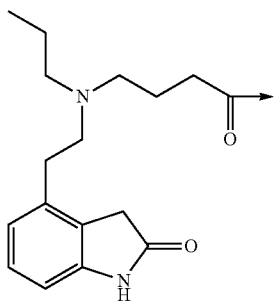

"Dop7" is meant a compound having the structure of:

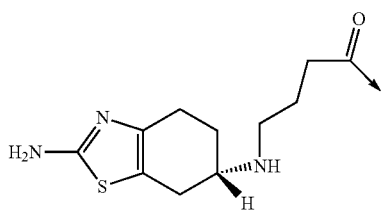

"Dop8" is meant a compound having the structure of:

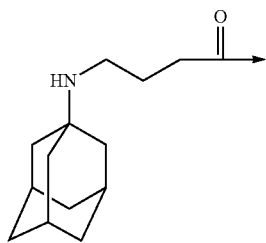

"Dop9" is meant a compound having the structure of:

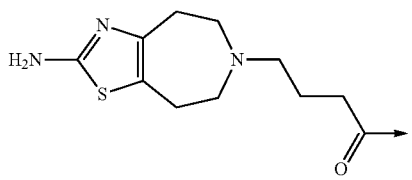

"Dop10" is meant a compound having the structure of:

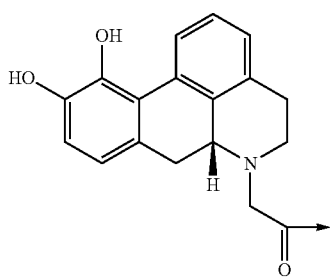

"Dop11" is meant a compound having the structure of:

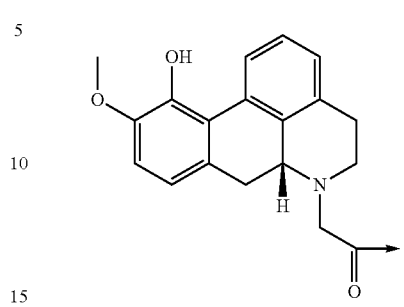

"Dop12" is meant a compound having the structure of:

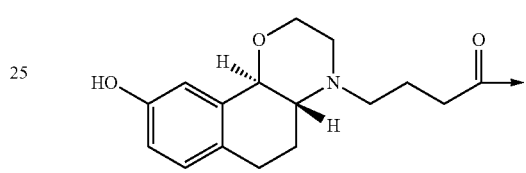

"Dop13" is meant a compound having the structure of:

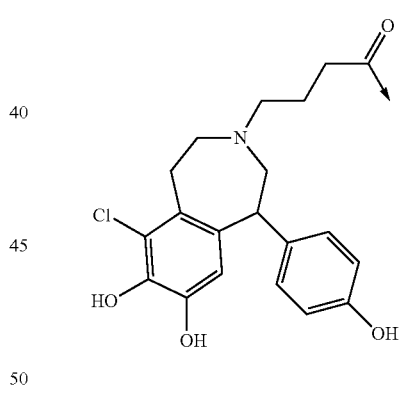

Lys(Dop2) has the structure of:

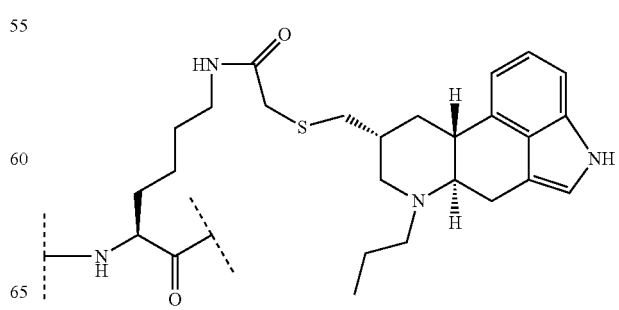

Dop2-Lys(Dop2) has the structure of:

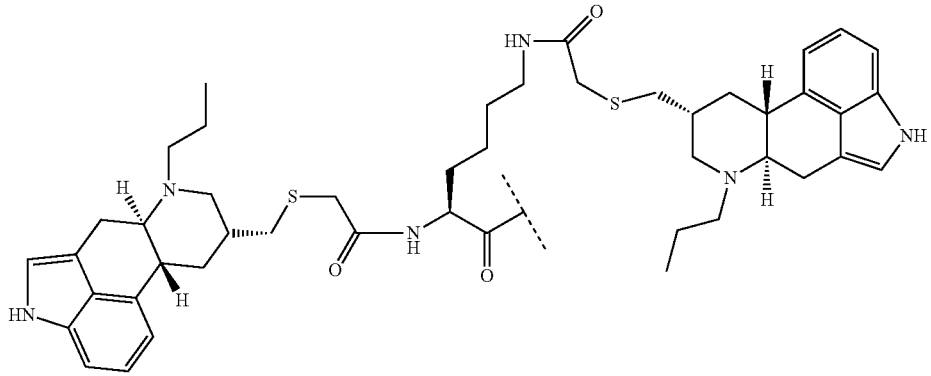

Lys(Dop5) has the structure of:

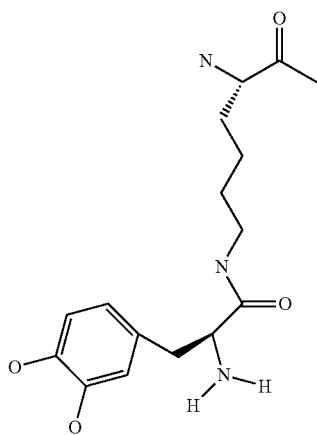 [SMILES: CC(=O)[C@@H](N)CCCCNC(=O)[C@@H](N)Cc1ccc(O)c(O)c1]

Dop5-Lys(Dop5) has the structure of:

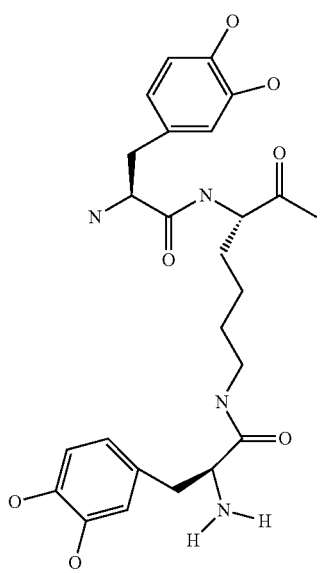 [SMILES: CC(=O)[C@H](CCCCNC(=O)[C@@H](N)Cc1ccc(O)c(O)c1)NC(=O)[C@@H](N)Cc1ccc(O)c(O)c1]

The Greek letter psi "Ψ" is used herein to indicate that a peptide bond has been replaced by a pseudopeptide bond. In an amino acid sequence name, the format of the Ψ term is $A^1$-Ψ-(X—X')$A^2$ wherein $A^1$ is the amino acyl radical whose carbonyl group has been modified to X and $A^2$ is the amino acyl radical whose α-amino group has been modified to X'. X and X' are shown as strings of element symbols separated by a bond, e.g., Tyr-Ψ-($CH_2$—NH)Gly.

The application employs the following abbreviations:
Ac acetyl
ACN acetonitrile
Acm acetamidomethyl
AM aminomethyl
Boc tert-butyloxycarbonyl
DCE dichloroethane
DCM dichloromethane
DIC N,N'-diisopropylcarbodiimide
DIEA N,N-diisopropylethylamine
DMF N,N-dimethylformamide
DTT dithiothreitol
EDT ethanedithiol
Fmoc 9-Fluorenylmethyloxycarbonyl
HATU O-(7-azabenzotriazol-1-yl)-1,1,3,3-tetramethyluronium hexafluorophosphate (or N-[(dimethylaminio)-1H-1,2,3-triazolo-[4,5-b]pyridin-1-yl-methylene]-N-methylmethanaminium hexafluorophosphate N-oxide)
HBTU 2-(1H-benzotriazol-1-yl)-1,1,3,3-tetramethyluronium hexafluorophosphate (or N-[(1H-benzotriazol-1-yl)-(dimethylamino)methylene]-N-methylmethanaminium hexafluorophosphate N-oxide)
HCTU (2-(6-chloro-1H-benzotriazole-1-yl)-1,1,3,3-tetramethylaminium hexafluorophosphate) (or N-[(1H-6-chloro-benzotriazol-1-yl)-(dimethylamino)methylene]-N-methylmethanaminium hexafluorophosphate N-oxide)
HOAt 1-hydroxy-7-azabenzotriazole
HOBt 1-hydroxybenzotriazole
HPLC high pressure liquid chromatography
LOD loss on drying
Mbh 4,4-dimethyloxybenzhydryl
MBHA 4-methylbenzhydrylamine
MtBE methyl tert-butyl ether
Mtr methoxytrimethylbenzene sulfonyl
OtBu tert-butyl ester
Pbf 2,2,4,6,7-pentamethyldihydrobenzofuran-5-sulfonyl
PEG polyethylene glycol
Pmc 2,2,5,7,8-pentamethylchroman-6-sulfonyl chloride
TBTU 2-(1H-benzotriazole-1-yl)-1,1,3,3-tetramethyluronium tetrafluoroborate (or N-[(1H-benzotriazol-1-yl)-(dimethylamino)methylene]-N-methylmethanaminium tetrafluoroborate N-oxide)

tBu tert-butyl ether
TES triethylsilane
TFA trifluoroacetic acid
TIPS triisopropylsilane
Tmob 2,4,6-trimethoxybenzyl
Trt trityl or triphenylmethyl Unless otherwise indicated, the following definitions are set forth to illustrate and define the meaning and scope of the various terms used to describe the invention herein.

The term "cleavage cocktail" as used herein refer to a mixture of reagents used to remove, or cleave, the assembled peptide from a resin. In addition, a cleavage cocktail also serves to remove all side chain protecting groups and the N-terminal protecting groups.

The term "about" (or "approximately") as used herein in association with parameters or amounts, means that the parameter or amount is within +5% of the stated parameter or amount. For instance, "about 20%" means (20±20*0.05)% which is equal to (20±0.1)%.

The term "resin," as used hereafter, refers to either Fmoc-Sieber Amide resin or Sieber Amide resin to which one or more amino acids have been attached.

The term "room temperature" (or ambient temperature) means a temperature range of from 15-30° C.

The following example is described for purposes of illustrating a method of the present invention and is not to be construed to limit the present invention in any way.

The Invention describes a novel method of synthesizing a peptide comprising step-wise solid-phase chemistry.

In a preferred embodiment, the present invention relates to a process for the synthesis of a therapeutic peptide wherein said peptide is selected from an analogue of somatostatin, bombesin, VIP, PACAP, GHRH, glucagon, calcitonin, peptide YY, neuromedin B, PTH, PTHrP, PTH2, GLP-1, Urotensin-II, ghrelin, melanocortin, MIS, LHRH, adropin, GIP, neuropeptide Y, IGF-1, dopamine-somatostatin chimeras, and ACTH.

In a more preferred embodiment, the present invention relates to a process for the synthesis of a therapeutic peptide wherein said peptide is selected from an analogue of ghrelin or dopamine-somatostatin chimeras.

In a more preferred embodiment, the present invention relates to a process for the synthesis of a therapeutic peptide wherein said peptide is selected from an analogue of ghrelin.

In a more preferred embodiment, the present invention relates to a process for the synthesis of a therapeutic peptide wherein said peptide is selected from an analogue of ghrelin of the formula (I)

$$R^1-A^1-A^2-A^3-A^4-A^5-R^2 \quad (I)$$

wherein
$A^1$ is Aib, Apc or Inp;
$A^2$ is D-Bal, D-Bip, D-Bpa, D-Dip, D-1Nal, D-2Nal, D-Ser(Bzl), or D-Trp;
$A^3$ is D-Bal, D-Bip, D-Bpa, D-Dip, D-1 Nal, D-2Nal, D-Ser(Bzl), or D-Trp;
$A^4$ is 2Fua, Orn, 2Pal, 3Pal, 4Pal, Pff, Phe, Pim, Taz, 2Thi, 3Thi, Thr(Bzl);
$A^5$ is Apc, Dab, Dap, Lys, Orn, or deleted;
$R^1$ is hydrogen; and
$R^2$ is OH or NH;
provided that
when $A^5$ is Dab, Dap, Lys, or Orn, then:
$A^2$ is D-Bip, D-Bpa, D-Dip or D-Bal; or
$A^3$ is D-Bip, D-Bpa, D-Dip or D-Bal; or
$A^4$ is 2Thi, 3Thi, Taz, 2Fua, 2Pal, 3Pal, 4Pal, Orn, Thr(Bzl), or Pff;

when $A^5$ is deleted, then:
$A^3$ is D-Bip, D-Bpa, or D-Dip; or
$A^4$ is 2Fua, Pff, Taz, or Thr(Bzl); or
$A^1$ is Apc and -
$A^2$ is D-Bip, D-Bpa, D-Dip or D-Bal; or
$A^3$ is D-Bip, D-Bpa, D-Dip or D-Bal; or
$A^4$ is 2Thi, 3Thi, Orn, 2Pal, 3Pal, or 4Pal;
and more particularly compound of formula (I) wherein
$A^1$ is Aib, Apc or Inp;
$A^2$ is D-Bal, D-Bip, D-Bpa, D-Dip, D-1 Nal, D-2Nal, D-Ser(Bzl), or D-Trp;
$A^3$ is D-Bal, D-Bpa, D-Dip, D-1 Nal, D-2Nal, or D-Trp;
$A^4$ is Orn, 3Pal, 4Pal, Pff, Phe, Pim, Taz, 2Thi, or Thr(Bzl); and
$A^5$ is Apc, Lys, or deleted.

In a more preferred embodiment, the present invention relates to a process for the synthesis of a therapeutic peptide wherein said peptide is an analogue of ghrelin of formula (I) as defined above wherein
$A^1$ is Apc or Inp;
$A^2$ is D-Bal, D-Bip, D-1 Nal, or D-2Nal;
$A^3$ is D-Bal, D-1 Nal, D-2Nal, or D-Trp;
$A^4$ is 3Pal, 4Pal, Pff, Phe, Pim, Taz, 2Thi, or Thr(Bzl); and
$A^5$ is Apc or Lys.

In a more preferred embodiment, the present invention relates to a process for the synthesis of a therapeutic peptide wherein said peptide is an analogue of ghrelin selected from H-Inp-D-Bal-D-Trp-Phe-Apc-NH$_2$, H-Inp-D-2B al-D-Trp-Phe-Apc-NH$_2$, H-Inp-D-Bal-D-Trp-2Thi-Apc-NH$_2$, and H-Inp-D-Bal-D-Trp-Taz-Apc-NH$_2$, and more particularly H-Inp-D-Bal-D-Trp-Phe-Apc-NH$_2$.

In a more preferred embodiment, the present invention relates to a process for the synthesis of a therapeutic peptide wherein said peptide is an analogue of dopamine-somatostatin chimeras, i.e. a chimeric molecule comprising somatostatin or an analogue thereof and at least one dopamine moiety.

In a more preferred embodiment, the present invention relates to a process for the synthesis of a therapeutic peptide wherein said peptide is an analogue of dopamine-somatostatin chimeras including the structure of Dop A or DopA-Lys (DopA), wherein Lys is L-Lysine, unless expressly designated as D-Lys, A is 1-13, for example Dop1, Dop2, Dop3, Dop4, Dop5, Dop6, Dop7, Dop8, Dop9, Dop10, Dop11, Dop12, Dop13. In another more preferred embodiment, the present invention relates to a process for the synthesis of a therapeutic peptide wherein said peptide is an analogue of dopamine-somatostatin chimeras including the structure of DopA-Lys(DopA), and the compound Dop2-D-Lys(Dop2)-c[Cys-Tyr-D-Trp-Lys-Abu-Cys]-Thr-NH$_2$.

The general procedure for the synthesis of a fully deprotected therapeutic peptide amide according to the process of the present invention is illustrated below.

Fmoc-Sieber Amide resin (Merck Chemicals, Darmstadt, Germany) is initially swelled using 1 to 3 treatments of 7 to 12 vols, 10 vols preferred, of DMF (Samsung, Korea), in addition, for up to 1 hour, although 3 treatments lasting about 10-30 minutes each are preferred.

Fmoc de-protection of the Sieber Amide resin is accomplished using 1 to 2 treatments of a solution of piperidine in DMF (about 10-20% v/v, 15% v/v preferred) lasting 5 to 20 minutes, although 2 treatments lasting 10 minutes each are preferred.

The de-protected resin is washed 3 to 5 times with 7 to 12 vols of DMF lasting for up to 5 minutes, although 3 washes of 10 vols of DMF lasting up to 5 minutes for each wash is preferred.

The Fmoc-amino acids are activated for coupling to the resin by dissolving the Fmoc-amino acid together with the coupling reagent(s) in DMF, adding a base such as DIEA (SAFC, Gillingham, United Kingdom), stirring for up to 5 minutes (1-2 minutes preferred), and charging to the resin in the reactor.

Fmoc-amino acid coupling are carried out using about 1.2 to 2.0 mol equivs (1.5 mol equivs preferred) of Fmoc-amino acid relative to the resin using HCTU (Merck Chemicals) or TBTU/HOBt (0.5 to 2.0 mol equivs relative to the Fmoc amino acid) (both TBTU and HOBt obtained from SAFC) with a base, preferably DIEA (about 1.5 to 3.5 mol equivs relative to the Fmoc-amino acid, although specific equivs are preferred for particular amino acids), in DMF (4 to 10 vols, 5 to 7 vols preferred) lasting 30 to 120 minutes (although duration varies depending on the amino acid being coupled, however, 60 minutes is preferred for most amino acids) at an ambient temperature (preferably 15 to 30° C.). Either HCTU (1.2 equivs relative to the Fmoc-amino acid) or TBTU with HOBt (0.98 mol equivs) are preferred depending on the amino acid being coupled.

After each Fmoc-amino acid coupling, the resin is washed 2 to 4 times with 7 to 12 vols of DMF (2 washed of 10 vols of DMF is preferred) each washing lasting up to 5 minutes.

The desired peptide is cleaved from the resin and any side chain protecting groups are "de-protected" using a cleavage cocktail consisting of about 15 to 25% v/v TFA (Rhodia, Lyon, France) (although preferably 15 to 20% v/v, and approximately 20% v/v is more preferred) with about 2.5 to 12% v/v TIPS (SAFC, Gillingham, United Kingdom) (although preferably 5-10% v/v, and about 10% v/v is more preferred) used as a scavenger with the remainder of the cleavage cocktail comprising 62.5 to 82.5% v/v DCM (INEOS Chlor, Runcorn, UK) (depending on the percentage of TFA and TIPS used). The resin is immersed in and agitated with the cleavage cocktail for 2 to 3 hours (2.5 hours preferred) at about ambient temperature (about 15 to 30° C.). Intermittent sparging with nitrogen gas or blanketing the cleavage reaction mixture with nitrogen gas is introduced. The cleavage mixture containing the desired peptide and the "spent" resin is filtered. The "spent" resin is washed with a small volume of either fresh cleavage cocktail or a TFA/DCM (15-20:80-85 v/v) mixture (1 to 2 times using 1 to 2 vol over resin weight). An optional wash of a small volume of MeOH (1 to 2 times using about 1 to 2 vol over resin weight) (Univar, Dublin, Ireland) may follow.

The peptide-rich filtrates are combined and evaporated to <20% of the original filtrate weight (<15% preferred). The crude peptide is precipitated from the concentrated solution by an organic anti-solvent such as MtBE (Univar, Dublin, Ireland) (about 5 to 15 vols, preferably 6.5 to 10 vols), filtered, and washed with small volumes of the same organic anti-solvent (up to 3 times with about 1 to 2 vols). The precipitated peptide may be dried. Dissolution of the dry or semi-wet peptide precipitate for subsequent purification is carried out using a dilute acid such as acetic acid together with an organic solvent such as ACN (INEOS Nitriles, Rolle, Switzerland) (about % v/v depending on the solubility of the peptide and the % at which it elutes during chromatographic purification).

Purification of the peptide to a very high purity (>99%) combined with salt exchange (e.g. from TFA to acetate salt) is achievable by reverse phase preparative HPLC (on C18 or C8 silica, or other suitable packing) to those skilled in the art. Isolation of the purified peptide by lyophilisation or other methods of isolating a peptide powder from solution (e.g. spray-drying, precipitation or crystallization followed by drying) are possible to those skilled in the art.

In the synthesis of chimeric compounds such as dopamine-somatostatin chimeras, the process includes additional steps. The general procedure of these additional steps may be illustrated as follows: before step (i), Step h-1: a dopamine is activated for coupling by dissolution in HCTU and HOBt in DMF;
Step h-2:—a base is added to the solution of step (h-1);
Step h-3: the solution of step (h-2) is agitated for 1 minute then said resin is stirred for about 1.5 hours;
Step h-4: the resulting resin is washed with DMF; and
Step h-5: the resin is further washed with 1-3 vols MeOH.

A mixture of TFA, TIPS and DCM is used to cleave the peptide from the resin and simultaneously remove the side chain protecting groups from the amino acids, and preferably the ratio of TFA:TIPS:DCM is 15:5:80. Then the precipitate is washed with MtBE. Finally, the precipitate is cyclized.

EXPERIMENTAL PART

Example 1

Synthesis of Ghrelin Analogue
H-Inp-D-Bal-D-Trp-Phe-Apc-NH$_2$ (as described in International Patent Application WO 2004/014415 which is incorporated by reference in its entirety herein). In the process as described below, all equivalents are relative to the resin-batch scale.

The titled peptide was synthesized in a 50-liter filter reactor (Buchi, Flawil, Switzerland.

The synthesis was carried out on a 1.04 mole scale (1.4 kg input resin).

Approximately, 1.41 kg. of Fmoc-Sieber Amide resin was swelled with DMF (3 times 10 vol). The Fmoc group was de-protected by two treatments of a 15% v/v solution of piperidine (BASF, Schwarheide, Germany) in DMF (2×10 vols, 10 minutes each). The resin was then washed with DMF (3×10 vols).

Some of the Fmoc amino acids employed (Apc, D-Trp) required Boc-protected side chains, the others (Phe, D-Bal, Inp) did not require side chain protection.

Introduced into the reactor was a solution of 1.5 equivalents of Fmoc-Apc(Boc)-OH, pre-activated with 1.8 equivalents of HCTU and 3 equivalents of DIEA in DMF (6 vol). The solution and resin were stirred for approximately 90 minutes. The resin was drained and washed with DMF (2×10 vol). The Fmoc group was de-protected as outlined above and the second amino acid, Fmoc-Phe-OH, was coupled using the same conditions as outlined for Fmoc-Apc(Boc)-OH. The cycle of Fmoc de-protection, washing and Fmoc-amino acid coupling and washing was repeated for Fmoc-D-Trp(Boc)-OH, Fmoc-D-Bal-OH and Fmoc-Inp-OH with the Fmoc-amino acid coupling steps utilizing 1.45 equivalents of TBTU, 1.45 equivs of HOBt, and 2.25 equivs of DIEA in DMF (6-7 vol). Coupling times were 60 minutes.

Upon completion of the peptide assembly on the Sieber Amide resin, the resin was washed with DMF and then further washed twice with 10 liters of methanol and dried The peptide was cleaved from the resin and its side chain-protecting groups removed using 10 vol. of a cleavage cocktail comprised of TFA/TIPS/DCM (20/10/70% v/v) for 2.5 hours. The peptide-containing filtrate was evaporated under reduced pressure, precipitated and washed with MtBE before being dissolved in dilute acetic acid and acetonitrile for subsequent purification. The synthesis yield was 80.8%, purity by HPLC 90.0%.

The peptide was purified using a reverse-phase preparative HPLC column (Novasep, Pompey, France) packed with C$_{18}$ stationary phase (EKA Chemicals AB, Bohus, Sweden). Purification and salt exchange was performed under gradient elution using ammonium acetate and acetic acid buffers with acetonitrile as organic modifier.

Example 2

Synthesis of the Dopamine-Somatostatin Chimera of the Formula

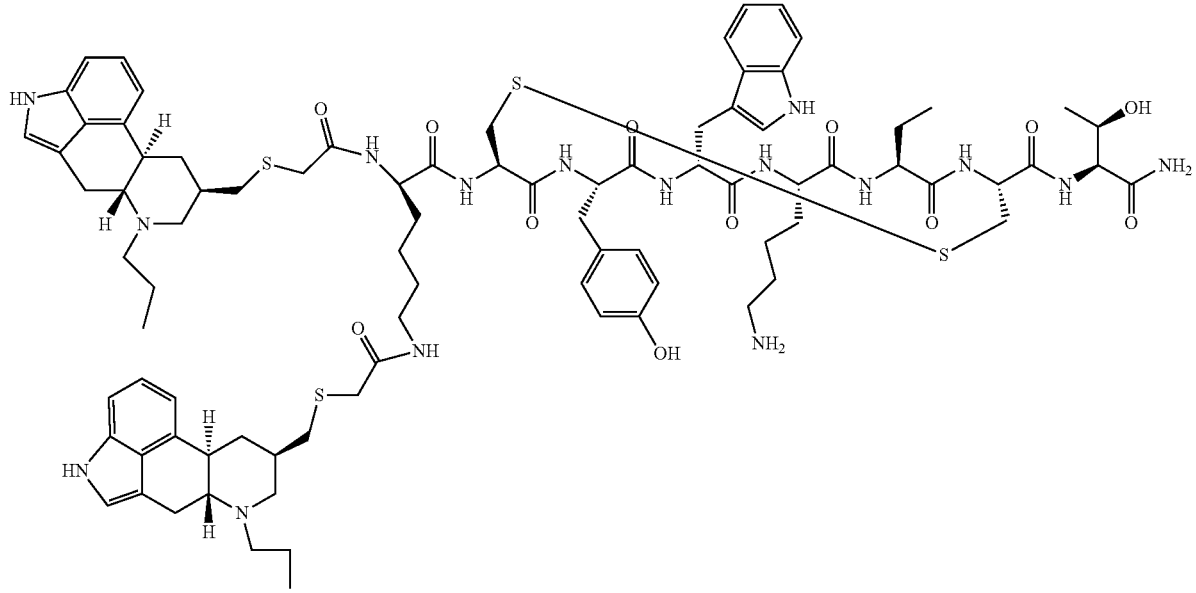 [SMILES: CCCN1C[C@H](CSCC(=O)NCCCC[C@@H](NC(=O)CSC[C@@H]2C[C@@H]3c4cccc5[nH]cc(c45)C[C@H]3N(CCC)C2)C(=O)N[C@H]2CSSC[C@@H](C(=O)N[C@H](C(N)=O)[C@@H](C)O)NC(=O)[C@H](CC)NC(=O)[C@H](CCCCN)NC(=O)[C@@H](Cc3c[nH]c4ccccc34)NC(=O)[C@H](Cc3ccc(O)cc3)NC2=O)C[C@@H]2c3cccc4[nH]cc(c34)C[C@H]21]

(i.e. Dop2-D-Lys(Dop2)-c[Cys-Tyr-D-Trp-Lys-Abu-Cys]-Thr-NH$_2$ as described in International Patent Application WO 2004/091490 which is incorporated by reference in its entirety herein).

In the process as described below, all equivalents are relative to the resin-batch scale.

The titled peptide was synthesized in a 50-liter filter.

The synthesis was carried out on a 0.72 mole scale (1.2 kg input resin).

The protected amino acids employed herein can be obtained from Synthetech, Inc., Albany, Oreg., USA or Senn Chemicals, Dielsdorf, Switzerland About 1.2 kg of Fmoc-Sieber Amide resin was swelled with DMF (3×10 vol) in the reactor and the Fmoc group was de-protected using two treatments of a 15% v/v solution of piperidine in DMF (10 vols per treatment lasting 10 minutes in duration). The resin was washed with DMF (4×10 vols).

The first amino acid to be coupled to the resin, Fmoc-Thr(tBu)-OH (2.0 equivs.), TBTU (1.96 equivs), HOBt (1.96 equivs), and DIEA (3.0 equivs in DMF (5.5 vol)) were stirred with the resin for 60 minutes. The resin was drained and Fmoc-Thr(tBu)-OH was re-coupled using Fmoc-Thr(tBu)-OH (1.0 equivs), TBTU (0.98 equivs), HOBt (0.98 equivs) and DIEA (1.5 equivs) in DMF (2.8 vol) for 60 minutes.

The resin was washed with DMF (4×10 vols).

The Fmoc group was de-protected as outlined above and the second aminoacid, Fmoc-Cys(Acm)-OH, was coupled using the same conditions as outlined for Fmoc-Thr(tBu)-OH. The cycle of Fmoc de-protection, washing, Fmoc-amino acid coupling and washing was repeated for Fmoc-Abu-OH, Fmoc-Lys(Boc)-OH, Fmoc-D-Trp(Boc)-OH, Fmoc-Tyr(tBu)-OH, Fmoc-Cys(Acm)-OH and Fmoc-D-Lys(Fmoc)-OH in that order. The Fmoc-amino acid coupling steps were performed using TBTU (1.96 equivs), HOBt (1.96 equivs) and DIEA (3.0 equivs) in DMF (5.8-7 vol) for 60 minutes.

The dopamine portion of the titled molecule, i.e.

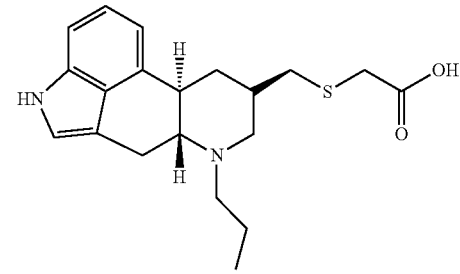

(Biomeasure, Inc., Milford, Mass., USA) was activated for coupling by dissolving it (2.75 molar equivs relative to resin), HCTU (2.79 eq.) and HOBt (3.3 eq.) in DMF (12.3 vols per gram of resin), adding DIEA (6.27 eq.) and agitating for 1 minute before stirring with the resin for 1.5 hours.

After final washing of the peptidyl resin with DMF, the resin was further washed with MeOH (2×10 vol) and dried.

Cleavage of the peptide chimera from the resin and removal of the side chain protecting groups was effected in one pot using TFA:TIPS:DCM (15:5:80, 12 vol, 34.3 L) for 2.0 hours. Intermittent sparging of the cleavage reaction mixture with nitrogen gas was used (for a duration of 1-2 minutes every 30 minutes). After filtration of the cleavage mixture (which contains the desired peptide) from the resin, the "spent" resin was washed with TFA/DCM (15:85) mixture (1.3 vol over resin weight, 3 times). The peptide-rich filtrates were combined and evaporated to 10.4% (6.2 Kg) of original filtrate weight. The crude peptide was precipitated from the concentrated solution by addition to stirred MtBE (6.5 vols over residual weight post evaporation, 40 L), filtered, and washed with MtBE (1 vol over residual weight post evaporation, 6.2 L, once). Dissolution of the semi-dry peptide precipitate for subsequent cyclisation was carried out using 38 vol (45 L) over resin weight of 0.1% v/v TFA/water, with ACN (30% v/v).

The synthesis/cleavage yield was 72.6%, purity by HPLC was 79.1%.

Examples of therapeutic peptides which can be synthesized using the novel process described herein, include, but are not limited to, the following:

```
H-Inp-D-1-Nal-D-Trp-3-Pal-Lys-NH2
H-Inp-D-2-Nal-D-Trp-4-Pal-Lys-NH2
H-Inp-D-2-Nal-D-Trp-Orn-Lys-NH2
H-Inp-D-Bip-D-Trp-Phe-Lys-NH2
H-Inp-D-2-Nal-D-Trp-Thr(Bzl)-Lys-NH2
H-Inp-D-2-Nal-D-Trp-Pff-Lys-NH2
H-Inp-D-2-Nal-D-Trp-2-Thi-Lys-NH2
H-Inp-D-2-Nal-D-Trp-Taz-Lys-NH2
H-Inp-D-Dip-D-Trp-Phe-Lys-NH2
H-Inp-D-Bpa-D-Trp-Phe-Lys-NH2
H-Inp-D-2-Nal-D-Bpa-Phe-Lys-NH2
H-Inp-D-2-Nal-D-Trp-3-Pal-NH2
H-Inp-D-2-Nal-D-Trp-4-Pal-NH2
H-Inp-D-1-Nal-D-Trp-3-Pal-NH2
H-Inp-D-Bip-D-Trp-Phe-NH2
H-Inp-D-2-Nal-D-Trp-Thr(Bzl)-NH2
H-Inp-D-2-Nal-D-Trp-Pff-NH2
H-Inp-D-2-Nal-D-Trp-2-Thi-NH2
H-Inp-D-2-Nal-D-Trp-Taz-NH2
H-Inp-D-Dip-D-Trp-Phe-NH2
H-Inp-D-2-Nal-D-Dip-Phe-NH2
H-Inp-D-Bal-D-Trp-Phe-NH2
H-Inp-D-2-Nal-D-Bal-Phe-NH2
H-Inp-D-2-Nal-D-Trp-3-Pal-Lys-NH2
H-Inp-D-Bal-D-Trp-2-Thi-Lys-NH2
H-Inp-D-Bal-D-Trp-Phe-Lys-NH2
H-Inp-D-1-Nal-D-Trp-2-Thi-Lys-NH2
H-Inp-D-2-Nal-D-Trp-Phe-Apc-NH2
H-Inp-D-1-Nal-D-Trp-Phe-Apc-NH2
H-Inp-D-Bal-D-Trp-Phe-Apc-NH2
H-Apc-D-2-Nal-D-Trp-Phe-Lys-NH2
H-Apc-D-1-Nal-D-Trp-2-Thi-Lys-NH2
H-Inp-D-1-Nal-D-Trp-2-Thi-NH2
H-Apc-D-1-Nal-D-Trp-Phe-NH2
H-Inp-D-1-Nal-D-Trp-Taz-Lys-NH2
H-Inp-D-Bal-D-Trp-Taz-Lys-NH2
H-Apc-D-1-Nal-D-Trp-Taz-Lys-NH2
H-Apc-D-Bal-D-Trp-Taz-Lys-NH2
H-Apc-D-Bal-D-Trp-2-Thi-Lys-NH2
H-Apc-D-Bal-D-Trp-Phe-Lys-NH2
H-Apc-D-1-Nal-D-Trp-Phe-Apc-NH2
H-Apc-D-Bal-D-Trp-Phe-Apc-NH2
H-Apc-D-1-Nal-D-1-Nal-Phe-Apc-NH2
H-Apc-D-1-Nal-D-2-Nal-Phe-Apc-NH2
H-Apc-D-1-Nal-D-1-Nal-Phe-Lys-NH2
H-Apc-D-Bal-D-1-Nal-Phe-Apc-NH2
H-Apc-D-Bal-D-2-Nal-Phe-Apc-NH2
H-Apc-D-Bal-D-1-Nal-Phe-Lys-NH2
H-Apc-D-Bal-D-2-Nal-Phe-Lys-NH2
H-Apc-D-1-Nal-D-Trp-2-Thi-NH2
H-Apc-D-Bal-D-Trp-Phe-NH2
H-Apc-D-1-Nal-D-Trp-Taz-NH2
H-Apc-D-Bal-D-Trp-2-Thi-NH2
H-Apc-D-Bal-D-Trp-Taz-NH2
H-Apc-D-2-Nal-D-Trp-2-Thi-NH2
H-Apc-D-2-Nal-D-Trp-Taz-NH2
H-Inp-D-1-Nal-D-Trp-Taz-Apc-NH2
H-Inp-D-Bal-D-Trp-Taz-Apc-NH2
H-Apc-D-1-Nal-D-Trp-Taz-Apc-NH2
H-Apc-D-Bal-D-Trp-Taz-Apc-NH2
H-Apc-D-1-Nal-D-Trp-2-Fua-Apc-NH2
H-Apc-D-1-Nal-D-Trp-2-Fua-Lys-NH2
H-Apc-D-1-Nal-D-Trp-2-Fua-NH2
H-Apc-D-1-Nal-D-Trp-2-Pal-NH2
H-Apc-D-1-Nal-D-Trp-3-Pal-NH2
H-Apc-D-1-Nal-D-Trp-3-Thi-Apc-NH2
H-Apc-D-1-Nal-D-Trp-3-Thi-Lys-NH2
H-Apc-D-1-Nal-D-Trp-3-Thi-NH2
H-Apc-D-1-Nal-D-Trp-4-Pal-NH2
H-Apc-D-1-Nal-D-Trp-Pff-Apc-NH2
```

-continued

H-Apc-D-1-Nal-D-Trp-Pff-Lys-NH$_2$
H-Apc-D-1-Nal-D-Trp-Pff-NH$_2$
H-Apc-D-2-Nal-D-Trp-2-Fua-Apc-NH$_2$
H-Apc-D-2-Nal-D-Trp-2-Fua-Lys-NH$_2$
H-Apc-D-2-Nal-D-Trp-2-Fua-NH$_2$
H-Apc-D-2-Nal-D-Trp-2-Pal-NH$_2$
H-Apc-D-2-Nal-D-Trp-2-Thi-Apc-NH$_2$
H-Apc-D-2-Nal-D-Trp-2-Thi-Lys-NH$_2$
H-Apc-D-2-Nal-D-Trp-3-Pal-NH$_2$
H-Apc-D-2-Nal-D-Trp-3-Thi-Apc-NH$_2$
H-Apc-D-2-Nal-D-Trp-3-Thi-Lys-NH$_2$
H-Apc-D-2-Nal-D-Trp-3-Thi-NH$_2$
H-Apc-D-2-Nal-D-Trp-4-Pal-NH$_2$
H-Apc-D-2-Nal-D-Trp-Pff-Apc-NH$_2$
H-Apc-D-2-Nal-D-Trp-Pff-Lys-NH$_2$
H-Apc-D-2-Nal-D-Trp-Pff-NH$_2$
H-Apc-D-2-Nal-D-Trp-Taz-Apc-NH$_2$
H-Apc-D-2-Nal-D-Trp-Taz-Lys-NH$_2$
H-Apc-D-Bal-D-Bal-2-Fua-Apc-NH$_2$
H-Apc-D-Bal-D-Bal-2-Fua-Lys-NH$_2$
H-Apc-D-Bal-D-Bal-2-Fua-NH$_2$
H-Apc-D-Bal-D-Bal-2-Pal-NH$_2$
H-Apc-D-Bal-D-Bal-2-Thi-Apc-NH$_2$
H-Apc-D-Bal-D-Bal-2-Thi-Lys-NH$_2$
H-Apc-D-Bal-D-Bal-2-Thi-NH$_2$
H-Apc-D-Bal-D-Bal-3-Pal-NH$_2$
H-Apc-D-Bal-D-Bal-3-Thi-Apc-NH$_2$
H-Apc-D-Bal-D-Bal-3-Thi-Lys-NH$_2$
H-Apc-D-Bal-D-Bal-3-Thi-NH$_2$
H-Apc-D-Bal-D-Bal-4-Pal-NH$_2$
H-Apc-D-Bal-D-Bal-Pff-Apc-NH$_2$
H-Apc-D-Bal-D-Bal-Pff-Lys-NH$_2$
H-Apc-D-Bal-D-Bal-Pff-NH$_2$
H-Apc-D-Bal-D-Bal-Phe-Apc-NH$_2$
H-Apc-D-Bal-D-Bal-Phe-Lys-NH$_2$
H-Apc-D-Bal-D-Bal-Phe-NH$_2$
H-Apc-D-Bal-D-Bal-Taz-Apc-NH$_2$
H-Apc-D-Bal-D-Bal-Taz-Lys-NH$_2$
H-Apc-D-Bal-D-Bal-Taz-NH$_2$
H-Apc-D-Bal-D-Trp-2-Fua-Apc-NH$_2$

-continued

H-Apc-D-Bal-D-Trp-2-Fua-Lys-NH$_2$
H-Apc-D-Bal-D-Trp-2-Fua-NH$_2$
H-Apc-D-Bal-D-Trp-2-Pal-NH$_2$
H-Apc-D-Bal-D-Trp-3-Pal-NH$_2$
H-Apc-D-Bal-D-Trp-3-Thi-Apc-NH$_2$
H-Apc-D-Bal-D-Trp-3-Thi-Lys-NH$_2$
H-Apc-D-Bal-D-Trp-3-Thi-NH$_2$
H-Apc-D-Bal-D-Trp-4-Pal-NH$_2$
H-Apc-D-Bal-D-Trp-Pff-Apc-NH$_2$
H-Apc-D-Bal-D-Trp-Pff-Lys-NH$_2$
H-Apc-D-Bal-D-Trp-Pff-NH$_2$
H-Inp-D-1-Nal-D-Bal-2-Fua-Lys-NH$_2$
H-Inp-D-1-Nal-D-Bal-2-Fua-NH$_2$
H-Inp-D-1-Nal-D-Bal-2-Thi-Lys-NH$_2$
H-Inp-D-1-Nal-D-Bal-3-Thi-Lys-NH$_2$
H-Inp-D-1-Nal-D-Bal-Pff-Lys-NH$_2$
H-Inp-D-1-Nal-D-Bal-Pff-NH$_2$
H-Inp-D-1-Nal-D-Bal-Phe-Lys-NH$_2$
H-Inp-D-1-Nal-D-Bal-Taz-Lys-NH$_2$
H-Inp-D-1-Nal-D-Bal-Taz-NH$_2$
H-Inp-D-1-Nal-D-Trp-2-Fua-Apc-NH$_2$
H-Inp-D-1-Nal-D-Trp-2-Fua-Lys-NH$_2$
H-Inp-D-1-Nal-D-Trp-2-Fua-NH$_2$
H-Inp-D-1-Nal-D-Trp-3-Thi-Apc-NH$_2$
H-Inp-D-1-Nal-D-Trp-3-Thi-Lys-NH$_2$
H-Inp-D-1-Nal-D-Trp-Pff-Apc-NH$_2$
H-Inp-D-1-Nal-D-Trp-Pff-Lys-NH$_2$
H-Inp-D-1-Nal-D-Trp-Pff-NH$_2$
H-Inp-D-1-Nal-D-Trp-Taz-NH$_2$
H-Inp-D-2-Nal-D-Trp-2-Fua-Apc-NH$_2$
H-Inp-D-2-Nal-D-Trp-2-Fua-NH$_2$
H-Inp-D-2-Nal-D-Trp-2-Thi-Apc-NH$_2$
H-Inp-D-2-Nal-D-Trp-3-Thi-Apc-NH$_2$
H-Inp-D-2-Nal-D-Trp-3-Thi-Lys-NH$_2$
H-Inp-D-2-Nal-D-Trp-3-Thi-NH$_2$
H-Inp-D-2-Nal-D-Trp-Pff-Apc-NH$_2$
H-Inp-D-2-Nal-D-Trp-Pff-NH$_2$
H-Inp-D-2-Nal-D-Trp-Taz-Apc-NH$_2$
H-Inp-D-2-Nal-D-Trp-Taz-NH$_2$
H-Inp-D-Bal-D-Bal-2-Fua-Lys-NH$_2$
H-Inp-D-Bal-D-Bal-2-Fua-NH$_2$

-continued

H-Inp-D-Bal-D-Bal-2-Thi-Lys-NH₂
H-Inp-D-Bal-D-Bal-3-Thi-Lys-NH₂
H-Inp-D-Bal-D-Bal-Pff-Lys-NH₂
H-Inp-D-Bal-D-Bal-Pff-NH₂
H-Inp-D-Bal-D-Bal-Phe-Lys-NH₂
H-Inp-D-Bal-D-Bal-Taz-Lys-NH₂
H-Inp-D-Bal-D-Bal-Taz-NH₂
H-Inp-D-Bal-D-Trp-2-Fua-Apc-NH₂
H-Inp-D-Bal-D-Trp-2-Fua-Lys-NH₂
H-Inp-D-Bal-D-Trp-2-Fua-NH₂
H-Inp-D-Bal-D-Trp-3-Thi-Apc-NH₂
H-Inp-D-Bal-D-Trp-3-Thi-Lys-NH₂
H-Inp-D-Bal-D-Trp-Pff-Apc-NH₂
H-Inp-D-Bal-D-Trp-Pff-Lys-NH₂
H-Inp-D-Bal-D-Trp-Pff-NH₂
H-Inp-D-Bal-D-Trp-Taz-NH₂
H-Inp-D-Bip-D-Bal-2-Fua-Lys-NH₂
H-Inp-D-Bip-D-Bal-2-Fua-NH₂
H-Inp-D-Bip-D-Bal-2-Thi-Lys-NH₂
H-Inp-D-Bip-D-Bal-3-Thi-Lys-NH₂
H-Inp-D-Bip-D-Bal-Pff-Lys-NH₂
H-Inp-D-Bip-D-Bal-Pff-NH₂
H-Inp-D-Bip-D-Bal-Taz-Lys-NH₂
H-Inp-D-Bip-D-Bal-Taz-NH₂
H-Inp-D-Bip-D-Trp-2-Fua-Lys-NH₂
H-Inp-D-Bip-D-Trp-2-Fua-NH₂
H-Inp-D-Bip-D-Trp-2-Thi-Lys-NH₂
H-Inp-D-Bip-D-Trp-3-Thi-Lys-NH₂
H-Inp-D-Bip-D-Trp-Pff-Lys-NH₂
H-Inp-D-Bip-D-Trp-Pff-NH₂
H-Inp-D-Bip-D-Trp-Taz-Lys-NH₂
H-Inp-D-Bip-D-Trp-Taz-NH₂
H-Inp-D-1-Nal-D-Trp-3-Pal-Lys-NH₂
H-Inp-D-2-Nal-D-Trp-4-Pal-Lys-NH₂
H-Inp-D-2-Nal-D-Trp-Orn-Lys-NH₂
H-Inp-D-Bip-D-Trp-Phe-Lys-NH₂
H-Inp-D-2-Nal-D-Trp-Thr(Bzl)-Lys-NH₂
H-Inp-D-2-Nal-D-Trp-Pff-Lys-NH₂
H-Inp-D-2-Nal-D-Trp-2-Thi-Lys-NH₂
H-Inp-D-2-Nal-D-Trp-Taz-Lys-NH₂
H-Inp-D-Dip-D-Trp-Phe-Lys-NH₂
H-Inp-D-Bpa-D-Trp-Phe-Lys-NH₂
H-Inp-D-2-Nal-D-Bpa-Phe-Lys-NH₂
H-Inp-D-2-Nal-D-Trp-Thr(Bzl)-NH₂
H-Inp-D-2-Nal-D-Trp-Pff-NH₂
H-Inp-D-2-Nal-D-Trp-Taz-NH₂
H-Inp-D-2-Nal-D-Dip-Phe-NH₂
H-Inp-D-2-Nal-D-Trp-3-Pal-Lys-NH₂
H-Inp-D-Bal-D-Trp-2-Thi-Lys-NH₂
H-Inp-D-Bal-D-Trp-Phe-Lys-NH₂
H-Inp-D-1-Nal-D-Trp-2-Thi-Lys-NH₂
H-Inp-D-2-Nal-D-Trp-Phe-Apc-NH₂
H-Inp-D-1-Nal-D-Trp-Phe-Apc-NH₂
H-Inp-D-Bal-D-Trp-Phe-Apc-NH₂
H-Apc-D-2-Nal-D-Trp-Phe-Lys-NH₂
H-Apc-D-1-Nal-D-Trp-2-Thi-Lys-NH₂
H-Inp-D-1-Nal-D-Trp-Taz-Lys-NH₂
H-Inp-D-Bal-D-Trp-Taz-Lys-NH₂
H-Apc-D-1-Nal-D-Trp-Taz-Lys-NH₂
H-Apc-D-Bal-D-Trp-Taz-Lys-NH₂
H-Apc-D-Bal-D-Trp-2-Thi-Lys-NH₂
H-Apc-D-Bal-D-Trp-Phe-Lys-NH₂
H-Apc-D-1-Nal-D-Trp-Phe-Apc-NH₂
H-Apc-D-Bal-D-Trp-Phe-Apc-NH₂
H-Apc-D-1-Nal-D-1-Nal-Phe-Apc-NH₂
H-Apc-D-1-Nal-D-2-Nal-Phe-Apc-NH₂
H-Apc-D-1-Nal-D-1-Nal-Phe-Lys-NH₂
H-Apc-D-Bal-D-1-Nal-Phe-Apc-NH₂
H-Apc-D-Bal-D-2-Nal-Phe-Apc-NH₂
H-Apc-D-Bal-D-1-Nal-Phe-Lys-NH₂
H-Apc-D-Bal-D-2-Nal-Phe-Lys-NH₂
H-Apc-D-1-Nal-D-Trp-2-Thi-NH₂
H-Apc-D-Bal-D-Trp-Phe-NH₂
H-Apc-D-1-Nal-D-Trp-Taz-NH₂
H-Apc-D-Bal-D-Trp-2-Thi-NH₂
H-Apc-D-Bal-D-Trp-Taz-NH₂
H-Apc-D-2-Nal-D-Trp-2-Thi-NH₂
H-Apc-D-2-Nal-D-Trp-Taz-NH₂
H-Inp-D-1-Nal-D-Trp-Taz-Apc-NH₂
H-Inp-D-Bal-D-Trp-Taz-Apc-NH₂
H-Apc-D-1-Nal-D-Trp-Taz-Apc-NH₂

-continued

H-Apc-D-Bal-D-Trp-Taz-Apc-NH₂
H-Inp-D-2-Nal-D-Trp-3-Thi-Lys-NH₂
H-Inp-D-Bal-D-Trp-3-Thi-Lys-NH₂
H-Inp-D-Bal-D-Trp-2-Fua-Lys-NH₂
H-Inp-D-Bal-D-Trp-Pff-Lys-NH₂
H-Inp-D-Bal-D-Trp-3-Thi-Apc-NH₂
H-Inp-D-Bal-D-Trp-2-Fua-Apc-NH₂
H-Inp-D-Bal-D-Trp-Pff-Apc-NH₂
H-Apc-D-Bal-D-Trp-3-Thi-Lys-NH₂
H-Apc-D-Bal-D-Trp-2-Fua-Lys-NH₂
H-Apc-D-Bal-D-Trp-Pff-Lys-NH₂
H-Inp-D-Bal-D-Bal-Phe-Lys-NH₂
H-Inp-D-Bal-D-Bal-2-Thi-Lys-NH₂
H-Inp-D-Bal-D-Bal-3-Thi-Lys-NH₂
H-Inp-D-Bal-D-Bal-Taz-Lys-NH₂
H-Inp-D-Bal-D-Bal-2-Fua-Lys-NH₂
H-Inp-D-Bal-D-Bal-Pff-Lys-NH₂
H-Apc-D-Bal-D-Bal-Phe-Lys-NH₂
H-Apc-D-Bal-D-Bal-2-Thi-Lys-NH₂
H-Apc-D-Bal-D-Bal-3-Thi-Lys-NH₂
H-Apc-D-Bal-D-Bal-Taz-Lys-NH₂
H-Apc-D-Bal-D-Bal-2-Fua-Lys-NH₂
H-Apc-D-Bal-D-Bal-Pff-Lys-NH₂
H-Inp-D-1-Nal-D-Trp-3-Thi-Lys-NH₂
H-Inp-D-1-Nal-D-Trp-2-Fua-Lys-NH₂
H-Inp-D-1-Nal-D-Trp-Pff-Lys-NH₂
H-Inp-D-1-Nal-D-Bal-Phe-Lys-NH₂
H-Inp-D-1-Nal-D-Bal-2-Thi-Lys-NH₂
H-Inp-D-1-Nal-D-Bal-3-Thi-Lys-NH₂
H-Inp-D-1-Nal-D-Bal-Taz-Lys-NH₂
H-Inp-D-1-Nal-D-Bal-2-Fua-Lys-NH₂
H-Inp-D-1-Nal-D-Bal-Pff-Lys-NH₂
H-Inp-D-2-Nal-D-Trp-2-Thi-Apc-NH₂
H-Inp-D-2-Nal-D-Trp-3-Thi-Apc-NH₂
H-Inp-D-2-Nal-D-Trp-Taz-Apc-NH₂
H-Inp-D-2-Nal-D-Trp-2-Fua-Apc-NH₂
H-Inp-D-2-Nal-D-Trp-Pff-Apc-NH₂
H-Inp-D-1-Nal-D-Trp-3-Thi-Apc-NH₂
H-Inp-D-1-Nal-D-Trp-2-Fua-Apc-NH₂
H-Inp-D-1-Nal-D-Trp-Pff-Apc-NH₂

-continued

H-Apc-D-1-Nal-D-Trp-3-Thi-Lys-NH₂
H-Apc-D-1-Nal-D-Trp-2-Fua-Lys-NH₂
H-Apc-D-1-Nal-D-Trp-Pff-Lys-NH₂
H-Apc-D-2-Nal-D-Trp-2-Thi-Lys-NH₂
H-Apc-D-2-Nal-D-Trp-3-Thi-Lys-NH₂
H-Apc-D-2-Nal-D-Trp-Taz-Lys-NH₂
H-Apc-D-2-Nal-D-Trp-2-Fua-Lys-NH₂
H-Apc-D-2-Nal-D-Trp-Pff-Lys-NH₂
H-Inp-D-Bip-D-Trp-2-Thi-Lys-NH₂
H-Inp-D-Bip-D-Trp-3-Thi-Lys-NH₂
H-Inp-D-Bip-D-Trp-Taz-Lys-NH₂
H-Inp-D-Bip-D-Trp-2-Fua-Lys-NH₂
H-Inp-D-Bip-D-Trp-Pff-Lys-NH₂
H-Inp-D-Bip-D-Bal-2-Thi-Lys-NH₂
H-Inp-D-Bip-D-Bal-3-Thi-Lys-NH₂
H-Inp-D-Bip-D-Bal-Taz-Lys-NH₂
H-Inp-D-Bip-D-Bal-2-Fua-Lys-NH₂
H-Inp-D-Bip-D-Bal-Pff-Lys-NH₂
H-Apc-D-Bal-D-Trp-3-Thi-Apc-NH₂
H-Apc-D-Bal-D-Trp-2-Fua-Apc-NH₂
H-Apc-D-Bal-D-Trp-Pff-Apc-NH₂
H-Apc-D-Bal-D-Bal-Phe-Apc-NH₂
H-Apc-D-Bal-D-Bal-2-Thi-Apc-NH₂
H-Apc-D-Bal-D-Bal-3-Thi-Apc-NH₂
H-Apc-D-Bal-D-Bal-Taz-Apc-NH₂
H-Apc-D-Bal-D-Bal-2-Fua-Apc-NH₂
H-Apc-D-Bal-D-Bal-Pff-Apc-NH₂
H-Apc-D-1-Nal-D-Trp-3-Thi-Apc-NH₂
H-Apc-D-1-Nal-D-Trp-2-Fua-Apc-NH₂
H-Apc-D-1-Nal-D-Trp-Pff-Apc-NH₂
H-Apc-D-2-Nal-D-Trp-2-Thi-Apc-NH₂
H-Apc-D-2-Nal-D-Trp-3-Thi-Apc-NH₂
H-Apc-D-2-Nal-D-Trp-Taz-Apc-NH₂
H-Apc-D-2-Nal-D-Trp-2-Fua-Apc-NH₂
H-Apc-D-2-Nal-D-Trp-Pff-Apc-NH₂
H-Inp-D-Bal-D-Trp-Taz-NH₂
H-Inp-D-Bal-D-Trp-2-Fua-NH₂
H-Inp-D-Bal-D-Trp-Pff-NH₂
H-Apc-D-Bal-D-Trp-3-Thi-NH₂
H-Apc-D-Bal-D-Trp-2-Fua-NH₂
H-Apc-D-Bal-D-Trp-Pff-NH₂

H-Apc-D-Bal-D-Trp-4-Pal-NH$_2$

H-Apc-D-Bal-D-Trp-3-Pal-NH$_2$

H-Apc-D-Bal-D-Trp-2-Pal-NH$_2$

H-Inp-D-Bal-D-Bal-Taz-NH$_2$

H-Inp-D-Bal-D-Bal-2-Fua-NH$_2$

H-Inp-D-Bal-D-Bal-Pff-NH$_2$

H-Apc-D-Bal-D-Bal-Phe-NH$_2$

H-Apc-D-Bal-D-Bal-2-Thi-NH$_2$

H-Apc-D-Bal-D-Bal-3-Thi-NH$_2$

H-Apc-D-Bal-D-Bal-Taz-NH$_2$

H-Apc-D-Bal-D-Bal-2-Fua-NH$_2$

H-Apc-D-Bal-D-Bal-Pff-NH$_2$

H-Apc-D-Bal-D-Bal-4-Pal-NH$_2$

H-Apc-D-Bal-D-Bal-3-Pal-NH$_2$

H-Apc-D-Bal-D-Bal-2-Pal-NH$_2$

H-Inp-D-1-Nal-D-Trp-Taz-NH$_2$

H-Inp-D-1-Nal-D-Trp-2-Fua-NH$_2$

H-Inp-D-1-Nal-D-Trp-Pff-NH$_2$

H-Inp-D-1-Nal-D-Bal-Taz-NH$_2$

H-Inp-D-1-Nal-D-Bal-2-Fua-NH$_2$

H-Inp-D-1-Nal-D-Bal-Pff-NH$_2$

H-Inp-D-2-Nal-D-Trp-Taz-NH$_2$

H-Inp-D-2-Nal-D-Trp-2-Fua-NH$_2$

H-Inp-D-2-Nal-D-Trp-Pff-NH$_2$

H-Apc-D-1-Nal-D-Trp-3-Thi-NH$_2$

H-Apc-D-1-Nal-D-Trp-2-Fua-NH$_2$

H-Apc-D-1-Nal-D-Trp-Pff-NH$_2$

H-Apc-D-1-Nal-D-Trp-4-Pal-NH$_2$

H-Apc-D-1-Nal-D-Trp-3-Pal-NH$_2$

H-Apc-D-1-Nal-D-Trp-2-Pal-NH$_2$

H-Apc-D-2-Nal-D-Trp-3-Thi-NH$_2$

H-Apc-D-2-Nal-D-Trp-2-Fua-NH$_2$

H-Apc-D-2-Nal-D-Trp-Pff-NH$_2$

H-Apc-D-2-Nal-D-Trp-4-Pal-NH$_2$

H-Apc-D-2-Nal-D-Trp-3-Pal-NH$_2$

H-Apc-D-2-Nal-D-Trp-2-Pal-NH$_2$

H-Inp-D-Bip-D-Trp-Taz-NH$_2$

H-Inp-D-Bip-D-Trp-2-Fua-NH$_2$

H-Inp-D-Bip-D-Trp-Pff-NH$_2$;

H-Inp-D-Bip-D-Bal-Taz-NH$_2$

H-Inp-D-Bip-D-Bal-2-Fua-NH$_2$

H-Inp-D-Bip-D-Bal-Pff-NH$_2$

H-Inp-D-1-Nal-D-Trp-2-Thi-Apc-NH$_2$

H-Inp-D-Bal-D-Trp-2-Thi-Apc-NH$_2$

H-Apc-D-1-Nal-D-Trp-2-Thi-Apc-NH$_2$

H-Apc-D-Bal-D-Trp-2-Thi-Apc-NH$_2$
and

H-Apc-D-1-Nal-D-Trp-Phe-Lys-NH$_2$.

Dopamine-somatostatin chimeras that may be synthesized using the claimed method, include but are not limited to, those molecules as described in WO 02/100888 and WO 04/091490, as follows:

Dop2-D-Phe-Doc-D-Phe-c[Cys-3-I-Tyr-D-Trp-Lys-Val-Cys]-Thr-NH$_2$

Ac-Lys(Dop2)-D-Tyr-D-Tyr-c[Cys-Tyr-D-Trp-Lys-Abu-Cys]-Thr-NH$_2$

Ac-D-Lys(Dop2)-D-Phe-c[Cys-3-I-Tyr-D-Trp-Lys-Thr-Cys]-Thr-NH$_2$

Dop2-Lys(Ac)-D-Tyr-D-Tyr-c[Cys-Tyr-D-Trp-Lys-Abu-Cys]-Thr-NH$_2$

Dop2-D-Lys(Ac)-D-Phe-c[Cys-3-I-Tyr-D-Trp-Lys-Thr-Cys]-Thr-NH$_2$

Dop3-D-Phe-c[Cys-Tyr-D-Trp-Lys-Abu-Cys]-Thr-NH$_2$

Dop4-D-Phe-c[Cys-Tyr-D-Trp-Lys-Abu-Cys]-Thr-NH$_2$

Dop3-Aepa-D-Phe-c[Cys-Tyr-D-Trp-Lys-Abu-Cys]-Thr-NH$_2$

Dop4-Aepa-D-Phe-c[Cys-Tyr-D-Trp-Lys-Abu-Cys]-Thr-NH$_2$

Dop5-D-Phe-c[Cys-Tyr-D-Trp-Lys-Abu-Cys]-Thr-NH$_2$

Dop6-D-Phe-c[Cys-Tyr-D-Trp-Lys-Abu-Cys]-Thr-NH$_2$

Dop7-D-Phe-c[Cys-Tyr-D-Trp-Lys-Abu-Cys]-Thr-NH$_2$

Dop8-D-Phe-c[Cys-Tyr-D-Trp-Lys-Abu-Cys]-Thr-NH$_2$

Dop9-D-Phe-c[Cys-Tyr-D-Trp-Lys-Abu-Cys]-Thr-NH$_2$

```
Dop10-D-Phe-c[Cys-Tyr-D-Trp-Lys-Abu-Cys]-Thr-NH2
Dop11-D-Phe-c[Cys-Tyr-D-Trp-Lys-Abu-Cys]-Thr-NH2
Dop12-D-Phe-c[Cys-Tyr-D-Trp-Lys-Abu-Cys]-Thr-NH2
Dop13-D-Phe-c[Cys-Tyr-D-Trp-Lys-Abu-Cys]-Thr-NH2
Dop5-c[Cys-Tyr-D-Trp-Lys-Abu-Cys]-Thr-NH2
Dop6-c[Cys-Tyr-D-Trp-Lys-Abu-Cys]-Thr-NH2
Dop7-c[Cys-Tyr-D-Trp-Lys-Abu-Cys]-Thr-NH2
Dop8-c[Cys-Tyr-D-Trp-Lys-Abu-Cys]-Thr-NH2
Dop9-c[Cys-Tyr-D-Trp-Lys-Abu-Cys]-Thr-NH2
Dop10-c[Cys-Tyr-D-Trp-Lys-Abu-Cys]-Thr-NH2
Dop11-c[Cys-Tyr-D-Trp-Lys-Abu-Cys]-Thr-NH2
Dop12-c[Cys-Tyr-D-Trp-Lys-Abu-Cys]-Thr-NH2
Dop13-c[Cys-Tyr-D-Trp-Lys-Abu-Cys]-Thr-NH2
Dop5-D-2-Nal-c[Cys-Tyr-D-Trp-Lys-Val-Cys]-Thr-NH2
Dop6-D-2-Nal-c[Cys-Tyr-D-Trp-Lys-Val-Cys]-Thr-NH2
Dop7-D-2-Nal-c[Cys-Tyr-D-Trp-Lys-Val-Cys]-Thr-NH2
Dop8-D-2-Nal-c[Cys-Tyr-D-Trp-Lys-Val-Cys]-Thr-NH2
Dop9-D-2-Nal-c[Cys-Tyr-D-Trp-Lys-Val-Cys]-Thr-NH2
Dop10-D-2-Nal-c[Cys-Tyr-D-Trp-Lys-Val-Cys]-Thr-NH2
Dop11-D-2-Nal-c[Cys-Tyr-D-Trp-Lys-Val-Cys]-Thr-NH2
Dop12-D-2-Nal-c[Cys-Tyr-D-Trp-Lys-Val-Cys]-Thr-NH2
Dop13-D-2-Nal-c[Cys-Tyr-D-Trp-Lys-Val-Cys]-Thr-NH2
Dop5-c[Cys-Tyr-D-Trp-Lys-Val-Cys]-Thr-NH2
Dop6-c[Cys-Tyr-D-Trp-Lys-Val-Cys]-Thr-NH2
Dop7-c[Cys-Tyr-D-Trp-Lys-Val-Cys]-Thr-NH2
Dop8-c[Cys-Tyr-D-Trp-Lys-Val-Cys]-Thr-NH2
Dop9-c[Cys-Tyr-D-Trp-Lys-Val-Cys]-Thr-NH2
Dop10-c[Cys-Tyr-D-Trp-Lys-Val-Cys]-Thr-NH2
Dop11-c[Cys-Tyr-D-Trp-Lys-Val-Cys]-Thr-NH2
Dop12-c[Cys-Tyr-D-Trp-Lys-Val-Cys]-Thr-NH2
Dop13-c[Cys-Tyr-D-Trp-Lys-Val-Cys]-Thr-NH2
Dop5-D-Phe-c[Cys-Tyr-D-Trp-Lys-Thr-Cys]-2-Nal-NH2
Dop6-D-Phe-c[Cys-Tyr-D-Trp-Lys-Thr-Cys]-2-Nal-NH2
Dop7-D-Phe-c[Cys-Tyr-D-Trp-Lys-Thr-Cys]-2-Nal-NH2
Dop8-D-Phe-c[Cys-Tyr-D-Trp-Lys-Thr-Cys]-2-Nal-NH2
Dop9-D-Phe-c[Cys-Tyr-D-Trp-Lys-Thr-Cys]-2-Nal-NH2
Dop10-D-Phe-c[Cys-Tyr-D-Trp-Lys-Thr-Cys]-2-Nal-NH2
Dop11-D-Phe-c[Cys-Tyr-D-Trp-Lys-Thr-Cys]-2-Nal-NH2
Dop12-D-Phe-c[Cys-Tyr-D-Trp-Lys-Thr-Cys]-2-Nal-NH2
Dop13-D-Phe-c[Cys-Tyr-D-Trp-Lys-Thr-Cys]-2-Nal-NH2
```

-continued

Dop5-c[Cys-Tyr-D-Trp-Lys-Thr-Cys]-2-Nal-NH$_2$

Dop6-c[Cys-Tyr-D-Trp-Lys-Thr-Cys]-2-Nal-NH$_2$

Dop7-c[Cys-Tyr-D-Trp-Lys-Thr-Cys]-2-Nal-NH$_2$

Dop8-c[Cys-Tyr-D-Trp-Lys-Thr-Cys]-2-Nal-NH$_2$

Dop9-c[Cys-Tyr-D-Trp-Lys-Thr-Cys]-2-Nal-NH$_2$

Dop10-c[Cys-Tyr-D-Trp-Lys-Thr-Cys]-2-Nal-NH$_2$

Dop11-c[Cys-Tyr-D-Trp-Lys-Thr-Cys]-2-Nal-NH$_2$

Dop12-c[Cys-Tyr-D-Trp-Lys-Thr-Cys]-2-Nal-NH$_2$

Dop13-c[Cys-Tyr-D-Trp-Lys-Thr-Cys]-2-Nal-NH$_2$

Dop1-D-Phe-c[Cys-3-I-Tyr-D-Trp-Lys-Thr-Cys]-Thr-NH$_2$

Dop2-D-Phe-c[Cys-3-I-Tyr-D-Trp-Lys-Thr-Cys]-Thr-NH$_2$

Dop1-Aepa-D-Phe-c[Cys-3-I-Tyr-D-Trp-Lys-Thr-Cys]-Thr-NH$_2$

Dop2-Aepa-D-Phe-c[Cys-3-I-Tyr-D-Trp-Lys-Thr-Cys]-Thr-NH$_2$

Dop3-Aepa-D-Phe-c[Cys-3-I-Tyr-D-Trp-Lys-Thr-Cys]-Thr-NH$_2$

Dop4-Aepa-D-Phe-c[Cys-3-I-Tyr-D-Trp-Lys-Thr-Cys]-Thr-NH$_2$

Dop3-D-Phe-c[Cys-3-I-Tyr-D-Trp-Lys-Thr-Cys]-Thr-NH$_2$

Dop4-D-Phe-c[Cys-3-I-Tyr-D-Trp-Lys-Thr-Cys]-Thr-NH$_2$

Dop5-D-Phe-c[Cys-3-I-Tyr-D-Trp-Lys-Thr-Cys]-Thr-NH$_2$

Dop6-D-Phe-c[Cys-3-I-Tyr-D-Trp-Lys-Thr-Cys]-Thr-NH$_2$

Dop7-D-Phe-c[Cys-3-I-Tyr-D-Trp-Lys-Thr-Cys]-Thr-NH$_2$

Dop8-D-Phe-c[Cys-3-I-Tyr-D-Trp-Lys-Thr-Cys]-Thr-NH$_2$

Dop9-D-Phe-c[Cys-3-I-Tyr-D-Trp-Lys-Thr-Cys]-Thr-NH$_2$

Dop10-D-Phe-c[Cys-3-I-Tyr-D-Trp-Lys-Thr-Cys]-Thr-NH$_2$

Dop11-D-Phe-c[Cys-3-I-Tyr-D-Trp-Lys-Thr-Cys]-Thr-NH$_2$

Dop12-D-Phe-c[Cys-3-I-Tyr-D-Trp-Lys-Thr-Cys]-Thr-NH$_2$

Dop13-D-Phe-c[Cys-3-I-Tyr-D-Trp-Lys-Thr-Cys]-Thr-NH$_2$

Dop3-c[Cys-3-I-Tyr-D-Trp-Lys-Thr-Cys]-Thr-NH$_2$

Dop4-c[Cys-3-I-Tyr-D-Trp-Lys-Thr-Cys]-Thr-NH$_2$

Dop5-c[Cys-3-I-Tyr-D-Trp-Lys-Thr-Cys]-Thr-NH$_2$

Dop6-c[Cys-3-I-Tyr-D-Trp-Lys-Thr-Cys]-Thr-NH$_2$

Dop7-c[Cys-3-I-Tyr-D-Trp-Lys-Thr-Cys]-Thr-NH$_2$

Dop8-c[Cys-3-I-Tyr-D-Trp-Lys-Thr-Cys]-Thr-NH$_2$

Dop9-c[Cys-3-I-Tyr-D-Trp-Lys-Thr-Cys]-Thr-NH$_2$

Dop10-c[Cys-3-I-Tyr-D-Trp-Lys-Thr-Cys]-Thr-NH$_2$

Dop11-c[Cys-3-I-Tyr-D-Trp-Lys-Thr-Cys]-Thr-NH$_2$

Dop12-c[Cys-3-I-Tyr-D-Trp-Lys-Thr-Cys]-Thr-NH$_2$

Dop13-c[Cys-3-I-Tyr-D-Trp-Lys-Thr-Cys]-Thr-NH$_2$

Dop1-Caeg-c[D-Cys-3-Pal-D-Trp-Lys-D-Cys]-Thr(Bzl)-Tyr-NH$_2$

Dop2-Caeg-c[D-Cys-3-Pal-D-Trp-Lys-D-Cys]-Thr(Bzl)-Tyr-NH$_2$

Dop3-Caeg-c[D-Cys-3-Pal-D-Trp-Lys-D-Cys]-Thr(Bzl)-Tyr-NH$_2$

Dop4-Caeg-c[D-Cys-3-Pal-D-Trp-Lys-D-Cys]-Thr(Bzl)-Tyr-NH$_2$

Dop1-Aepa-Caeg-c[D-Cys-3-Pal-D-Trp-Lys-D-Cys]-Thr(Bzl)-Tyr-NH$_2$

Dop2-Aepa-Caeg-c[D-Cys-3-Pal-D-Trp-Lys-D-Cys]-Thr(Bzl)-Tyr-NH$_2$

Dop3-Aepa-Caeg-c[D-Cys-3-Pal-D-Trp-Lys-D-Cys]-Thr(Bzl)-Tyr-NH$_2$

Dop4-Aepa-Caeg-c[D-Cys-3-Pal-D-Trp-Lys-D-Cys]-Thr(Bzl)-Tyr-NH$_2$

Dop5-Caeg-c[D-Cys-3-Pal-D-Trp-Lys-D-Cys]-Thr(Bzl)-Tyr-NH$_2$

Dop6-Caeg-c[D-Cys-3-Pal-D-Trp-Lys-D-Cys]-Thr(Bzl)-Tyr-NH$_2$

Dop7-Caeg-c[D-Cys-3-Pal-D-Trp-Lys-D-Cys]-Thr(Bzl)-Tyr-NH$_2$

Dop8-Caeg-c[D-Cys-3-Pal-D-Trp-Lys-D-Cys]-Thr(Bzl)-Tyr-NH$_2$

Dop9-Caeg-c[D-Cys-3-Pal-D-Trp-Lys-D-Cys]-Thr(Bzl)-Tyr-NH$_2$

Dop10-Caeg-c[D-Cys-3-Pal-D-Trp-Lys-D-Cys]-Thr(Bzl)-Tyr-NH$_2$

Dop11-Caeg-c[D-Cys-3-Pal-D-Trp-Lys-D-Cys]-Thr(Bzl)-Tyr-NH$_2$

Dop12-Caeg-c[D-Cys-3-Pal-D-Trp-Lys-D-Cys]-Thr(Bzl)-Tyr-NH$_2$

Dop13-Caeg-c[D-Cys-3-Pal-D-Trp-Lys-D-Cys]-Thr(Bzl)-Tyr-NH$_2$

Dop1-Caeg-c[D-Cys-Phe-D-Trp-Lys-D-Cys]-Ser(Bzl)-Tyr-NH$_2$

Dop2-Caeg-c[D-Cys-Phe-D-Trp-Lys-D-Cys]-Ser(Bzl)-Tyr-NH$_2$

Dop3-Caeg-c[D-Cys-Phe-D-Trp-Lys-D-Cys]-Ser(Bzl)-Tyr-NH$_2$

Dop4-Caeg-c[D-Cys-Phe-D-Trp-Lys-D-Cys]-Ser(Bzl)-Tyr-NH$_2$

Dop1-Aepa-Caeg-c[D-Cys-Phe-D-Trp-Lys-D-Cys]-Ser(Bzl)-Tyr-NH$_2$

Dop2-Aepa-Caeg-c[D-Cys-Phe-D-Trp-Lys-D-Cys]-Ser(Bzl)-Tyr-NH$_2$

Dop3-Aepa-Caeg-c[D-Cys-Phe-D-Trp-Lys-D-Cys]-Ser(Bzl)-Tyr-NH$_2$

Dop4-Aepa-Caeg-c[D-Cys-Phe-D-Trp-Lys-D-Cys]-Ser(Bzl)-Tyr-NH$_2$

Dop5-Caeg-c[D-Cys-Phe-D-Trp-Lys-D-Cys]-Ser(Bzl)-Tyr-NH$_2$

Dop6-Caeg-c[D-Cys-Phe-D-Trp-Lys-D-Cys]-Ser(Bzl)-Tyr-NH$_2$

Dop7-Caeg-c[D-Cys-Phe-D-Trp-Lys-D-Cys]-Ser(Bzl)-Tyr-NH$_2$

Dop8-Caeg-c[D-Cys-Phe-D-Trp-Lys-D-Cys]-Ser(Bzl)-Tyr-NH$_2$

Dop9-Caeg-c[D-Cys-Phe-D-Trp-Lys-D-Cys]-Ser(Bzl)-Tyr-NH$_2$

Dop10-Caeg-c[D-Cys-Phe-D-Trp-Lys-D-Cys]-Ser(Bzl)-Tyr-NH$_2$

Dop11-Caeg-c[D-Cys-Phe-D-Trp-Lys-D-Cys]-Ser(Bzl)-Tyr-NH$_2$

Dop12-Caeg-c[D-Cys-Phe-D-Trp-Lys-D-Cys]-Ser(Bzl)-Tyr-NH$_2$

Dop13-Caeg-c[D-Cys-Phe-D-Trp-Lys-D-Cys]-Ser(Bzl)-Tyr-NH$_2$

Dop5-c[Cys-Phe-Phe-D-Trp-Lys-Thr-Phe-Cys]-NH$_2$

Dop6-c[Cys-Phe-Phe-D-Trp-Lys-Thr-Phe-Cys]-NH$_2$

Dop7-c[Cys-Phe-Phe-D-Trp-Lys-Thr-Phe-Cys]-NH$_2$

Dop8-c[Cys-Phe-Phe-D-Trp-Lys-Thr-Phe-Cys]-NH$_2$

Dop9-c[Cys-Phe-Phe-D-Trp-Lys-Thr-Phe-Cys]-NH$_2$

Dop10-c[Cys-Phe-Phe-D-Trp-Lys-Thr-Phe-Cys]-NH$_2$

Dop11-c[Cys-Phe-Phe-D-Trp-Lys-Thr-Phe-Cys]-NH$_2$

Dop12-c[Cys-Phe-Phe-D-Trp-Lys-Thr-Phe-Cys]-NH$_2$

Dop13-c[Cys-Phe-Phe-D-Trp-Lys-Thr-Phe-Cys]-NH$_2$

Dop5-D-Phe-c[Cys-Phe-(N-Me)D-Trp-Lys-Thr-Cys]-Thr-NH$_2$

-continued

Dop6-D-Phe-c[Cys-Phe-(N-Me)D-Trp-Lys-Thr-Cys]-Thr-NH$_2$

Dop7-D-Phe-c[Cys-Phe-(N-Me)D-Trp-Lys-Thr-Cys]-Thr-NH$_2$

Dop8-D-Phe-c[Cys-Phe-(N-Me)D-Trp-Lys-Thr-Cys]-Thr-NH$_2$

Dop9-D-Phe-c[Cys-Phe-(N-Me)D-Trp-Lys-Thr-Cys]-Thr-NH$_2$

Dop10-D-Phe-c[Cys-Phe-(N-Me)D-Trp-Lys-Thr-Cys]-Thr-NH$_2$

Dop11-D-Phe-c[Cys-Phe-(N-Me)D-Trp-Lys-Thr-Cys]-Thr-NH$_2$

Dop12-D-Phe-c[Cys-Phe-(N-Me)D-Trp-Lys-Thr-Cys]-Thr-NH$_2$

Dop13-D-Phe-c[Cys-Phe-(N-Me)D-Trp-Lys-Thr-Cys]-Thr-NH$_2$

Dop5-c[Cys-Phe-(N-Me)D-Trp-Lys-Thr-Cys]-Thr-NH$_2$

Dop6-c[Cys-Phe-(N-Me)D-Trp-Lys-Thr-Cys]-Thr-NH$_2$

Dop7-c[Cys-Phe-(N-Me)D-Trp-Lys-Thr-Cys]-Thr-NH$_2$

Dop8-c[Cys-Phe-(N-Me)D-Trp-Lys-Thr-Cys]-Thr-NH$_2$

Dop9-c[Cys-Phe-(N-Me)D-Trp-Lys-Thr-Cys]-Thr-NH$_2$

Dop10-c[Cys-Phe-(N-Me)D-Trp-Lys-Thr-Cys]-Thr-NH$_2$

Dop11-c[Cys-Phe-(N-Me)D-Trp-Lys-Thr-Cys]-Thr-NH$_2$

Dop12-c[Cys-Phe-(N-Me)D-Trp-Lys-Thr-Cys]-Thr-NH$_2$

Dop13-c[Cys-Phe-(N-Me)D-Trp-Lys-Thr-Cys]-Thr-NH$_2$

Dop2-Lys(Dop2)-c[Cys-Tyr-D-Trp-Lys-Abu-Cys]-Thr-NH$_2$

Dop2-D-Lys(Dop2)-c[Cys-Tyr-D-Trp-Lys-Abu-Cys]-Thr-NH$_2$

Dop2-Lys(Dop2)-D-Phe-c[Cys-Tyr-D-Trp-Lys-Abu-Cys]-Thr-NH$_2$

Dop2-D-Lys(Dop2)-D-Phe-c[Cys-Tyr-D-Trp-Lys-Abu-Cys]-Thr-NH$_2$

Dop2-Lys(Dop2)-Lys-D-Tyr-D-Tyr-c[Cys-Tyr-D-Trp-Lys-Abu-Cys]-Thr-NH$_2$

Dop2-D-Lys(Dop2)-Lys-D-Tyr-D-Tyr-c[Cys-Tyr-D-Trp-Lys-Abu-Cys]-Thr-NH$_2$

Dop2-D-Lys(Dop2)-D-Tyr-D-Tyr-c[Cys-Tyr-D-Trp-Lys-Abu-Cys]-Thr-NH$_2$

Dop1-Lys(Dop1)-D-Phe-c[Cys-Tyr-D-Trp-Lys-Abu-Cys]-Thr-NH$_2$

Dop1-Lys(Dop1)-Aepa-D-Phe-c[Cys-Tyr-D-Trp-Lys-Abu-Cys]-Thr-NH$_2$

Dop1-Lys(Dop1)-c[Cys-Tyr-D-Trp-Lys-Abu-Cys]-Thr-NH$_2$

Dop1-Lys(Dop1)-Lys-D-Tyr-D-Tyr-c[Cys-Tyr-D-Trp-Lys-Abu-Cys]-Thr-NH$_2$

Dop1-Lys(Dop1)-D-Tyr-D-Tyr-c[Cys-Tyr-D-Trp-Lys-Abu-Cys]-Thr-NH$_2$

Dop1-D-Lys(Dop1)-D-Phe-c[Cys-Tyr-D-Trp-Lys-Abu-Cys]-Thr-NH$_2$

Dop1-D-Lys(Dop1)-Aepa-D-Phe-c[Cys-Tyr-D-Trp-Lys-Abu-Cys]-Thr-NH$_2$

Dop1-D-Lys(Dop1)-c[Cys-Tyr-D-Trp-Lys-Abu-Cys]-Thr-NH$_2$

Dop1-D-Lys(Dop1)-Lys-D-Tyr-D-Tyr-c[Cys-Tyr-D-Trp-Lys-Abu-Cys]-Thr-NH$_2$

Dop1-D-Lys(Dop1)-D-Tyr-D-Tyr-c[Cys-Tyr-D-Trp-Lys-Abu-Cys]-Thr-NH$_2$

Dop1-Lys(Dop1)-D-2-Nal-c[Cys-Tyr-D-Trp-Lys-Val-Cys]-Thr-NH$_2$

Dop1-Lys(Dop1)-c[Cys-Tyr-D-Trp-Lys-Val-Cys]-Thr-NH$_2$

Dop1-Lys(Dop1)-Lys-D-Tyr-D-Tyr-c[Cys-Tyr-D-Trp-Lys-Val-Cys]-Thr-NH$_2$

-continued

Dop1-Lys(Dop1)-D-Tyr-D-Tyr-c[Cys-Tyr-D-Trp-Lys-Val-Cys]-Thr-NH$_2$

Dop1-Lys(Dop1)-D-Phe-c[Cys-Tyr-D-Trp-Lys-Thr-Cys]-2-Nal-NH$_2$

Dop1-Lys(Dop1)-c[Cys-Tyr-D-Trp-Lys-Thr-Cys]-2-Nal-NH$_2$

Dop1-Lys(Dop1)-Lys-D-Tyr-D-Tyr-c[Cys-Tyr-D-Trp-Lys-Thr-Cys]-2-Nal-NH$_2$

Dop1-Lys(Dop1)-D-Tyr-D-Tyr-c[Cys-Tyr-D-Trp-Lys-Thr-Cys]-2-Nal-NH$_2$

Dop1-Lys(Dop2)-D-Phe-c[Cys-Tyr-D-Trp-Lys-Val-Cys]-Trp-NH$_2$

Dop1-Lys(Dop2)-c[Cys-Tyr-D-Trp-Lys-Val-Cys]-Trp-NH$_2$

Dop1-Lys(Dop2)-Lys-D-Tyr-D-Tyr-c[Cys-Tyr-D-Trp-Lys-Val-Cys]-Trp-NH$_2$

Dop1-Lys(Dop2)-D-Tyr-D-Tyr-c[Cys-Tyr-D-Trp-Lys-Val-Cys]-Trp-NH$_2$

Dop2-Lys(Dop2)-D-Phe-c[Cys-Tyr-D-Trp-Lys-Abu-Cys]-Thr-NH$_2$

Dop2-Lys(Dop2)-Aepa-D-Phe-c[Cys-Tyr-D-Trp-Lys-Abu-Cys]-Thr-NH$_2$

Dop2-Lys(Dop2)-c[Cys-Tyr-D-Trp-Lys-Abu-Cys]-Thr-NH$_2$

Dop2-Lys(Dop2)-Lys-D-Tyr-D-Tyr-c[Cys-Tyr-D-Trp-Lys-Abu-Cys]-Thr-NH$_2$

Dop2-Lys(Dop2)-D-Tyr-D-Tyr-c[Cys-Tyr-D-Trp-Lys-Abu-Cys]-Thr-NH$_2$

Dop2-Lys(Dop2)-Aepa-D-Tyr-D-Tyr-c[Cys-Tyr-D-Trp-Lys-Abu-Cys]-Thr-NH$_2$

Dop2-D-Lys(Dop2)-D-Phe-c[Cys-Tyr-D-Trp-Lys-Abu-Cys]-Thr-NH$_2$

Dop2-D-Lys(Dop2)-Aepa-D-Phe-c[Cys-Tyr-D-Trp-Lys-Abu-Cys]-Thr-NH$_2$

Dop2-D-Lys(Dop2)-c[Cys-Tyr-D-Trp-Lys-Abu-Cys]-Thr-NH$_2$

Dop2-D-Lys(Dop2)-Lys-D-Tyr-D-Tyr-c[Cys-Tyr-D-Trp-Lys-Abu-Cys]-Thr-NH$_2$

Dop2-D-Lys(Dop2)-D-Tyr-D-Tyr-c[Cys-Tyr-D-Trp-Lys-Abu-Cys]-Thr-NH$_2$

Dop2-D-Lys(Dop2)-Aepa-D-Tyr-D-Tyr-c[Cys-Tyr-D-Trp-Lys-Abu-Cys]-Thr-NH$_2$

Dop2-Lys(Dop2)-D-2-Nal-c[Cys-Tyr-D-Trp-Lys-Val-Cys]-Thr-NH$_2$

Dop2-Lys(Dop2)-c[Cys-Tyr-D-Trp-Lys-Val-Cys]-Thr-NH$_2$

Dop2-Lys(Dop2)-Lys-D-Tyr-D-Tyr-c[Cys-Tyr-D-Trp-Lys-Val-Cys]-Thr-NH$_2$

Dop2-Lys(Dop2)-D-Tyr-D-Tyr-c[Cys-Tyr-D-Trp-Lys-Val-Cys]-Thr-NH$_2$

Dop2-Lys(Dop2)-D-Phe-c[Cys-Tyr-D-Trp-Lys-Thr-Cys]-2-Nal-NH$_2$

Dop2-Lys(Dop2)-c[Cys-Tyr-D-Trp-Lys-Thr-Cys]-2-Nal-NH$_2$

Dop2-Lys(Dop2)-Lys-D-Tyr-D-Tyr-c[Cys-Tyr-D-Trp-Lys-Thr-Cys]-2-Nal-NH$_2$

Dop2-Lys(Dop2)-D-Tyr-D-Tyr-c[Cys-Tyr-D-Trp-Lys-Thr-Cys]-2-Nal-NH$_2$

Dop2-Lys(Dop2)-D-Phe-c[Cys-Tyr-D-Trp-Lys-Val-Cys]-Trp-NH$_2$

Dop2-Lys(Dop2)-c[Cys-Tyr-D-Trp-Lys-Val-Cys]-Trp-NH$_2$

Dop2-Lys(Dop2)-Lys-D-Tyr-D-Tyr-c[Cys-Tyr-D-Trp-Lys-Val-Cys]-Trp-NH$_2$

Dop2-Lys(Dop2)-D-Tyr-D-Tyr-c[Cys-Tyr-D-Trp-Lys-Val-Cys]-Trp-NH$_2$

Dop3-Lys(Dop3)-D-Phe-c[Cys-Tyr-D-Trp-Lys-Abu-Cys]-Thr-NH$_2$

```
Dop3-Lys(Dop3)-Aepa-D-Phe-c[Cys-Tyr-D-Trp-Lys-Abu-Cys]-Thr-NH2

Dop3-Lys(Dop3)-c[Cys-Tyr-D-Trp-Lys-Abu-Cys]-Thr-NH2

Dop3-Lys(Dop3)-Lys-D-Tyr-D-Tyr-c[Cys-Tyr-D-Trp-Lys-Abu-Cys]-Thr-
NH2

Dop3-Lys(Dop3)-D-Tyr-D-Tyr-c[Cys-Tyr-D-Trp-Lys-Abu-Cys]-Thr-NH2

Dop3-D-Lys(Dop3)-D-Phe-c[Cys-Tyr-D-Trp-Lys-Abu-Cys]-Thr-NH2

Dop3-D-Lys(Dop3)-Aepa-D-Phe-c[Cys-Tyr-D-Trp-Lys-Abu-Cys]-Thr-
NH2

Dop3-D-Lys(Dop3)-c[Cys-Tyr-D-Trp-Lys-Abu-Cys]-Thr-NH2

Dop3-D-Lys(Dop3)-Lys-D-Tyr-D-Tyr-c[Cys-Tyr-D-Trp-Lys-Abu-Cys]-
Thr-NH2

Dop3-D-Lys(Dop3)-D-Tyr-D-Tyr-c[Cys-Tyr-D-Trp-Lys-Abu-Cys]-Thr-
NH2

Dop3-Lys(Dop3)-D-2-Nal-c[Cys-Tyr-D-Trp-Lys-Val-Cys]-Thr-NH2

Dop3-Lys(Dop3)-c[Cys-Tyr-D-Trp-Lys-Val-Cys]-Thr-NH2

Dop3-Lys(Dop3)-Lys-D-Tyr-D-Tyr-c[Cys-Tyr-D-Trp-Lys-Val-Cys]-Thr-
NH2

Dop3-Lys(Dop3)-D-Tyr-D-Tyr-c[Cys-Tyr-D-Trp-Lys-Val-Cys]-Thr-NH2

Dop3-Lys(Dop3)-D-Phe-c[Cys-Tyr-D-Trp-Lys-Thr-Cys]-2-Nal-NH2

Dop3-Lys(Dop3)-c[Cys-Tyr-D-Trp-Lys-Thr-Cys]-2-Nal-NH2

Dop3-Lys(Dop3)-Lys-D-Tyr-D-Tyr-c[Cys-Tyr-D-Trp-Lys-Thr-Cys]-2-
Nal-NH2

Dop3-Lys(Dop3)-D-Tyr-D-Tyr-c[Cys-Tyr-D-Trp-Lys-Thr-Cys]-2-Nal-
NH2

Dop3-Lys(Dop3)-D-Phe-c[Cys-Tyr-D-Trp-Lys-Val-Cys]-Trp-NH2

Dop3-Lys(Dop3)-c[Cys-Tyr-D-Trp-Lys-Val-Cys]-Trp-NH2

Dop3-Lys(Dop3)-Lys-D-Tyr-D-Tyr-c[Cys-Tyr-D-Trp-Lys-Val-Cys]-Trp-
NH2

Dop3-Lys(Dop3)-D-Tyr-D-Tyr-c[Cys-Tyr-D-Trp-Lys-Val-Cys]-Trp-NH2

Dop4-Lys(Dop4)-D-Phe-c[Cys-Tyr-D-Trp-Lys-Abu-Cys]-Thr-NH2

Dop4-Lys(Dop4)-Aepa-D-Phe-c[Cys-Tyr-D-Trp-Lys-Abu-Cys]-Thr-NH2

Dop4-Lys(Dop4)-c[Cys-Tyr-D-Trp-Lys-Abu-Cys]-Thr-NH2

Dop4-Lys(Dop4)-Lys-D-Tyr-D-Tyr-c[Cys-Tyr-D-Trp-Lys-Abu-Cys]-Thr-
NH2

Dop4-Lys(Dop4)-D-Tyr-D-Tyr-c[Cys-Tyr-D-Trp-Lys-Abu-Cys]-Thr-NH2

Dop4-D-Lys(Dop4)-D-Phe-c[Cys-Tyr-D-Trp-Lys-Abu-Cys]-Thr-NH2

Dop4-D-Lys(Dop4)-Aepa-D-Phe-c[Cys-Tyr-D-Trp-Lys-Abu-Cys]-Thr-
NH2

Dop4-D-Lys(Dop4)-c[Cys-Tyr-D-Trp-Lys-Abu-Cys]-Thr-NH2

Dop4-D-Lys(Dop4)-Lys-D-Tyr-D-Tyr-c[Cys-Tyr-D-Trp-Lys-Abu-Cys]-
Thr-NH2

Dop4-D-Lys(Dop4)-D-Tyr-D-Tyr-c[Cys-Tyr-D-Trp-Lys-Abu-Cys]-Thr-
NH2

Dop4-Lys(Dop4)-D-2-Nal-c[Cys-Tyr-D-Trp-Lys-Val-Cys]-Thr-NH2

Dop4-Lys(Dop4)-c[Cys-Tyr-D-Trp-Lys-Val-Cys]-Thr-NH2

Dop4-Lys(Dop4)-Lys-D-Tyr-D-Tyr-c[Cys-Tyr-D-Trp-Lys-Val-Cys]-Thr-
NH2
```

-continued

Dop4-Lys(Dop4)-D-Tyr-D-Tyr-c[Cys-Tyr-D-Trp-Lys-Val-Cys]-Thr-NH$_2$-

Dop4-Lys(Dop4)-D-Phe-c[Cys-Tyr-D-Trp-Lys-Thr-Cys]-2-Nal-NH$_2$

Dop4-Lys(Dop4)-c[Cys-Tyr-D-Trp-Lys-Thr-Cys]-2-Nal-NH$_2$

Dop4-Lys(Dop4)-Lys-D-Tyr-D-Tyr-c[Cys-Tyr-D-Trp-Lys-Thr-Cys]-2-Nal-NH$_2$

Dop4-Lys(Dop4)-D-Tyr-D-Tyr-c[Cys-Tyr-D-Trp-Lys-Thr-Cys]-2-Nal-NH$_2$

Dop4-Lys(Dop4)-D-Phe-c[Cys-Tyr-D-Trp-Lys-Val-Cys]-Trp-NH$_2$

Dop4-Lys(Dop4)-c[Cys-Tyr-D-Trp-Lys-Val-Cys]-Trp-NH$_2$

Dop4-Lys(Dop4)-Lys-D-Tyr-D-Tyr-c[Cys-Tyr-D-Trp-Lys-Val-Cys]-Trp-NH$_2$

Dop4-Lys(Dop4)-D-Tyr-D-Tyr-c[Cys-Tyr-D-Trp-Lys-Val-Cys]-Trp-NH$_2$

Dop5-Lys(Dop5)-D-Phe-c[Cys-Tyr-D-Trp-Lys-Abu-Cys]-Thr-NH$_2$

Dop5-Lys(Dop5)-c[Cys-Tyr-D-Trp-Lys-Abu-Cys]-Thr-NH$_2$

Dop5-Lys(Dop5)-Lys-D-Tyr-D-Tyr-c[Cys-Tyr-D-Trp-Lys-Abu-Cys]-Thr-NH$_2$

Dop5-Lys(Dop5)-D-Tyr-D-Tyr-c[Cys-Tyr-D-Trp-Lys-Abu-Cys]-Thr-NH$_2$

Dop5-D-Lys(Dop5)-D-Phe-c[Cys-Tyr-D-Trp-Lys-Abu-Cys]-Thr-NH$_2$

Dop5-D-Lys(Dop5)-c[Cys-Tyr-D-Trp-Lys-Abu-Cys]-Thr-NH$_2$

Dop5-D-Lys(Dop5)-Lys-D-Tyr-D-Tyr-c[Cys-Tyr-D-Trp-Lys-Abu-Cys]-Thr-NH$_2$

Dop5-D-Lys(Dop5)-D-Tyr-D-Tyr-c[Cys-Tyr-D-Trp-Lys-Abu-Cys]-Thr-NH$_2$

Dop5-Lys(Dop5)-D-2-Nal-c[Cys-Tyr-D-Trp-Lys-Val-Cys]-Thr-NH$_2$

Dop5-Lys(Dop5)-c[Cys-Tyr-D-Trp-Lys-Val-Cys]-Thr-NH$_2$

Dop5-Lys(Dop5)-Lys-D-Tyr-D-Tyr-c[Cys-Tyr-D-Trp-Lys-Val-Cys]-Thr-NH$_2$

Dop5-Lys(Dop5)-D-Tyr-D-Tyr-c[Cys-Tyr-D-Trp-Lys-Val-Cys]-Thr-NH$_2$

Dop5-Lys(Dop5)-D-Phe-c[Cys-Tyr-D-Trp-Lys-Thr-Cys]-2Nal-NH$_2$

Dop5-Lys(Dop5)-c[Cys-Tyr-D-Trp-Lys-Thr-Cys]-2Nal-NH$_2$

Dop5-Lys(Dop5)-Lys-D-Tyr-D-Tyr-c[Cys-Tyr-D-Trp-Lys-Thr-Cys]-2-Nal-NH$_2$

Dop5-Lys(Dop5)-D-Tyr-D-Tyr-c[Cys-Tyr-D-Trp-Lys-Thr-Cys]-2-Nal-NH$_2$

Dop5-Lys(Dop5)-D-Phe-c[Cys-Tyr-D-Trp-Lys-Val-Cys]-Trp-NH$_2$

Dop5-Lys(Dop5)-c[Cys-Tyr-D-Trp-Lys-Val-Cys]-Trp-NH$_2$

Dop5-Lys(Dop5)-Lys-D-Tyr-D-Tyr-c[Cys-Tyr-D-Trp-Lys-Val-Cys]-Trp-NH$_2$

Dop5-Lys(Dop5)-D-Tyr-D-Tyr-c[Cys-Tyr-D-Trp-Lys-Val-Cys]-Trp-NH$_2$

Dop6-Lys(Dop6)-D-Phe-c[Cys-Tyr-D-Trp-Lys-Abu-Cys]-Thr-NH$_2$

Dop6-Lys(Dop6)-c[Cys-Tyr-D-Trp-Lys-Abu-Cys]-Thr-NH$_2$

Dop6-Lys(Dop6)-Lys-D-Tyr-D-Tyr-c[Cys-Tyr-D-Trp-Lys-Abu-Cys]-Thr-NH$_2$

Dop6-Lys(Dop6)-D-Tyr-D-Tyr-c[Cys-Tyr-D-Trp-Lys-Abu-Cys]-Thr-NH$_2$

Dop6-D-Lys(Dop6)-D-Phe-c[Cys-Tyr-D-Trp-Lys-Abu-Cys]-Thr-NH$_2$

Dop6-D-Lys(Dop6)-c[Cys-Tyr-D-Trp-Lys-Abu-Cys]-Thr-NH$_2$

-continued

Dop6-D-Lys(Dop6)-Lys-D-Tyr-D-Tyr-c[Cys-Tyr-D-Trp-Lys-Abu-Cys]-Thr-NH$_2$

Dop6-D-Lys(Dop6)-D-Tyr-D-Tyr-c[Cys-Tyr-D-Trp-Lys-Abu-Cys]-Thr-NH$_2$

Dop6-Lys(Dop6)-D-2-Nal-c[Cys-Tyr-D-Trp-Lys-Val-Cys]-Thr-NH$_2$

Dop6-Lys(Dop6)-c[Cys-Tyr-D-Trp-Lys-Val-Cys]-Thr-NH$_2$

Dop6-Lys(Dop6)-Lys-D-Tyr-D-Tyr-c[Cys-Tyr-D-Trp-Lys-Val-Cys]-Thr-NH$_2$

Dop6-Lys(Dop6)-D-Tyr-D-Tyr-c[Cys-Tyr-D-Trp-Lys-Val-Cys]-Thr-NH$_2$

Dop6-Lys(Dop6)-D-Phe-c[Cys-Tyr-D-Trp-Lys-Thr-Cys]-2-Nal-NH$_2$

Dop6-Lys(Dop6)-c[Cys-Tyr-D-Trp-Lys-Thr-Cys]-2-Nal-NH$_2$

Dop6-Lys(Dop6)-Lys-D-Tyr-D-Tyr-c[Cys-Tyr-D-Trp-Lys-Thr-Cys]-2-Nal-NH$_2$

Dop6-Lys(Dop6)-D-Tyr-D-Tyr-c[Cys-Tyr-D-Trp-Lys-Thr-Cys]-2-Nal-NH$_2$

Dop6-Lys(Dop6)-D-Phe-c[Cys-Tyr-D-Trp-Lys-Val-Cys]-Trp-NH$_2$

Dop6-Lys(Dop6)-c[Cys-Tyr-D-Trp-Lys-Val-Cys]-Trp-NH$_2$

Dop6-Lys(Dop6)-Lys-D-Tyr-D-Tyr-c[Cys-Tyr-D-Trp-Lys-Val-Cys]-Trp-NH$_2$

Dop6-Lys(Dop6)-D-Tyr-D-Tyr-c[Cys-Tyr-D-Trp-Lys-Val-Cys]-Trp-NH$_2$

Dop7-Lys(Dop7)-D-Phe-c[Cys-Tyr-D-Trp-Lys-Abu-Cys]-Thr-NH$_2$

Dop7-Lys(Dop7)-c[Cys-Tyr-D-Trp-Lys-Abu-Cys]-Thr-NH$_2$

Dop7-D-Lys(Dop7)-D-Phe-c[Cys-Tyr-D-Trp-Lys-Abu-Cys]-Thr-NH$_2$

Dop7-D-Lys(Dop7)-c[Cys-Tyr-D-Trp-Lys-Abu-Cys]-Thr-NH$_2$

Dop7-Lys(Dop7)-D-2-Nal-c[Cys-Tyr-D-Trp-Lys-Val-Cys]-Thr-NH$_2$

Dop7-Lys(Dop7)-c[Cys-Tyr-D-Trp-Lys-Val-Cys]-Thr-NH$_2$

Dop7-Lys(Dop7)-D-Phe-c[Cys-Tyr-D-Trp-Lys-Thr-Cys]-2-Nal-NH$_2$

Dop7-Lys(Dop7)-c[Cys-Tyr-D-Trp-Lys-Thr-Cys]-2-Nal-NH$_2$

Dop7-Lys(Dop7)-D-Phe-c[Cys-Tyr-D-Trp-Lys-Val-Cys]-Trp-NH$_2$

Dop7-Lys(Dop7)-c[Cys-Tyr-D-Trp-Lys-Val-Cys]-Trp-NH$_2$

Dop8-Lys(Dop8)-D-Phe-c[Cys-Tyr-D-Trp-Lys-Abu-Cys]-Thr-NH$_2$

Dop8-Lys(Dop8)-c[Cys-Tyr-D-Trp-Lys-Abu-Cys]-Thr-NH$_2$

Dop8-D-Lys(Dop8)-D-Phe-c[Cys-Tyr-D-Trp-Lys-Abu-Cys]-Thr-NH$_2$

Dop8-D-Lys(Dop8)-c[Cys-Tyr-D-Trp-Lys-Abu-Cys]-Thr-NH$_2$

Dop8-Lys(Dop8)-D-2-Nal-c[Cys-Tyr-D-Trp-Lys-Val-Cys]-Thr-NH$_2$

Dop8-Lys(Dop8)-c[Cys-Tyr-D-Trp-Lys-Val-Cys]-Thr-NH$_2$

Dop8-Lys(Dop8)-D-Phe-c[Cys-Tyr-D-Trp-Lys-Thr-Cys]-2-Nal-NH$_2$

Dop8-Lys(Dop8)-c[Cys-Tyr-D-Trp-Lys-Thr-Cys]-2-Nal-NH$_2$

Dop8-Lys(Dop8)-D-Phe-c[Cys-Tyr-D-Trp-Lys-Val-Cys]-Trp-NH$_2$

Dop8-Lys(Dop8)-c[Cys-Tyr-D-Trp-Lys-Val-Cys]-Trp-NH$_2$

Dop9-Lys(Dop9)-D-Phe-c[Cys-Tyr-D-Trp-Lys-Abu-Cys]-Thr-NH$_2$

Dop9-Lys(Dop9)-c[Cys-Tyr-D-Trp-Lys-Abu-Cys]-Thr-NH$_2$

Dop9-D-Lys(Dop9)-D-Phe-c[Cys-Tyr-D-Trp-Lys-Abu-Cys]-Thr-NH$_2$

-continued

Dop9-D-Lys(Dop9)-c[Cys-Tyr-D-Trp-Lys-Abu-Cys]-Thr-NH$_2$

Dop9-Lys(Dop9)-D-2-Nal-c[Cys-Tyr-D-Trp-Lys-Val-Cys]-Thr-NH$_2$

Dop9-Lys(Dop9)-c[Cys-Tyr-D-Trp-Lys-Val-Cys]-Thr-NH$_2$

Dop9-Lys(Dop9)-D-Phe-c[Cys-Tyr-D-Trp-Lys-Thr-Cys]-2-Nal-NH$_2$

Dop9-Lys(Dop9)-c[Cys-Tyr-D-Trp-Lys-Thr-Cys]-2-Nal-NH$_2$

Dop9-Lys(Dop9)-D-Phe-c[Cys-Tyr-D-Trp-Lys-Val-Cys]-Trp-NH$_2$

Dop9-Lys(Dop9)-c[Cys-Tyr-D-Trp-Lys-Val-Cys]-Trp-NH$_2$

Dop10-Lys(Dop10)-D-Phe-c[Cys-Tyr-D-Trp-Lys-Abu-Cys]-Thr-NH$_2$

Dop10-Lys(Dop10)-c[Cys-Tyr-D-Trp-Lys-Abu-Cys]-Thr-NH$_2$

Dop10-D-Lys(Dop10)-D-Phe-c[Cys-Tyr-D-Trp-Lys-Abu-Cys]-Thr-NH$_2$

Dop10-D-Lys(Dop10)-c[Cys-Tyr-D-Trp-Lys-Abu-Cys]-Thr-NH$_2$

Dop10-Lys(Dop10)-D-2-Nal-c[Cys-Tyr-D-Trp-Lys-Val-Cys]-Thr-NH$_2$

Dop10-Lys(Dop10)-c[Cys-Tyr-D-Trp-Lys-Val-Cys]-Thr-NH$_2$

Dop10-Lys(Dop10)-D-Phe-c[Cys-Tyr-D-Trp-Lys-Thr-Cys]-2-Nal-NH$_2$

Dop10-Lys(Dop10)-c[Cys-Tyr-D-Trp-Lys-Thr-Cys]-2-Nal-NH$_2$

Dop10-Lys(Dop10)-D-Phe-c[Cys-Tyr-D-Trp-Lys-Val-Cys]-Trp-NH$_2$

Dop10-Lys(Dop10)-c[Cys-Tyr-D-Trp-Lys-Val-Cys]-Trp-NH$_2$

Dop11-Lys(Dop11)-D-Phe-c[Cys-Tyr-D-Trp-Lys-Abu-Cys]-Thr-NH$_2$

Dop11-Lys(Dop11)-c[Cys-Tyr-D-Trp-Lys-Abu-Cys]-Thr-NH$_2$

Dop11-D-Lys(Dop11)-D-Phe-c[Cys-Tyr-D-Trp-Lys-Abu-Cys]-Thr-NH$_2$

Dop11-D-Lys(Dop11)-c[Cys-Tyr-D-Trp-Lys-Abu-Cys]-Thr-NH$_2$

Dop11-Lys(Dop11)-D-2-Nal-c[Cys-Tyr-D-Trp-Lys-Val-Cys]-Thr-

Dop11-Lys(Dop11)-c[Cys-Tyr-D-Trp-Lys-Val-Cys]-Thr-NH$_2$

Dop11-Lys(Dop11)-D-Phe-c[Cys-Tyr-D-Trp-Lys-Thr-Cys]-2-Nal-NH$_2$

Dop11-Lys(Dop11)-c[Cys-Tyr-D-Trp-Lys-Thr-Cys]-2-Nal-NH$_2$

Dop11-Lys(Dop11)-D-Phe-c[Cys-Tyr-D-Trp-Lys-Val-Cys]-Trp-NH$_2$

Dop11-Lys(Dop11)-c[Cys-Tyr-D-Trp-Lys-Val-Cys]-Trp-NH$_2$

Dop12-Lys(Dop12)-D-Phe-c[Cys-Tyr-D-Trp-Lys-Abu-Cys]-Thr-NH$_2$

Dop12-Lys(Dop12)-c[Cys-Tyr-D-Trp-Lys-Abu-Cys]-Thr-NH$_2$

Dop12-D-Lys(Dop12)-D-Phe-c[Cys-Tyr-D-Trp-Lys-Abu-Cys]-Thr-NH$_2$

Dop12-D-Lys(Dop12)-c[Cys-Tyr-D-Trp-Lys-Abu-Cys]-Thr-NH$_2$

Dop12-Lys(Dop12)-D-2-Nal-c[Cys-Tyr-D-Trp-Lys-Val-Cys]-Thr-NH$_2$

Dop12-Lys(Dop12)-c[Cys-Tyr-D-Trp-Lys-Val-Cys]-Thr-NH$_2$

Dop12-Lys(Dop12)-D-Phe-c[Cys-Tyr-D-Trp-Lys-Thr-Cys]-2-Nal-NH$_2$

Dop12-Lys(Dop12)-c[Cys-Tyr-D-Trp-Lys-Thr-Cys]-2-Nal-NH$_2$

Dop12-Lys(Dop12)-D-Phe-c[Cys-Tyr-D-Trp-Lys-Val-Cys]-Trp-NH$_2$

Dop12-Lys(Dop12)-c[Cys-Tyr-D-Trp-Lys-Val-Cys]-Trp-NH$_2$

Dop13-Lys(Dop13)-D-Phe-c[Cys-Tyr-D-Trp-Lys-Abu-Cys]-Thr-NH$_2$

Dop13-Lys(Dop13)-c[Cys-Tyr-D-Trp-Lys-Abu-Cys]-Thr-NH$_2$

Dop13-D-Lys(Dop10)-D-Phe-c[Cys-Tyr-D-Trp-Lys-Abu-Cys]-Thr-NH$_2$

Dop13-D-Lys(Dop13)-c[Cys-Tyr-D-Trp-Lys-Abu-Cys]-Thr-NH$_2$

-continued

Dop13-Lys(Dop13)-D-2-Nal-c[Cys-Tyr-D-Trp-Lys-Val-Cys]-Thr-NH$_2$

Dop13-Lys(Dop13)-c[Cys-Tyr-D-Trp-Lys-Val-Cys]-Thr-NH$_2$

Dop13-Lys(Dop13)-D-Phe-c[Cys-Tyr-D-Trp-Lys-Thr-Cys]-2-Nal-NH$_2$

Dop13-Lys(Dop13)-c[Cys-Tyr-D-Trp-Lys-Thr-Cys]-2-Nal-NH$_2$

Dop13-Lys(Dop13)-D-Phe-c[Cys-Tyr-D-Trp-Lys-Val-Cys]-Trp-NH$_2$

Dop13-Lys(Dop13)-c[Cys-Tyr-D-Trp-Lys-Val-Cys]-Trp-NH$_2$

Dop1-Lys(Dop1)-Caeg-c[D-Cys-3-Pal-D-Trp-Lys-D-Cys]-Thr(Bzl)-Tyr-NH$_2$

Dop1-Lys(Dop1)-Caeg-c[D-Cys-Phe-D-Trp-Lys-D-Cys]-Ser(Bzl)-Tyr-NH$_2$

Dop1-D-Lys(Dop1)-Caeg-c[D-Cys-3-Pal-D-Trp-Lys-D-Cys]-Thr(Bzl)-Tyr-NH$_2$

Dop1-D-Lys(Dop1)-Caeg-c[D-Cys-Phe-D-Trp-Lys-D-Cys]-Ser(Bzl)-Tyr-NH$_2$

Dop1-Lys(Dop1)-Lys-Caeg-c[D-Cys-3-Pal-D-Trp-Lys-D-Cys]-Thr(Bzl)-Tyr-NH$_2$

Dop1-Lys(Dop1)-Lys-Caeg-c[D-Cys-Phe-D-Trp-Lys-D-Cys]-Ser(Bzl)-Tyr-NH$_2$

Dop1-D-Lys(Dop1)-Lys-Caeg-c[D-Cys-3-Pal-D-Trp-Lys-D-Cys]-Thr(Bzl)-Tyr-NH$_2$

Dop1-D-Lys(Dop1)-Lys-Caeg-c[D-Cys-Phe-D-Trp-Lys-D-Cys]-Ser(Bzl)-Tyr-NH$_2$

Dop1-Lys(Dop1)-Aepa-Caeg-c[D-Cys-3-Pal-D-Trp-Lys-D-Cys]-Thr(Bzl)-Tyr-NH$_2$

Dop1-Lys(Dop1)-Aepa-Caeg-c[D-Cys-Phe-D-Trp-Lys-D-Cys]-Ser(Bzl)-Tyr-NH$_2$

Dop1-D-Lys(Dop1)-Aepa-Caeg-c[D-Cys-3-Pal-D-Trp-Lys-D-Cys]-Thr(Bzl)-Tyr-NH$_2$

Dop1-D-Lys(Dop1)-Aepa-Caeg-c[D-Cys-Phe-D-Trp-Lys-D-Cys]-Ser(Bzl)-Tyr-NH$_2$

Dop1-Lys(Dop1)-Lys-Aepa-Caeg-c[D-Cys-3-Pal-D-Trp-Lys-D-Cys]-Thr(Bzl)-Tyr-NH$_2$

Dop1-Lys(Dop1)-Lys-Aepa-Caeg-c[D-Cys-Phe-D-Trp-Lys-D-Cys]-Ser(Bzl)-Tyr-NH$_2$

Dop1-D-Lys(Dop1)-Lys-Aepa-Caeg-c[D-Cys-3-Pal-D-Trp-Lys-D-Cys]-Thr(Bzl)-Tyr-NH$_2$ Dop1-D-Lys(Dop1)-Lys-Aepa-Caeg-c[D-Cys-Phe-D-Trp-Lys-D-Cys]-Ser(Bzl)-Tyr-NH$_2$ Dop2-Lys(Dop2)-Caeg-c[D-Cys-3-Pal-D-Trp-Lys-D-Cys]-Thr(Bzl)-Tyr-NH$_2$ Dop2-Lys(Dop2)-Caeg-c[D-Cys-Phe-D-Trp-Lys-D-Cys]-Ser(Bzl)-Tyr-NH$_2$ Dop2-D-Lys(Dop2)-Caeg-c[D-Cys-3-Pal-D-Trp-Lys-D-Cys]-Thr(Bzl)-Tyr-NH$_2$ Dop2-D-Lys(Dop2)-Caeg-c[D-Cys-Phe-D-Trp-Lys-D-Cys]-Ser(Bzl)-Tyr-NH$_2$ Dop2-Lys(Dop2)-Lys-Caeg-c[D-Cys-3-Pal-D-Trp-Lys-D-Cys]-Thr(Bzl)-Tyr-NH$_2$ Dop2-Lys(Dop2)-Lys-Caeg-c[D-Cys-Phe-D-Trp-Lys-D-Cys]-Ser(Bzl)-Tyr-NH$_2$ -continued Dop2-D-Lys(Dop2)-Lys-Caeg-c[D-Cys-3-Pal-D-Trp-Lys-D-Cys]-Thr(Bzl)-Tyr-NH$_2$ Dop2-D-Lys(Dop2)-Lys-Caeg-c[D-Cys-Phe-D-Trp-Lys-D-Cys]-Ser(Bzl)-Tyr-NH$_2$ Dop2-Lys(Dop2)-Aepa-Caeg-c[D-Cys-3-Pal-D-Trp-Lys-D-Cys]-Thr(Bzl)-Tyr-NH$_2$ Dop2-Lys(Dop2)-Aepa-Caeg-c[D-Cys-Phe-D-Trp-Lys-D-Cys]-Ser(Bzl)-Tyr-NH$_2$ Dop2-D-Lys(Dop2)-Aepa-Caeg-c[D-Cys-3-Pal-D-Trp-Lys-D-Cys]-Thr(Bzl)-Tyr-NH$_2$ Dop2-D-Lys(Dop2)-Aepa-Caeg-c[D-Cys-Phe-D-Trp-Lys-D-Cys]-Ser(Bzl)-Tyr-NH$_2$ Dop2-Lys(Dop2)-Lys-Aepa-Caeg-c[D-Cys-3-Pal-D-Trp-Lys-D-Cys]-Thr(Bzl)-Tyr-NH$_2$ Dop2-Lys(Dop2)-Lys-Aepa-Caeg-c[D-Cys-Phe-D-Trp-Lys-D-Cys]-Ser(Bzl)-Tyr-NH$_2$ Dop2-D-Lys(Dop2)-Lys-Aepa-Caeg-c[D-Cys-3-Pal-D-Trp-Lys-D-Cys]-Thr(Bzl)-Tyr-NH$_2$ Dop2-D-Lys(Dop2)-Lys-Aepa-Caeg-c[D-Cys-Phe-D-Trp-Lys-D-Cys]-Ser(Bzl)-Tyr-NH$_2$ Dop3-Lys(Dop3)-Caeg-c[D-Cys-3-Pal-D-Trp-Lys-D-Cys]-Thr(Bzl)-Tyr-NH$_2$ Dop3-Lys(Dop3)-Caeg-c[D-Cys-Phe-D-Trp-Lys-D-Cys]-Ser(Bzl)-Tyr-NH$_2$ Dop3-Lys(Dop3)-Lys-Caeg-c[D-Cys-3-Pal-D-Trp-Lys-D-Cys]-Thr(Bzl)-Tyr-NH$_2$ Dop3-Lys(Dop3)-Lys-Caeg-c[D-Cys-Phe-D-Trp-Lys-D-Cys]-Ser(Bzl)-Tyr-NH$_2$ Dop3-Lys(Dop3)-Aepa-Caeg-c[D-Cys-3-Pal-D-Trp-Lys-D-Cys]-Thr(Bzl)-Tyr-NH$_2$ Dop3-Lys(Dop3)-Aepa-Caeg-c[D-Cys-Phe-D-Trp-Lys-D-Cys]-Ser(Bzl)-Tyr-NH$_2$ Dop3-D-Lys(Dop3)-Caeg-c[D-Cys-3-Pal-D-Trp-Lys-D-Cys]-Thr(Bzl)-Tyr-NH$_2$ Dop3-D-Lys(Dop3)-Caeg-c[D-Cys-Phe-D-Trp-Lys-D-Cys]-Ser(Bzl)-Tyr-NH$_2$ Dop3-D-Lys(Dop3)-Lys-Caeg-c[D-Cys-3-Pal-D-Trp-Lys-D-Cys]-Thr(Bzl)-Tyr-NH$_2$ Dop3-D-Lys(Dop3)-Lys-Caeg-c[D-Cys-Phe-D-Trp-Lys-D-Cys]-Ser(Bzl)-Tyr-NH$_2$ Dop3-D-Lys(Dop3)-Aepa-Caeg-c[D-Cys-3-Pal-D-Trp-Lys-D-Cys]-Thr(Bzl)-Tyr-NH$_2$ Dop3-D-Lys(Dop3)-Aepa-Caeg-c[D-Cys-Phe-D-Trp-Lys-D-Cys]-Ser(Bzl)-Tyr-NH$_2$ Dop4-Lys(Dop4)-Caeg-c[D-Cys-3-Pal-D-Trp-Lys-D-Cys]-Thr(Bzl)-Tyr-NH$_2$ Dop4-Lys(Dop4)-Caeg-c[D-Cys-Phe-D-Trp-Lys-D-Cys]-Ser(Bzl)-Tyr-NH$_2$ Dop4-Lys(Dop4)-Lys-Caeg-c[D-Cys-3-Pal-D-Trp-Lys-D-Cys]-Thr(Bzl)-Tyr-NH$_2$ Dop4-Lys(Dop4)-Lys-Caeg-c[D-Cys-Phe-D-Trp-Lys-D-Cys]-Ser(Bzl)-Tyr-NH$_2$ Dop4-Lys(Dop4)-Aepa-Caeg-c[D-Cys-3-Pal-D-Trp-Lys-D-Cys]-Thr(Bzl)-Tyr-NH$_2$ -continued Dop4-Lys(Dop4)-Aepa-Caeg-c[D-Cys-Phe-D-Trp-Lys-D-Cys]-Ser(Bzl)-Tyr-NH$_2$ Dop4-Lys(Dop4)-Lys-Aepa-Caeg-c[D-Cys-3-Pal-D-Trp-Lys-D-Cys]-Thr(Bzl)-Tyr-NH$_2$ Dop4-Lys(Dop4)-Lys-Aepa-Caeg-c[D-Cys-Phe-D-Trp-Lys-D-Cys]-Ser(Bzl)-Tyr-NH$_2$ Dop4-D-Lys(Dop4)-Caeg-c[D-Cys-3-Pal-D-Trp-Lys-D-Cys]-Thr(Bzl)-Tyr-NH$_2$ Dop4-D-Lys(Dop4)-Caeg-c[D-Cys-Phe-D-Trp-Lys-D-Cys]-Ser(Bzl)-Tyr-NH$_2$ Dop4-D-Lys(Dop4)-Lys-Caeg-c[D-Cys-3-Pal-D-Trp-Lys-D-Cys]-Thr(Bzl)-Tyr-NH$_2$ Dop4-D-Lys(Dop4)-Lys-Caeg-c[D-Cys-Phe-D-Trp-Lys-D-Cys]-Ser(Bzl)-Tyr-NH$_2$ Dop4-D-Lys(Dop4)-Aepa-Caeg-c[D-Cys-3-Pal-D-Trp-Lys-D-Cys]-Thr(Bzl)-Tyr-NH$_2$ Dop4-D-Lys(Dop4)-Aepa-Caeg-c[D-Cys-Phe-D-Trp-Lys-D-Cys]-Ser(Bzl)-Tyr-NH$_2$ Dop4-D-Lys(Dop4)-Lys-Aepa-Caeg-c[D-Cys-3-Pal-D-Trp-Lys-D-Cys]-Thr(Bzl)-Tyr-NH$_2$ Dop4-D-Lys(Dop4)-Lys-Aepa-Caeg-c[D-Cys-Phe-D-Trp-Lys-D-Cys]-Ser(Bzl)-Tyr-NH$_2$ Dop5-Lys(Dop5)-Caeg-c[D-Cys-3-Pal-D-Trp-Lys-D-Cys]-Thr(Bzl)-Tyr-NH$_2$ Dop5-Lys(Dop5)-Caeg-c[D-Cys-Phe-D-Trp-Lys-D-Cys]-Ser(Bzl)-Tyr-NH$_2$ Dop5-D-Lys(Dop5)-Caeg-c[D-Cys-3-Pal-D-Trp-Lys-D-Cys]-Thr(Bzl)-Tyr-NH$_2$ Dop5-D-Lys(Dop5)-Caeg-c[D-Cys-Phe-D-Trp-Lys-D-Cys]-Ser(Bzl)-Tyr-NH$_2$ Dop5-Lys(Dop5)-Lys-Caeg-c[D-Cys-3-Pal-D-Trp-Lys-D-Cys]-Thr(Bzl)-Tyr-NH$_2$ Dop5-Lys(Dop5)-Lys-Caeg-c[D-Cys-Phe-D-Trp-Lys-D-Cys]-Ser(Bzl)-Tyr-NH$_2$ Dop5-D-Lys(Dop5)-Lys-Caeg-c[D-Cys-3-Pal-D-Trp-Lys-D-Cys]-Thr(Bzl)-Tyr-NH$_2$ Dop5-D-Lys(Dop5)-Lys-Caeg-c[D-Cys-Phe-D-Trp-Lys-D-Cys]-Ser(Bzl)-Tyr-NH$_2$ Dop6-Lys(Dop6)-Caeg-c[D-Cys-3-Pal-D-Trp-Lys-D-Cys]-Thr(Bzl)-Tyr-NH$_2$ Dop6-Lys(Dop6)-Caeg-c[D-Cys-Phe-D-Trp-Lys-D-Cys]-Ser(Bzl)-Tyr-NH$_2$ Dop6-D-Lys(Dop6)-Caeg-c[D-Cys-3-Pal-D-Trp-Lys-D-Cys]-Thr(Bzl)-Tyr-NH$_2$ Dop6-D-Lys(Dop6)-Caeg-c[D-Cys-Phe-D-Trp-Lys-D-Cys]-Ser(Bzl)-Tyr-NH$_2$ Dop6-Lys(Dop6)-Lys-Caeg-c[D-Cys-3-Pal-D-Trp-Lys-D-Cys]-Thr(Bzl)-Tyr-NH$_2$ Dop6-Lys(Dop6)-Lys-Caeg-c[D-Cys-Phe-D-Trp-Lys-D-Cys]-Ser(Bzl)-Tyr-NH$_2$ Dop6-D-Lys(Dop6)-Lys-Caeg-c[D-Cys-3-Pal-D-Trp-Lys-D-Cys]-Thr(Bzl)-Tyr-NH$_2$ Dop6-D-Lys(Dop6)-Lys-Caeg-c[D-Cys-Phe-D-Trp-Lys-D-Cys]-Ser(Bzl)-Tyr-NH$_2$ -continued Dop7-Lys(Dop7)-Caeg-c[D-Cys-3-Pal-D-Trp-Lys-D-Cys]-Thr(Bzl)-Tyr-NH$_2$ Dop7-Lys(Dop7)-Caeg-c[D-Cys-Phe-D-Trp-Lys-D-Cys]-Ser(Bzl)-Tyr-NH$_2$ Dop7-Lys(Dop7)-Lys-Caeg-c[D-Cys-3-Pal-D-Trp-Lys-D-Cys]-Thr(Bzl)-Tyr-NH$_2$ Dop7-Lys(Dop7)-Lys-Caeg-c[D-Cys-Phe-D-Trp-Lys-D-Cys]-Ser(Bzl)-Tyr-NH$_2$ Dop8-Lys(Dop8)-Caeg-c[D-Cys-3-Pal-D-Trp-Lys-D-Cys]-Thr(Bzl)-Tyr-NH$_2$ Dop8-Lys(Dop8)-Caeg-c[D-Cys-Phe-D-Trp-Lys-D-Cys]-Ser(Bzl)-Tyr-NH$_2$ Dop8-Lys(Dop8)-Lys-Caeg-c[D-Cys-3-Pal-D-Trp-Lys-D-Cys]-Thr(Bzl)-Tyr-NH$_2$ Dop8-Lys(Dop8)-Lys-Caeg-c[D-Cys-Phe-D-Trp-Lys-D-Cys]-Ser(Bzl)-Tyr-NH$_2$ Dop9-Lys(Dop9)-Caeg-c[D-Cys-3-Pal-D-Trp-Lys-D-Cys]-Thr(Bzl)-Tyr-NH$_2$ Dop9-Lys(Dop9)-Caeg-c[D-Cys-Phe-D-Trp-Lys-D-Cys]-Ser(Bzl)-Tyr-NH$_2$ Dop9-Lys(Dop9)-Lys-Caeg-c[D-Cys-3-Pal-D-Trp-Lys-D-Cys]-Thr(Bzl)-Tyr-NH$_2$ Dop9-Lys(Dop9)-Lys-Caeg-c[D-Cys-Phe-D-Trp-Lys-D-Cys]-Ser(Bzl)-Tyr-NH$_2$ Dop10-Lys(Dop10)-Caeg-c[D-Cys-3-Pal-D-Trp-Lys-D-Cys]-Thr(Bzl)-Tyr-NH$_2$ Dop10-Lys(Dop10)-Caeg-c[D-Cys-Phe-D-Trp-Lys-D-Cys]-Ser(Bzl)-Tyr-NH$_2$ Dop10-Lys(Dop10)-Lys-Caeg-c[D-Cys-3-Pal-D-Trp-Lys-D-Cys]-Thr(Bzl)-Tyr-NH$_2$ Dop10-Lys(Dop10)-Lys-Caeg-c[D-Cys-Phe-D-Trp-Lys-D-Cys]-Ser(Bzl)-Tyr-NH$_2$ Dop11-Lys(Dop11)-Caeg-c[D-Cys-3-Pal-D-Trp-Lys-D-Cys]-Thr(Bzl)-Tyr-NH$_2$ Dop11-Lys(Dop11)-Caeg-c[D-Cys-Phe-D-Trp-Lys-D-Cys]-Ser(Bzl)-Tyr-NH$_2$ Dop11-Lys(Dop11)-Lys-Caeg-c[D-Cys-3-Pal-D-Trp-Lys-D-Cys]-Thr(Bzl)-Tyr-NH$_2$ Dop11-Lys(Dop11)-Lys-Caeg-c[D-Cys-Phe-D-Trp-Lys-D-Cys]-Ser(Bzl)-Tyr-NH$_2$ Dop12-Lys(Dop12)-Caeg-c[D-Cys-3-Pal-D-Trp-Lys-D-Cys]-Thr(Bzl)-Tyr-NH$_2$ Dop12-Lys(Dop12)-Caeg-c[D-Cys-Phe-D-Trp-Lys-D-Cys]-Ser(Bzl)-Tyr-NH$_2$ Dop12-Lys(Dop12)-Lys-Caeg-c[D-Cys-3-Pal-D-Trp-Lys-D-Cys]-Thr(Bzl)-Tyr-NH$_2$ Dop12-Lys(Dop12)-Lys-Caeg-c[D-Cys-Phe-D-Trp-Lys-D-Cys]-Ser(Bzl)-Tyr-NH$_2$ Dop13-Lys(Dop13)-Caeg-c[D-Cys-3-Pal-D-Trp-Lys-D-Cys]-Thr(Bzl)-Tyr-NH$_2$ Dop13-Lys(Dop13)-Caeg-c[D-Cys-Phe-D-Trp-Lys-D-Cys]-Ser(Bzl)-Tyr-NH$_2$ Dop13-Lys(Dop13)-Lys-Caeg-c[D-Cys-3-Pal-D-Trp-Lys-D-Cys]-Thr(Bzl)-Tyr-NH$_2$ -continued Dop13-Lys(Dop13)-Lys-Caeg-c[D-Cys-Phe-D-Trp-Lys-D-Cys]-Ser(Bzl)-Tyr-NH$_2$ Dop1-Lys(Dop1)-c[Cys-Phe-Phe-D-Trp-Lys-Thr-Phe-Cys]-NH$_2$ Dop1-Lys(Dop1)-D-Phe-c[Cys-Phe-(N-Me)D-Trp-Lys-Thr-Cys]-Thr-NH$_2$ Dop1-D-Lys(Dop1)-c[Cys-Phe-Phe-D-Trp-Lys-Thr-Phe-Cys]-NH$_2$ Dop1-D-Lys(Dop1)-D-Phe-c[Cys-Phe-(N-Me)D-Trp-Lys-Thr-Cys]-Thr-NH$_2$ Dop1-Lys(Dop1)-c[Cys-Phe-(N-Me)D-Trp-Lys-Thr-Cys]-Thr-NH$_2$ Dop1-D-Lys(Dop1)-c[Cys-Phe-(N-Me)D-Trp-Lys-Thr-Cys]-Thr-NH$_2$ Dop2-Lys(Dop2)-c[Cys-Phe-Phe-D-Trp-Lys-Thr-Phe-Cys]-NH$_2$ Dop2-Lys(Dop2)-D-Phe-c[Cys-Phe-(N-Me)D-Trp-Lys-Thr-Cys]-Thr-NH$_2$ Dop2-D-Lys(Dop2)-c[Cys-Phe-Phe-D-Trp-Lys-Thr-Phe-Cys]-NH$_2$ Dop2-D-Lys(Dop2)-D-Phe-c[Cys-Phe-(N-Me)D-Trp-Lys-Thr-Cys]-Thr-NH$_2$ Dop2-Lys(Dop2)-c[Cys-Phe-(N-Me)D-Trp-Lys-Thr-Cys]-Thr-NH$_2$ Dop2-D-Lys(Dop2)-c[Cys-Phe-(N-Me)D-Trp-Lys-Thr-Cys]-Thr-NH$_2$ Dop3-Lys(Dop3)-c[Cys-Phe-Phe-D-Trp-Lys-Thr-Phe-Cys]-NH$_2$ Dop3-Lys(Dop3)-D-Phe-c[Cys-Phe-(N-Me)D-Trp-Lys-Thr-Cys]-Thr-NH$_2$ Dop3-Lys(Dop3)-c[Cys-Phe-(N-Me)D-Trp-Lys-Thr-Cys]-Thr-NH$_2$ Dop4-Lys(Dop4)-c[Cys-Phe-Phe-D-Trp-Lys-Thr-Phe-Cys]-NH$_2$ Dop4-Lys(Dop4)-D-Phe-c[Cys-Phe-(N-Me)D-Trp-Lys-Thr-Cys]-Thr-NH$_2$ Dop4-Lys(Dop4)-c[Cys-Phe-(N-Me)D-Trp-Lys-Thr-Cys]-Thr-NH$_2$ Dop5-Lys(Dop5)-c[Cys-Phe-Phe-D-Trp-Lys-Thr-Phe-Cys]-NH$_2$ Dop5-Lys(Dop5)-D-Phe-c[Cys-Phe-(N-Me)D-Trp-Lys-Thr-Cys]-Thr-NH$_2$ Dop5-D-Lys(Dop5)-c[Cys-Phe-Phe-D-Trp-Lys-Thr-Phe-Cys]-NH$_2$ Dop5-D-Lys(Dop5)-D-Phe-c[Cys-Phe-(N-Me)D-Trp-Lys-Thr-Cys]-Thr-NH$_2$ Dop5-Lys(Dop5)-c[Cys-Phe-(N-Me)D-Trp-Lys-Thr-Cys]-Thr-NH$_2$ Dop5-D-Lys(Dop5)-c[Cys-Phe-(N-Me)D-Trp-Lys-Thr-Cys]-Thr-NH$_2$ Dop6-Lys(Dop6)-c[Cys-Phe-Phe-D-Trp-Lys-Thr-Phe-Cys]-NH$_2$ Dop6-Lys(Dop6)-D-Phe-c[Cys-Phe-(N-Me)D-Trp-Lys-Thr-Cys]-Thr-NH$_2$ Dop6-D-Lys(Dop6)-c[Cys-Phe-Phe-D-Trp-Lys-Thr-Phe-Cys]-NH$_2$ Dop6-D-Lys(Dop6)-D-Phe-c[Cys-Phe-(N-Me)D-Trp-Lys-Thr-Cys]-Thr-NH$_2$ Dop6-Lys(Dop6)-c[Cys-Phe-(N-Me)D-Trp-Lys-Thr-Cys]-Thr-NH$_2$ Dop6-D-Lys(Dop6)-c[Cys-Phe-(N-Me)D-Trp-Lys-Thr-Cys]-Thr-NH$_2$ Dop7-Lys(Dop7)-c[Cys-Phe-Phe-D-Trp-Lys-Thr-Phe-Cys]-NH$_2$ Dop7-Lys(Dop7)-D-Phe-c[Cys-Phe-(N-Me)D-Trp-Lys-Thr-Cys]-Thr-NH$_2$ Dop7-Lys(Dop7)-c[Cys-Phe-(N-Me)D-Trp-Lys-Thr-Cys]-Thr-NH$_2$ Dop8-Lys(Dop8)-c[Cys-Phe-Phe-D-Trp-Lys-Thr-Phe-Cys]-NH$_2$ Dop8-Lys(Dop8)-D-Phe-c[Cys-Phe-(N-Me)D-Trp-Lys-Thr-Cys]-Thr-NH$_2$ Dop9-Lys(Dop9)-c[Cys-Phe-Phe-D-Trp-Lys-Thr-Phe-Cys]-NH$_2$ Dop9-Lys(Dop9)-D-Phe-c[Cys-Phe-(N-Me)D-Trp-Lys-Thr-Cys]-Thr-NH$_2$ -continued Dop10-Lys(Dop10)-c[Cys-Phe-Phe-D-Trp-Lys-Thr-Phe-Cys]-NH$_2$ Dop10-Lys(Dop10)-D-Phe-c[Cys-Phe-(N-Me)D-Trp-Lys-Thr-Cys]-Thr-NH$_2$ Dop11-Lys(Dop11)-c[Cys-Phe-Phe-D-Trp-Lys-Thr-Phe-Cys]-NH$_2$ Dop11-Lys(Dop11)-D-Phe-c[Cys-Phe-(N-Me)D-Trp-Lys-Thr-Cys]-Thr-NH$_2$ Dop12-Lys(Dop12)-c[Cys-Phe-Phe-D-Trp-Lys-Thr-Phe-Cys]-NH$_2$ Dop12-Lys(Dop12)-D-Phe-c[Cys-Phe-(N-Me)D-Trp-Lys-Thr-Cys]-Thr-NH$_2$ Dop13-Lys(Dop13)-c[Cys-Phe-Phe-D-Trp-Lys-Thr-Phe-Cys]-NH$_2$ Dop13-Lys(Dop13)-D-Phe-c[Cys-Phe-(N-Me)D-Trp-Lys-Thr-Cys]-Thr-NH$_2$ Dop1-D-Phe-c[Cys-3-I-Tyr(Dop1)-D-Trp-Lys-Val-Cys]-Thr-NH$_2$ Dop1-D-Phe-Doc-D-Phe-c[Cys-3-I-Tyr(Dop1)-D-Trp-Lys-Val-Cys]-Thr-NH$_2$ Dop1-D-Lys(Dop1)-D-Phe-c[Cys-3-I-Tyr-D-Trp-Lys-Thr-Cys]-Thr-NH$_2$ Dop1-D-Lys(Dop1)-Aepa-D-Phe-c[Cys-3-I-Tyr-D-Trp-Lys-Thr-Cys]-Thr-NH$_2$ Dop1-Lys(Dop1)-D-Tyr-D-Tyr-c[Cys-3-I-Tyr-D-Trp-Lys-Thr-Cys]-Thr-NH$_2$ Dop1-Lys(Dop1)-D-Phe-c[Cys-3-I-Tyr-D-Trp-Lys-Thr-Cys]-Thr-NH$_2$ Dop1-Lys(Dop1)-Aepa-D-Phe-c[Cys-3-I-Tyr-D-Trp-Lys-Thr-Cys]-Thr-NH$_2$ Dop1-D-Lys(Dop1)-c[Cys-3-I-Tyr-D-Trp-Lys-Thr-Cys]-Thr-NH$_2$ Dop1-Lys(Dop1)-c[Cys-3-I-Tyr-D-Trp-Lys-Thr-Cys]-Thr-NH$_2$ Dop1-Lys(Dop1)-Lys-D-Tyr-D-Tyr-c[Cys-3-I-Tyr-D-Trp-Lys-Thr-Cys]-Thr-NH$_2$ Dop1-D-Lys(Dop1)-D-Tyr-D-Tyr-c[Cys-3-I-Tyr-D-Trp-Lys-Thr-Cys]-Thr-NH$_2$ Dop1-D-Lys(Dop1)-Lys-D-Tyr-D-Tyr-c[Cys-3-I-Tyr-D-Trp-Lys-Thr-Cys]-Thr-NH$_2$ Dop1-D-Lys(Dop1)-D-Phe-c[Cys-3-I-Tyr-D-Trp-Lys-Abu-Cys]-Thr-NH$_2$ Dop1-D-Lys(Dop1)-Aepa-D-Phe-c[Cys-3-I-Tyr-D-Trp-Lys-Abu-Cys]-Thr-NH$_2$ Dop1-Lys(Dop1)-D-Tyr-D-Tyr-c[Cys-3-I-Tyr-D-Trp-Lys-Abu-Cys]-Thr-NH$_2$ Dop1-Lys(Dop1)-D-Phe-c[Cys-3-I-Tyr-D-Trp-Lys-Abu-Cys]-Thr-NH$_2$ Dop1-Lys(Dop1)-Aepa-D-Phe-c[Cys-3-I-Tyr-D-Trp-Lys-Abu-Cys]-Thr-NH$_2$ Dop1-D-Lys(Dop1)-c[Cys-3-I-Tyr-D-Trp-Lys-Abu-Cys]-Thr-NH$_2$ Dop1-Lys(Dop1)-c[Cys-3-I-Tyr-D-Trp-Lys-Abu-Cys]-Thr-NH$_2$ Dop1-Lys(Dop1)-Lys-D-Tyr-D-Tyr-c[Cys-3-I-Tyr-D-Trp-Lys-Abu-Cys]-Thr-NH$_2$ Dop1-D-Lys(Dop1)-D-Tyr-D-Tyr-c[Cys-3-I-Tyr-D-Trp-Lys-Abu-Cys]-Thr-NH$_2$ Dop1-D-Lys(Dop1)-Lys-D-Tyr-D-Tyr-c[Cys-3-I-Tyr-D-Trp-Lys-Abu-Cys]-Thr-NH$_2$ Dop1-D-Lys(Dop1)-D-Phe-c[Cys-3-I-Tyr-D-Trp-Lys-Val-Cys]-Thr-NH$_2$ Dop1-D-Lys(Dop1)-Aepa-D-Phe-c[Cys-3-I-Tyr-D-Trp-Lys-Val-Cys]-Thr-NH$_2$ -continued Dop1-Lys(Dop1)-D-Tyr-D-Tyr-c[Cys-3-I-Tyr-D-Trp-Lys-Val-Cys]-Thr-NH$_2$ Dop1-Lys(Dop1)-D-Phe-c[Cys-I-Tyr-D-Trp-Lys-Val-Cys]-Thr-NH$_2$ Dop1-Lys(Dop1)-Aepa-D-Phe-c[Cys-3-I-Tyr-D-Trp-Lys-Val-Cys]-Thr-NH$_2$ Dop1-D-Lys(Dop1)-c[Cys-3-I-Tyr-D-Trp-Lys-Val-Cys]-Thr-NH$_2$ Dop1-Lys(Dop1)-c[Cys-3-I-Tyr-D-Trp-Lys-Val-Cys]-Thr-NH$_2$ Dop1-Lys(Dop1)-Lys-D-Tyr-D-Tyr-c[Cys-3-I-Tyr-D-Trp-Lys-Val-Cys]-Thr-NH$_2$ Dop1-D-Lys(Dop1)-D-Tyr-D-Tyr-c[Cys-3-I-Tyr-D-Trp-Lys-Val-Cys]-Thr-NH$_2$ Dop1-D-Lys(Dop1)-Lys-D-Tyr-D-Tyr-c[Cys-3-I-Tyr-D-Trp-Lys-Val-Cys]-Thr-NH$_2$ Dop2-D-Phe-c[Cys-3-I-Tyr(Dop2)-D-Trp-Lys-Val-Cys]-Thr-NH$_2$ Dop2-Lys(Dop2)-D-Tyr-D-Tyr-c[Cys-3-I-Tyr-D-Trp-Lys-Thr-Cys]-Thr-NH$_2$ Dop2-Lys(Dop2)-Aepa-D-Tyr-D-Tyr-c[Cys-3-I-Tyr-D-Trp-Lys-Thr-Cys]-Thr-NH$_2$ Dop2-Lys(Dop2)-D-Phe-c[Cys-3-I-Tyr-D-Trp-Lys-Thr-Cys]-Thr-NH$_2$ Dop2-Lys(Dop2)-Aepa-D-Phe-c[Cys-3-I-Tyr-D-Trp-Lys-Thr-Cys]-Thr-NH$_2$ Dop2-D-Lys(Dop2)-D-Phe-c[Cys-3-I-Tyr-D-Trp-Lys-Thr-Cys]-Thr-NH$_2$ Dop2-D-Lys(Dop2)-Aepa-D-Phe-c[Cys-3-I-Tyr-D-Trp-Lys-Thr-Cys]-Thr-NH$_2$ Dop2-D-Lys(Dop2)-c[Cys-3-I-Tyr-D-Trp-Lys-Thr-Cys]-Thr-NH$_2$ Dop2-Lys(Dop2)-c[Cys-3-I-Tyr-D-Trp-Lys-Thr-Cys]-Thr-NH$_2$ Dop2-Lys(Dop2)-Lys-D-Tyr-D-Tyr-c[Cys-3-I-Tyr-D-Trp-Lys-Thr-Cys]-Thr-NH$_2$ Dop2-D-Lys(Dop2)-D-Tyr-D-Tyr-c[Cys-3-I-Tyr-D-Trp-Lys-Thr-Cys]-Thr-NH$_2$ Dop2-D-Lys(Dop2)-Aepa-D-Tyr-D-Tyr-c[Cys-3-I-Tyr-D-Trp-Lys-Thr-Cys]-Thr-NH$_2$ Dop2-D-Lys(Dop2)-Lys-D-Tyr-D-Tyr-c[Cys-3-I-Tyr-D-Trp-Lys-Thr-Cys]-Thr-NH$_2$ Dop2-D-Lys(Dop2)-D-Phe-c[Cys-3-I-Tyr-D-Trp-Lys-Abu-Cys]-Thr-NH$_2$ Dop2-D-Lys(Dop2)-Aepa-D-Phe-c[Cys-3-I-Tyr-D-Trp-Lys-Abu-Cys]-Thr-NH$_2$ Dop2-Lys(Dop2)-D-Tyr-D-Tyr-c[Cys-3-I-Tyr-D-Trp-Lys-Abu-Cys]-Thr-NH$_2$ Dop2-Lys(Dop2)-D-Phe-c[Cys-3-I-Tyr-D-Trp-Lys-Abu-Cys]-Thr-NH$_2$ Dop2-Lys(Dop2)-Aepa-D-Phe-c[Cys-3-I-Tyr-D-Trp-Lys-Abu-Cys]-Thr-NH$_2$ Dop2-D-Lys(Dop2)-c[Cys-3-I-Tyr-D-Trp-Lys-Abu-Cys]-Thr-NH$_2$ Dop2-Lys(Dop2)-c[Cys-3-I-Tyr-D-Trp-Lys-Abu-Cys]-Thr-NH$_2$ Dop2-Lys(Dop2)-Lys-D-Tyr-D-Tyr-c[Cys-3-I-Tyr-D-Trp-Lys-Abu-Cys]-Thr-NH$_2$ Dop2-D-Lys(Dop2)-D-Tyr-D-Tyr-c[Cys-3-I-Tyr-D-Trp-Lys-Abu-Cys]-Thr-NH$_2$ Dop2-D-Lys(Dop2)-Lys-D-Tyr-D-Tyr-c[Cys-3-I-Tyr-D-Trp-Lys-Abu-Cys]-Thr-NH$_2$ -continued Dop2-D-Lys(Dop2)-D-Phe-c[Cys-3-I-Tyr-D-Trp-Lys-Val-Cys]-Thr-NH$_2$ Dop2-D-Lys(Dop2)-Aepa-D-Phe-c[Cys-3-I-Tyr-D-Trp-Lys-Val-Cys]-Thr-NH$_2$ Dop2-Lys(Dop2)-D-Tyr-D-Tyr-c[Cys-3-I-Tyr-D-Trp-Lys-Val-Cys]-Thr-NH$_2$ Dop2-Lys(Dop2)-D-Phe-c[Cys-3-I-Tyr-D-Trp-Lys-Val-Cys]-Thr-NH$_2$ Dop2-Lys(Dop2)-Aepa-D-Phe-c[Cys-3-I-Tyr-D-Trp-Lys-Val-Cys]-Thr-NH$_2$ Dop2-D-Lys(Dop2)-c[Cys-3-I-Tyr-D-Trp-Lys-Val-Cys]-Thr-NH$_2$ Dop2-Lys(Dop2)-c[Cys-3-I-Tyr-D-Trp-Lys-Val-Cys]-Thr-NH$_2$ Dop2-Lys(Dop2)-Lys-D-Tyr-D-Tyr-c[Cys-3-I-Tyr-D-Trp-Lys-Val-Cys]-Thr-NH$_2$ Dop2-D-Lys(Dop2)-D-Tyr-D-Tyr-c[Cys-3-I-Tyr-D-Trp-Lys-Val-Cys]-Thr-NH$_2$ Dop2-D-Lys(Dop2)-Lys-D-Tyr-D-Tyr-c[Cys-3-I-Tyr-D-Trp-Lys-Val-Cys]-Thr-NH$_2$ Dop3-Lys(Dop3)-D-Phe-c[Cys-3-I-Tyr-D-Trp-Lys-Thr-Cys]-Thr-NH$_2$ Dop4-Lys(Dop4)-D-Phe-c[Cys-3-I-Tyr-D-Trp-Lys-Thr-Cys]-Thr-NH$_2$ Dop3-Lys(Dop3)-Aepa-D-Phe-c[Cys-3-I-Tyr-D-Trp-Lys-Thr-Cys]-Thr-NH$_2$ Dop4-Lys(Dop4)-Aepa-D-Phe-c[Cys-3-I-Tyr-D-Trp-Lys-Thr-Cys]-Thr-NH$_2$ Dop5-D-Lys(Dop5)-D-Phe-c[Cys-3-I-Tyr-D-Trp-Lys-Thr-Cys]-Thr-NH$_2$ Dop5-Lys(Dop5)-D-Tyr-D-Tyr-c[Cys-3-I-Tyr-D-Trp-Lys-Thr-Cys]-Thr-NH$_2$ Dop5-Lys(Dop5)-D-Phe-c[Cys-3-I-Tyr-D-Trp-Lys-Thr-Cys]-Thr-NH$_2$ Dop5-D-Lys(Dop5)-c[Cys-3-I-Tyr-D-Trp-Lys-Thr-Cys]-Thr-NH$_2$ Dop5-Lys(Dop5)-c[Cys-3-I-Tyr-D-Trp-Lys-Thr-Cys]-Thr-NH$_2$ Dop5-Lys(Dop5)-Lys-D-Tyr-D-Tyr-c[Cys-3-I-Tyr-D-Trp-Lys-Thr-Cys]-Thr-NH$_2$ Dop5-D-Lys(Dop5)-D-Tyr-D-Tyr-c[Cys-3-I-Tyr-D-Trp-Lys-Thr-Cys]-Thr-NH$_2$ Dop5-D-Lys(Dop5)-Lys-D-Tyr-D-Tyr-c[Cys-3-I-Tyr-D-Trp-Lys-Thr-Cys]-Thr-NH$_2$ Dop5-D-Lys(Dop5)-D-Phe-c[Cys-3-I-Tyr-D-Trp-Lys-Abu-Cys]-Thr-NH$_2$ Dop5-Lys(Dop5)-D-Tyr-D-Tyr-c[Cys-3-I-Tyr-D-Trp-Lys-Abu-Cys]-Thr-NH$_2$ Dop5-Lys(Dop5)-D-Phe-c[Cys-3-I-Tyr-D-Trp-Lys-Abu-Cys]-Thr-NH$_2$ Dop5-D-Lys(Dop5)-c[Cys-3-I-Tyr-D-Trp-Lys-Abu-Cys]-Thr-NH$_2$ Dop5-Lys(Dop5)-c[Cys-3-I-Tyr-D-Trp-Lys-Abu-Cys]-Thr-NH$_2$ Dop5-Lys(Dop5)-Lys-D-Tyr-D-Tyr-c[Cys-3-I-Tyr-D-Trp-Lys-Abu-Cys]-Thr-NH$_2$ Dop5-D-Lys(Dop5)-D-Tyr-D-Tyr-c[Cys-3-I-Tyr-D-Trp-Lys-Abu-Cys]-Thr-NH$_2$ Dop5-D-Lys(Dop5)-Lys-D-Tyr-D-Tyr-c[Cys-3-I-Tyr-D-Trp-Lys-Abu-Cys]-Thr-NH$_2$ Dop5-D-Lys(Dop5)-D-Phe-c[Cys-3-I-Tyr-D-Trp-Lys-Val-Cys]-Thr-NH$_2$ Dop5-Lys(Dop5)-D-Tyr-D-Tyr-c[Cys-3-I-Tyr-D-Trp-Lys-Val-Cys]-Thr-NH$_2$ -continued Dop5-Lys(Dop5)-D-Phe-c[Cys-3-I-Tyr-D-Trp-Lys-Val-Cys]-Thr-NH₂

Dop5-D-Lys(Dop5)-c[Cys-3-I-Tyr-D-Trp-Lys-Val-Cys]-Thr-NH₂

Dop5-Lys(Dop5)-c[Cys-3-I-Tyr-D-Trp-Lys-Val-Cys]-Thr-NH₂

Dop5-Lys(Dop5)-Lys-D-Tyr-D-Tyr-c[Cys-3-I-Tyr-D-Trp-Lys-Val-Cys]-Thr-NH₂

Dop5-D-Lys(Dop5)-D-Tyr-D-Tyr-c[Cys-3-I-Tyr-D-Trp-Lys-Val-Cys]-Thr-NH₂

Dop5-D-Lys(Dop5)-Lys-D-Tyr-D-Tyr-c[Cys-3-I-Tyr-D-Trp-Lys-Val-Cys]-Thr-NH₂

Dop6-Lys(Dop6)-c[Cys-3-I-Tyr-D-Trp-Lys-Thr-Cys]-Thr-NH₂

Dop7-Lys(Dop7)-c[Cys-3-I-Tyr-D-Trp-Lys-Thr-Cys]-Thr-NH₂

Dop8-Lys(Dop8)-c[Cys-3-I-Tyr-D-Trp-Lys-Thr-Cys]-Thr-NH₂

Dop9-Lys(Dop9)-c[Cys-3-I-Tyr-D-Trp-Lys-Thr-Cys]-Thr-NH₂

Dop10-Lys(Dop10)-c[Cys-3-I-Tyr-D-Trp-Lys-Thr-Cys]-Thr-NH₂

Dop11-Lys(Dop11)-c[Cys-3-I-Tyr-D-Trp-Lys-Thr-Cys]-Thr-NH₂

Dop12-Lys(Dop12)-c[Cys-3-I-Tyr-D-Trp-Lys-Thr-Cys]-Thr-NH₂

Dop13-Lys(Dop13)-c[Cys-3-I-Tyr-D-Trp-Lys-Thr-Cys]-Thr-NH₂

Dop6-Lys(Dop6)-D-Phe-c[Cys-3-I-Tyr-D-Trp-Lys-Thr-Cys]-Thr-NH₂

Dop7-Lys(Dop7)-D-Phe-c[Cys-3-I-Tyr-D-Trp-Lys-Thr-Cys]-Thr-NH₂

Dop8-Lys(Dop8)-D-Phe-c[Cys-3-I-Tyr-D-Trp-Lys-Thr-Cys]-Thr-NH₂

Dop9-Lys(Dop9)-D-Phe-c[Cys-3-I-Tyr-D-Trp-Lys-Thr-Cys]-Thr-NH₂

Dop10-Lys(Dop10)-D-Phe-c[Cys-3-I-Tyr-D-Trp-Lys-Thr-Cys]-Thr-NH₂

Dop11-Lys(Dop11)-D-Phe-c[Cys-3-I-Tyr-D-Trp-Lys-Thr-Cys]-Thr-NH₂

Dop12-Lys(Dop12)-D-Phe-c[Cys-3-I-Tyr-D-Trp-Lys-Thr-Cys]-Thr-NH₂
and

Dop13-Lys(Dop13)-D-Phe-c[Cys-3-I-Tyr-D-Trp-Lys-Thr-Cys]-Thr-NH₂.

OTHER EMBODIMENTS

From the above description, one skilled in the art can easily ascertain the essential characteristics of the present invention, and without departing from the spirit and scope thereof, can make various changes and modifications of the invention to adapt it to various uses and conditions. Thus, other embodiments are also within the claims.

The invention claimed is:

1. A method for synthesizing a therapeutic ghrelin peptide analogue of formula I $$R^1\text{-}A^1\text{-}A^2\text{-}A^3\text{-}A^4\text{-}A^5\text{-}R^2 \qquad (I)$$

using stepwise solid-phase fluorenylmethyloxycarbonyl (Fmoc)-chemistry, the method comprising:
 (a) swelling a Fmoc-Sieber resin comprising an Fmoc group in a first dipolar aprotic solvent;
 (b) de-protecting the Fmoc group of the Fmoc-Sieber resin with a solution of piperidine in a second dipolar aprotic solvent;
 (c) washing the resin after Fmoc de-protection with a third dipolar aprotic solvent;
 (d) activating an Fmoc-amino acid for coupling to the de-protected resin by dissolving the Fmoc-amino acid and one or more coupling reagents in a fourth dipolar aprotic solvent, then adding a base and stirring;
 (e) contacting the activated Fmoc-amino acid solution and the resin in a reactor;
 (f) coupling the activated Fmoc-amino acid with the one or more coupling reagents, the one or more coupling reagents comprising: (2-(6-chloro-H-benzotriazole-1-yl)-1,1,3,3-tetramethylaminium hexafluorophosphate) (HCTU) or 2-(1H-benzotriazole-1-yl)-1,1,3,3-tetramethyluronium tetrafluoroborate (TBTU)/1-hydroxybenzotriazole (HOBt); a base; and a fifth dipolar aprotic solvent;
 (g) washing the resin;
 (h) repeating steps (b)-(g) until the ghrelin peptide analogue is formed;
 (i) contacting the resin with a cleavage cocktail to cleave the ghrelin peptide analogue, resulting in cleavage mixture and resin;
 (j) filtering the cleavage mixture from the resin; and
 (k) evaporating the cleavage mixture filtrate and precipitating the crude product from the concentrated solution with an organic solvent to yield a partially purified ghrelin peptide analogue;
wherein:
$A^1$ is Aib, Apc or Inp;
$A^2$ is D-Bal, D-Bip, D-Bpa, D-Dip, D-1Nal, D-2Nal, D-Ser(Bzl), or D-Trp;

A³ is D-Bal, D-Bip, D-Bpa, D-Dip, D-1Nal, D-2Nal, D-Ser (Bzl), or D-Trp;
A⁴ is 2Fua, Orn, 2Pal, 3Pal, 4Pal, Pff, Phe, Pim, Taz, 2Thi, 3Thi, Thr(Bzl);
A⁵ is Apc, Dab, Dap, Lys, Orn, or deleted;
R¹ is hydrogen; and
R² is OH or NH₂;
provided that
when A⁵ is Dab, Dap, Lys, or Orn, then:
   A² is D-Bip, D-Bpa, D-Dip or D-Bal; or
   A³ is D-Bip, D-Bpa, D-Dip or D-Bal; or
   A⁴ is 2Thi, 3Thi, Taz, 2Fua, 2Pal, 3Pal, 4Pal, Orn, Thr(Bzl), or Pff;
when A⁵ is deleted, then:
   A³ is D-Bip, D-Bpa, or D-Dip; or A⁴ is 2Fua, Pff, Taz, or Thr(Bzl); or
   A¹ is Apc and
      A² is D-Bip, D-Bpa, D-Dip or D-Bal; or
      A³ is D-Bip, D-Bpa, D-Dip or D-Bal; or
      A⁴ is 2Thi, 3Thi, Orn, 2Pal, 3Pal, or 4Pal.

2. The method according to claim 1, wherein the first dipolar aprotic solvent comprises dimethylformamide (DMF).

3. The method according to claim 1, wherein said base is a tertiary amine base.

4. The method according to claim 1, wherein said cleavage cocktail comprises a solution of up to 25% v/v trifluoroacetic acid (TFA), one or more scavengers, and dichloromethane (DCM), and wherein said one or more scavengers is triisopropylsilane (TIPS), triethylsilane (TES), phenol, anisole, thioanisole, water, ethanedithiol (EDT), 1-dodecanethiol, dithiothreitol (DTT) and/or indole.

5. The method according to claim 4, wherein said one or more scavengers is TIPS, TES, anisole and/or water.

6. The method according to claim 5, wherein said cleavage cocktail comprises:
15 to 25% v/v TFA, and
2.5 to 12% v/v TIPS, and
the balance is DCM,
wherein the ghrelin peptide analogue comprises a tert-butyloxycarbonyl (Boc) and/or tert-butyl ether (tBu) side chain protecting group, and wherein the method further comprises removing the Boc and/or tBu.

7. The method according to claim 6, wherein said cleaving of said peptide from the Fmoc-Sieber resin occurs simultaneously with the removing of said side chain protecting groups.

8. The method according to claim 1, wherein the second dipolar aprotic solvent is DMF, and wherein the concentration of said piperidine in DMF is less than 20% (v/v).

9. The method according to claim 1, wherein in step (f) the amino acids are coupled using a coupling reagent combination comprising TBTU/HOBt/N,N-diisopropylethylamine (DIEA), HBTU/HOBt/DIEA, HATU/DIEA, HCTU/DIEA, DIC/HOBt, DIC/HOAt, HATU/HOBt/DIEA, or HCTU/HOBt/DIEA.

10. A method for synthesizing a therapeutic ghrelin peptide analogue of formula I

$$R^1\text{-}A^1\text{-}A^2\text{-}A^3\text{-}A^4\text{-}A^5\text{-}R^2 \quad (I)$$

using stepwise solid-phase Fmoc-chemistry, the method comprising the successive steps of:
(a) swelling a Fmoc-Sieber resin comprising an Fmoc group in dimethylformamide (DMF);
(b) de-protecting the Fmoc group with a solution of piperidine in DMF;
(c) washing the resin after Fmoc de-protection with DMF;
(d) activating an Fmoc-amino acid for coupling to the de-protected resin by dissolving the Fmoc-amino acid and one or more coupling reagents in DMF then adding N,N-diisopropylethylamine (DIEA) and stirring;
(e) contacting the activated Fmoc-amino acid solution and the resin in a reactor;
(f) coupling the activated Fmoc-amino acid with a coupling reagent combination, the coupling reagent combination comprising: (2-(6-chloro-1H-benzotriazole-1-yl)-1,1,3,3-tetramethylaminium hexafluorophosphate) (HCTU) or 2-(1H-benzotriazole-1-yl)-1,1,3,3-tetramethyluronium tetrafluoroborate (TBTU)/1-hydroxybenzotriazole (HOBt); N,N-diisopropylethylamine (DIEA); and DMF;
(g) washing the resin;
(h) repeating steps (b)-(g) until the ghrelin peptide analogue is formed;
(i) contacting the resin with a cleavage cocktail to cleave the ghrelin peptide analogue from the resin resulting in cleavage mixture and resin;
(j) filtering the cleavage mixture from the resin; and
(k) evaporating the cleavage mixture filtrate and precipitating the crude product from the concentrated solution with an organic solvent to yield a partially purified ghrelin peptide analogue;
wherein:
A¹ is Aib, Apc or Inp;
A² is D-Bal, D-Bip, D-Bpa, D-Dip, D-1Nal, D-2Nal, D-Ser (Bzl), or D-Trp;
A³ is D-Bal, D-Bip, D-Bpa, D-Dip, D-1Nal, D-2Nal, D-Ser (Bzl), or D-Trp;
A⁴ is 2Fua, Orn, 2Pal, 3Pal, 4Pal, Pff, Phe, Pim, Taz, 2Thi, 3Thi, Thr(Bzl);
A⁵ is Apc, Dab, Dap, Lys, Orn, or deleted;
R¹ is hydrogen; and
R² is OH or NH₂;
provided that
when A⁵ is Dab, Dap, Lys, or Orn, then:
   A² is D-Bip, D-Bpa, D-Dip or D-Bal, or
   A³ is D-Bip, D-Bpa, D-Dip or D-Bal, or
   A⁴ is 2Thi, 3Thi, Taz, 2Fua, 2Pal, 3Pal, 4Pal, Orn, Thr(Bzl), or Pff;
when A⁵ is deleted, then:
   A³ is D-Bip, D-Bpa, or D-Dip; or A⁴ is 2Fua, Pff, Taz, or Thr(Bzl), or
   A¹ is Apc and
      A² is D-Bip, D-Bpa, D-Dip or D-Bal, or
      A³ is D-Bip, D-Bpa, D-Dip or D-Bal, or
      A⁴ is 2Thi, 3Thi, Orn, 2Pal, 3Pal, or 4Pal.

11. The method according to claim 1, wherein said ghrelin peptide analogue is H-Inp-D-Bal-D-Trp-Phe-Apc-NH₂.

12. The method according to claim 3, wherein the tertiary amine base is N,N-diisopropylethylamine (DIEA).

13. The method according to claim 9, wherein the coupling reagent combination comprises HCTU/DIEA or TBTU/HOBt/DIEA.

14. The method according to claim 1, wherein the first, second, third, fourth, and fifth dipolar aprotic solvents are DMF.

15. The method of claim 1, wherein
A³ is D-Bal, D-Bpa, D-Dip, D-1Nal, D-2Nal, or D-Trp;
A⁴ is Orn, 3Pal, 4Pal, Pff, Phe, Pim, Taz, 2Thi, or Thr(Bzl); and
A⁵ is Apc, Lys, or deleted.

16. The method of claim 1, wherein
A¹ is Apc or Inp;
A² is D-Bal, D-Bip, D-1Nal, or D-2Nal;

$A^3$ is D-Bal, D-1Nal, D-2Nal, or D-Trp;
$A^4$ is 3Pal, 4Pal, Pff, Phe, Pim, Taz, 2Thi, or Thr(Bzl); and
$A^5$ is Apc or Lys.

17. The method of claim 1, wherein the ghrelin peptide analogue is
H-Inp-D-Bal-D-Trp-Phe-Apc-$NH_2$,
H-Inp-D-2Nal-D-Trp-Phe-Apc-$NH_2$,
H-Inp-D-Bal-D-Trp-2Thi-Apc-$NH_2$, or
H-Inp-D-Bal-D-Trp-Taz-Apc-$NH_2$.

18. The method of claim 1, wherein the ghrelin peptide analogue is
H-Inp-D-Bal-D-Trp-Phe-Apc-$NH_2$.

* * * * *